(12) United States Patent
Leimbach et al.

(10) Patent No.: US 8,695,866 B2
(45) Date of Patent: Apr. 15, 2014

(54) SURGICAL INSTRUMENT HAVING A POWER CONTROL CIRCUIT

(75) Inventors: Richard L. Leimbach, Cincinnati, OH (US); Richard F. Schwemberger, Cincinnati, OH (US); Brett E. Swensgard, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 545 days.

(21) Appl. No.: 12/896,381

(22) Filed: Oct. 1, 2010

(65) Prior Publication Data

US 2012/0080477 A1 Apr. 5, 2012

(51) Int. Cl.
*A61B 17/068* (2006.01)

(52) U.S. Cl.
USPC ............... 227/175.2; 227/178.1; 227/175.1; 227/2

(58) Field of Classification Search
USPC .............. 227/175.1, 178.1, 2, 175.2
See application file for complete search history.

(56) References Cited

U.S. PATENT DOCUMENTS

| | | |
|---|---|---|
| 3,551,987 A | 1/1971 | Wilkinson |
| 4,773,420 A | 9/1988 | Green |
| 4,844,068 A | 7/1989 | Arata et al. |
| 4,903,697 A | 2/1990 | Resnick et al. |
| 5,074,454 A | 12/1991 | Peters |
| 5,405,072 A | 4/1995 | Zlock et al. |
| 5,413,272 A | 5/1995 | Green et al. |
| 5,415,334 A | 5/1995 | Williamson, IV et al. |
| 5,480,089 A | 1/1996 | Blewett |
| 5,482,197 A | 1/1996 | Green et al. |
| 5,485,952 A | 1/1996 | Fontayne |
| 5,487,499 A | 1/1996 | Sorrentino et al. |
| 5,497,933 A | 3/1996 | DeFonzo et al. |
| 5,505,363 A | 4/1996 | Green et al. |
| 5,529,235 A | 6/1996 | Boiarski et al. |
| 5,535,934 A | 7/1996 | Boiarski et al. |
| 5,540,375 A | 7/1996 | Bolanos et al. |
| 5,542,594 A | 8/1996 | McKean et al. |
| 5,551,622 A | 9/1996 | Yoon |
| 5,562,241 A | 10/1996 | Knodel et al. |
| 5,564,615 A | 10/1996 | Bishop et al. |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Datasheet for Panasonic TK Relays Ultra Low Profile 2 A Polarized Relay, Copyright Matsushita Electric Works, Ltd. (Known of at least as early as Aug. 17, 2010), 5 pages.

(Continued)

*Primary Examiner* — Michelle Lopez

(57) ABSTRACT

Various embodiments are directed to a powered surgical instrument for cutting and fastening tissue. The instrument may comprise an end effector comprising a first jaw member and a second jaw member, a drive device, a clamping trigger, and a control circuit. The control circuit may comprise a power supply, a firing switch, a clamp switch, a switching device and an end-of-stroke switch. The firing switch may be electrically connected to, upon actuation, connect the power supply to the drive device via a first connection comprising the switching device and the firing switch.

19 Claims, 43 Drawing Sheets

(56) References Cited

U.S. PATENT DOCUMENTS

| | | |
|---|---|---|
| 5,577,654 A | 11/1996 | Bishop |
| 5,588,579 A | 12/1996 | Schnut et al. |
| 5,601,224 A | 2/1997 | Bishop et al. |
| 5,603,443 A | 2/1997 | Clark et al. |
| 5,607,094 A | 3/1997 | Clark et al. |
| 5,628,446 A | 5/1997 | Geiste et al. |
| 5,630,539 A | 5/1997 | Plyley et al. |
| 5,639,008 A | 6/1997 | Gallagher et al. |
| 5,651,491 A | 7/1997 | Heaton et al. |
| 5,653,373 A | 8/1997 | Green et al. |
| 5,662,258 A | 9/1997 | Knodel et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,692,668 A | 12/1997 | Schulze et al. |
| 5,704,534 A | 1/1998 | Huitema et al. |
| 5,711,472 A | 1/1998 | Bryan |
| 5,715,987 A | 2/1998 | Kelley et al. |
| 5,732,871 A | 3/1998 | Clark et al. |
| 5,797,536 A | 8/1998 | Smith et al. |
| 5,836,503 A | 11/1998 | Ehrenfels et al. |
| 5,839,639 A | 11/1998 | Sauer et al. |
| 5,871,135 A | 2/1999 | Williamson, IV et al. |
| 5,941,442 A | 8/1999 | Geiste et al. |
| 6,241,139 B1 | 6/2001 | Milliman et al. |
| 6,250,532 B1 | 6/2001 | Green et al. |
| 6,488,196 B1 | 12/2002 | Fenton, Jr. |
| 6,679,410 B2 | 1/2004 | Würsch et al. |
| 6,722,552 B2 | 4/2004 | Fenton, Jr. |
| 6,755,338 B2 | 6/2004 | Hahnen et al. |
| 6,786,382 B1 | 9/2004 | Hoffman |
| 6,830,174 B2 | 12/2004 | Hillstead et al. |
| 6,866,178 B2 | 3/2005 | Adams et al. |
| 6,874,669 B2 | 4/2005 | Adams et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,964,363 B2 | 11/2005 | Wales et al. |
| 6,978,921 B2 | 12/2005 | Shelton, IV et al. |
| 6,981,628 B2 | 1/2006 | Wales |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,111,769 B2 | 9/2006 | Wales et al. |
| 7,140,527 B2 | 11/2006 | Ehrenfels et al. |
| 7,182,239 B1 | 2/2007 | Myers |
| 7,237,708 B1 | 7/2007 | Guy et al. |
| 7,246,734 B2 | 7/2007 | Shelton, IV |
| 7,303,106 B2 | 12/2007 | Milliman et al. |
| 7,303,108 B2 | 12/2007 | Shelton, IV |
| 7,328,828 B2 | 2/2008 | Ortiz et al. |
| 7,334,717 B2 | 2/2008 | Rethy et al. |
| 7,334,718 B2 | 2/2008 | McAlister et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,075 B2 | 8/2008 | Holsten et al. |
| 7,407,076 B2 | 8/2008 | Racenet et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 * | 9/2008 | Marczyk ............ 227/175.1 |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,490,749 B2 | 2/2009 | Schall et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,563 B2 | 6/2009 | Mather et al. |
| 7,549,564 B2 | 6/2009 | Boudreaux |
| 7,556,185 B2 | 7/2009 | Viola |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,624,902 B2 | 12/2009 | Marczyk et al. |
| 7,631,793 B2 | 12/2009 | Rethy et al. |
| 7,637,409 B2 | 12/2009 | Marczyk |
| 7,644,848 B2 | 1/2010 | Swayze et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,708,180 B2 | 5/2010 | Murray et al. |
| 7,717,312 B2 | 5/2010 | Beetel |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,891,531 B1 | 2/2011 | Ward |
| 7,900,805 B2 | 3/2011 | Shelton, IV et al. |

(56) References Cited

U.S. PATENT DOCUMENTS

| | | |
|---|---|---|
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,934,630 B2 | 5/2011 | Shelton, IV et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,967,180 B2 | 6/2011 | Scirica |
| 8,006,885 B2 | 8/2011 | Marczyk |
| 8,011,550 B2 | 9/2011 | Aranyi et al. |
| 8,011,551 B2 | 9/2011 | Marczyk et al. |
| 8,020,742 B2 | 9/2011 | Marczyk |
| 8,028,883 B2 | 10/2011 | Stopek |
| D650,074 S | 12/2011 | Hunt et al. |
| 8,083,119 B2 | 12/2011 | Prommersberger |
| 8,091,756 B2 | 1/2012 | Viola |
| 8,100,310 B2 | 1/2012 | Zemlok |
| 8,157,153 B2 | 4/2012 | Shelton, IV et al. |
| 8,205,781 B2 | 6/2012 | Baxter, III et al. |
| 8,210,415 B2 | 7/2012 | Ward |
| 8,256,654 B2 | 9/2012 | Bettuchi et al. |
| 8,267,300 B2 | 9/2012 | Boudreaux |
| 8,292,155 B2 | 10/2012 | Shelton, IV et al. |
| 8,333,313 B2 | 12/2012 | Boudreaux et al. |
| 8,360,296 B2 | 1/2013 | Zingman |
| 8,393,514 B2 | 3/2013 | Shelton, IV et al. |
| 8,453,914 B2 | 6/2013 | Laurent et al. |
| 8,459,525 B2 | 6/2013 | Yates et al. |
| 2005/0103819 A1 | 5/2005 | Racenet et al. |
| 2005/0274768 A1 | 12/2005 | Cummins et al. |
| 2006/0049229 A1 | 3/2006 | Milliman et al. |
| 2006/0201989 A1 | 9/2006 | Ojeda |
| 2006/0226196 A1 | 10/2006 | Hueil et al. |
| 2007/0023476 A1 | 2/2007 | Whitman et al. |
| 2007/0023477 A1 | 2/2007 | Whitman et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1* | 8/2007 | Swayze et al. ............. 227/178.1 |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082125 A1 | 4/2008 | Murray et al. |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0237296 A1 | 10/2008 | Boudreaux et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0314960 A1 | 12/2008 | Marczyk et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0078736 A1 | 3/2009 | Van Lue |
| 2009/0108048 A1 | 4/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0242610 A1 | 10/2009 | Shelton, IV et al. |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0108740 A1 | 5/2010 | Pastorelli et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |

(56) References Cited

U.S. PATENT DOCUMENTS

| | | |
|---|---|---|
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174861 A1 | 7/2011 | Shelton, Iv et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0253765 A1 | 10/2011 | Nicholas et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138658 A1 | 6/2012 | Ullrich et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0283748 A1 | 11/2012 | Ortiz et al. |
| 2012/0286019 A1 | 11/2012 | Hueil et al. |

(56) References Cited

U.S. PATENT DOCUMENTS

| | | |
|---|---|---|
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0105551 A1 | 5/2013 | Zingman |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |

FOREIGN PATENT DOCUMENTS

| | | |
|---|---|---|
| CA | 2514274 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |

(56) References Cited

FOREIGN PATENT DOCUMENTS

| | | |
|---|---|---|
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1897502 A1 | 3/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 2005894 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 A1 | 6/2009 |
| EP | 1550413 B1 | 6/2009 |
| EP | 1745748 B1 | 8/2009 |
| EP | 2090237 A1 | 8/2009 |
| EP | 2090241 A1 | 8/2009 |
| EP | 2090244 A2 | 8/2009 |
| EP | 2090245 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 2286738 A2 | 2/2011 |
| EP | 1690502 B1 | 3/2011 |
| EP | 1769755 B1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |

(56) References Cited

FOREIGN PATENT DOCUMENTS

| | | |
|---|---|---|
| EP | 1785102 B1 | 1/2012 |
| EP | 2090253 B1 | 3/2012 |
| EP | 2005895 B1 | 8/2012 |
| EP | 2090248 B1 | 8/2012 |
| EP | 1884206 B1 | 3/2013 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | S 58500053 A | 1/1983 |
| JP | 61-98249 A | 5/1986 |
| JP | S 61502036 A | 9/1986 |
| JP | S 63-147449 A | 6/1988 |
| JP | 63-203149 | 8/1988 |
| JP | 3-12126 A | 1/1991 |
| JP | 5-212039 A | 8/1993 |
| JP | 6007357 A | 1/1994 |
| JP | H 6-30945 A | 2/1994 |
| JP | H 6-121798 A | 5/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | H 09-501081 A | 2/1997 |
| JP | 2000-14632 | 1/2000 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001-517473 A | 10/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-521301 A | 7/2003 |
| JP | 2004-162035 A | 6/2004 |
| JP | 2004-329624 A | 11/2004 |
| JP | 2004-344663 | 12/2004 |
| JP | 2005-028147 A | 2/2005 |
| JP | 2005-028149 A | 2/2005 |
| JP | 2005-505309 A | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-034980 A | 2/2006 |
| JP | 2006-218297 A | 8/2006 |
| JP | 2006-281405 A | 10/2006 |
| JP | 2007-098130 A | 4/2007 |
| JP | 2007-117725 A | 5/2007 |
| JP | 2007-203057 A | 8/2007 |
| JP | 2007-229448 A | 9/2007 |
| JP | 2008-283459 A | 11/2008 |
| RU | 2008830 C1 | 3/1994 |
| RU | RU 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1333319 A2 | 8/1987 |
| SU | 1377053 A1 | 2/1988 |
| SU | 1561964 A1 | 5/1990 |
| SU | 1722476 A1 | 3/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |

(56) References Cited

FOREIGN PATENT DOCUMENTS

| | | |
|---|---|---|
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/046394 A1 | 4/2009 |
| WO | WO 2009/137761 A2 | 11/2009 |
| WO | WO 2010/030434 A1 | 3/2010 |

(56) References Cited

FOREIGN PATENT DOCUMENTS

| WO | WO 2010/063795 A1 | 6/2010 |
|---|---|---|
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

U.S. Appl. No. 12/884,838, filed Sep. 17, 2010, US PG Pub. 2012/0071711; Shelton, Frederick.

U.S. Appl. No. 12/884,995, filed Sep. 17, 2010, US PG Pub. 2012/0071866; Kerr, Wendy A.

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Stapler™ Technology," (2010), 2 pages.

Covidien Brochure, "Endo GIA™ Ultra Universal Stapler," (2010), 2 pages.

* cited by examiner

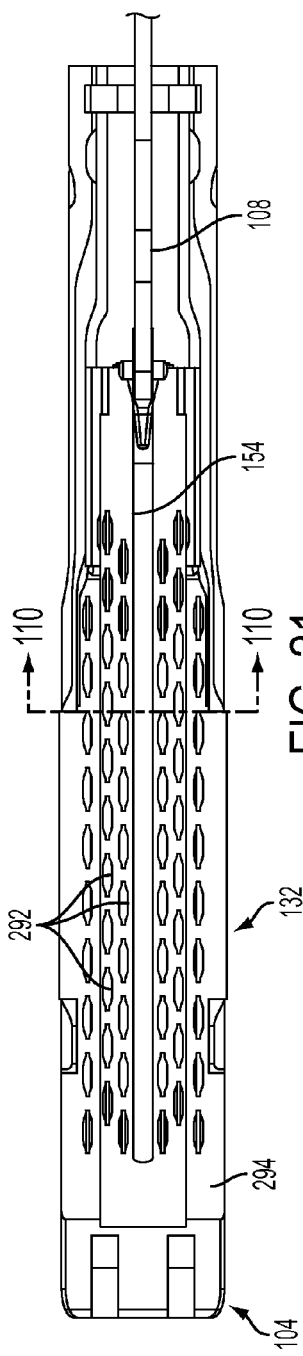
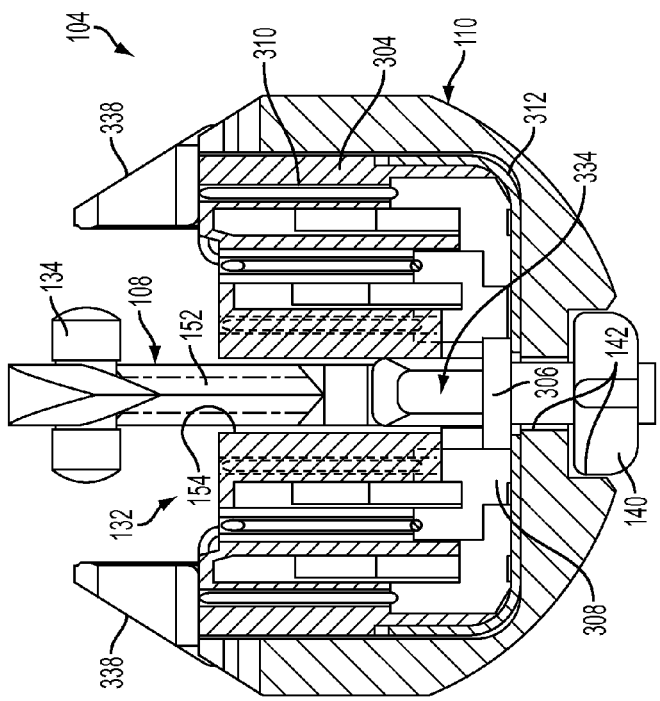
FIG. 21
FIG. 22

SURGICAL INSTRUMENT HAVING A POWER CONTROL CIRCUIT

BACKGROUND

Traditionally, surgical devices have been hand operated, with the force to fire and/or manipulate the instruments provided directly by the clinician. A growing number of surgical instruments, however, are powered surgical instruments where the force to fire and/or manipulate the instrument are provided by an automated device, such as an electric motor, pneumatic or hydraulic device, etc. Examples of powered surgical instruments may include such as cutters, graspers, and/or staplers, for example. Such powered instruments free instrument designers from the need to limit the amount of force required to fire to that which can reasonably be provided by a human clinician. Powered instruments may also be more easily used by smaller clinicians and/or clinicians with less physical strength.

One significant challenge of powered instruments, however, is lack of feedback to the clinician. When a clinician uses a manually powered surgical instrument, the clinician is able to know the state of the instrument based on the amount of force that the clinician has already provided to the instrument, the position of the handle trigger or other device for receiving clinician force, etc. In a powered instrument, however, such feedback may be absent. Accordingly, there is a need to compensate for the lack of feedback from powered surgical instruments.

DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 21 depicts one embodiment of the upper surface of the staple cartridge shown in FIG. 16 with the firing bar in its unfired, proximal position.

FIG. 22 depicts one embodiment of the end effector of the instrument of FIG. 1 near the pivot showing that the elongate channel has opposing ramp portions to thereby cooperate with the anvil to prevent tissue from jamming the end effector.

Figure 1:
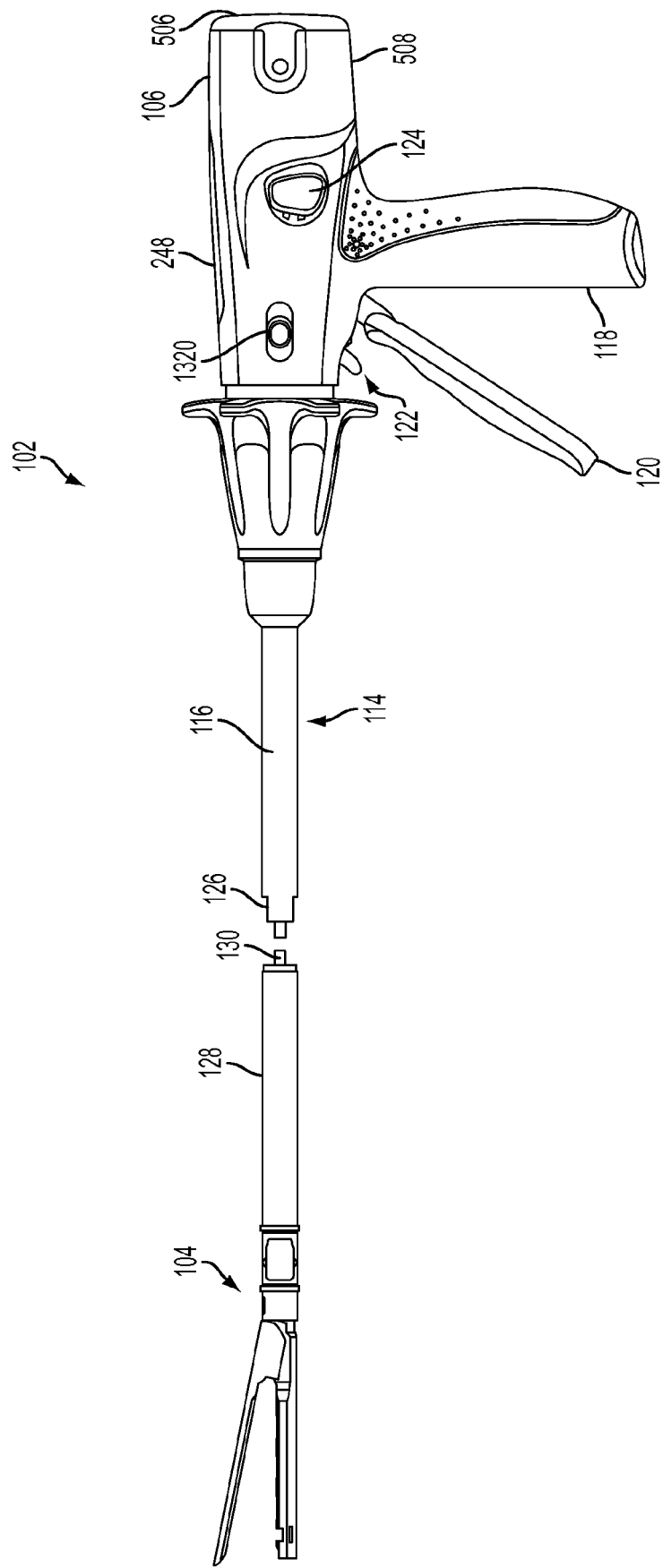
FIG. 1 shows one embodiment of a surgical stapling and cutting instrument with an electrically powered firing feature.
Figure 27:
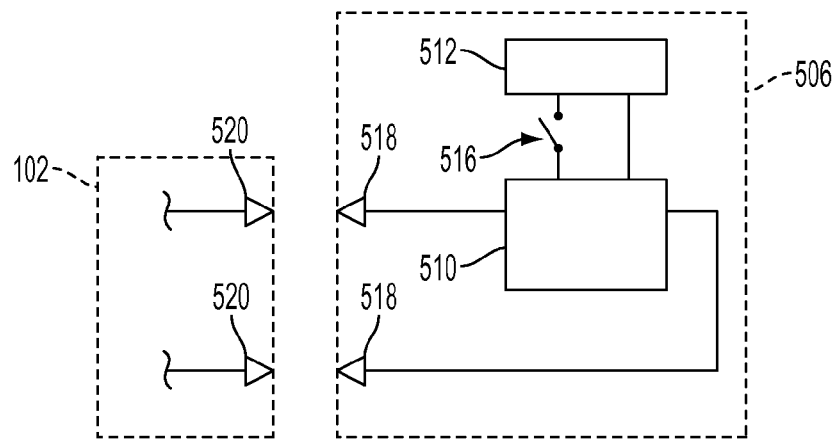
Figure 28:
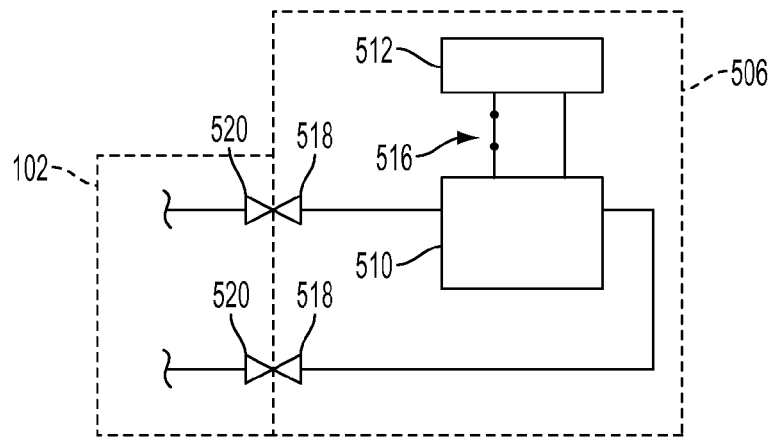
Figure 29:
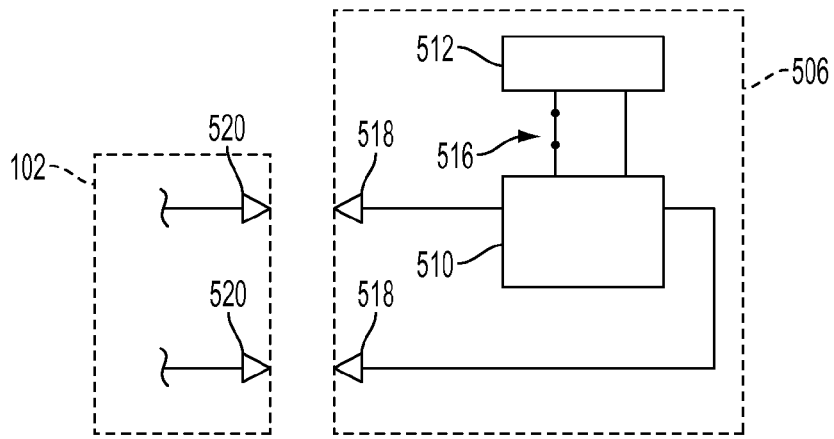

FIGS. 27-29 schematically illustrate one embodiment of a battery unit and a portion of the instrument of FIG. 1 showing the attachment and detachment of the battery unit to the instrument.

Figure 30:
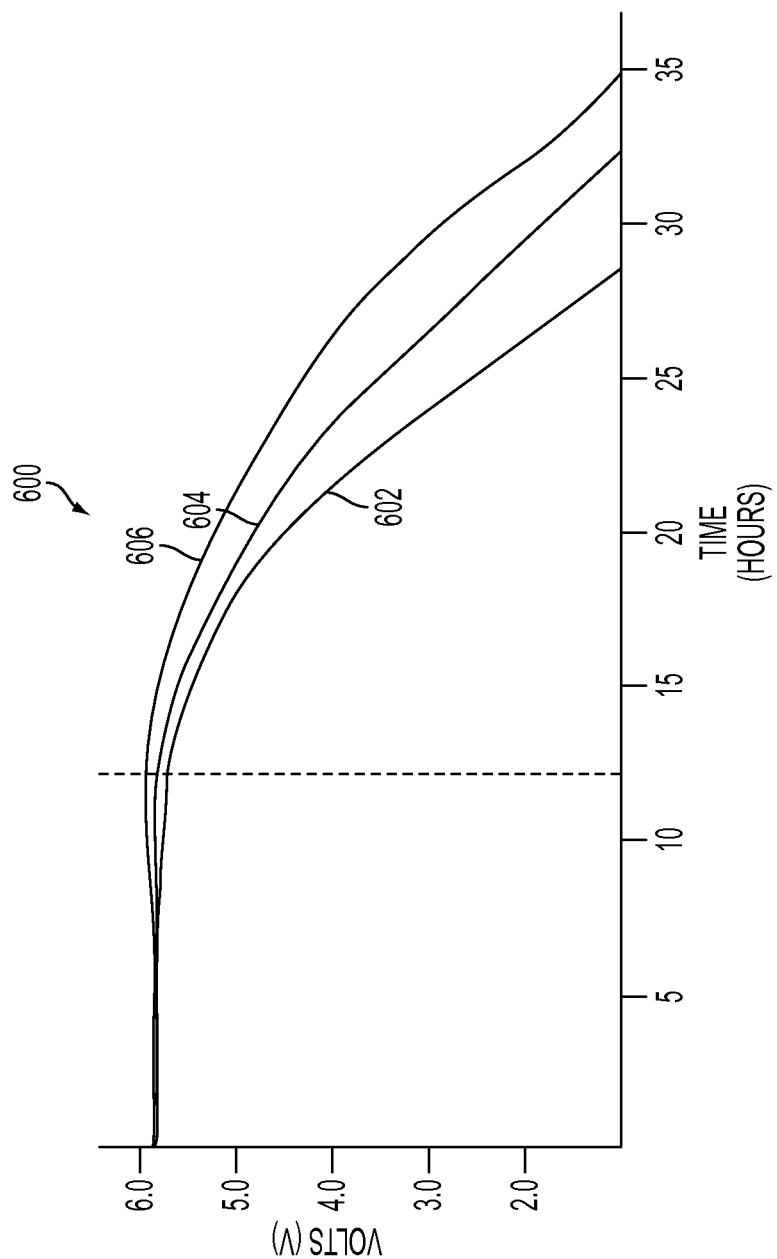

FIG. 30 illustrates a graph of the voltage level of one embodiment of the battery unit of FIGS. 27, 28 and 29 over time, as measured from the time of attachment to the instrument of FIG. 1.

Figure 31:
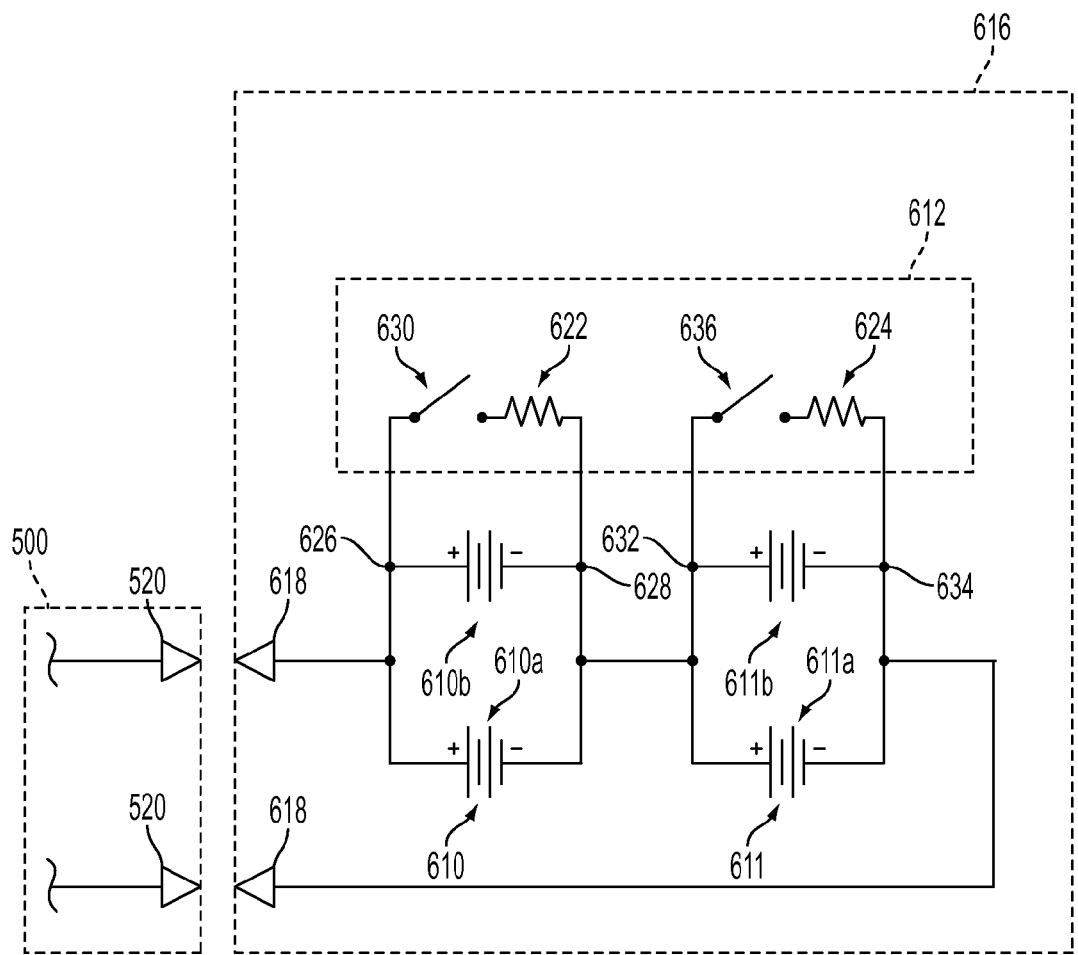

FIG. 31 shows one embodiment of a simplified circuit diagram of one embodiment of a battery unit comprising a drain.

Figure 32:
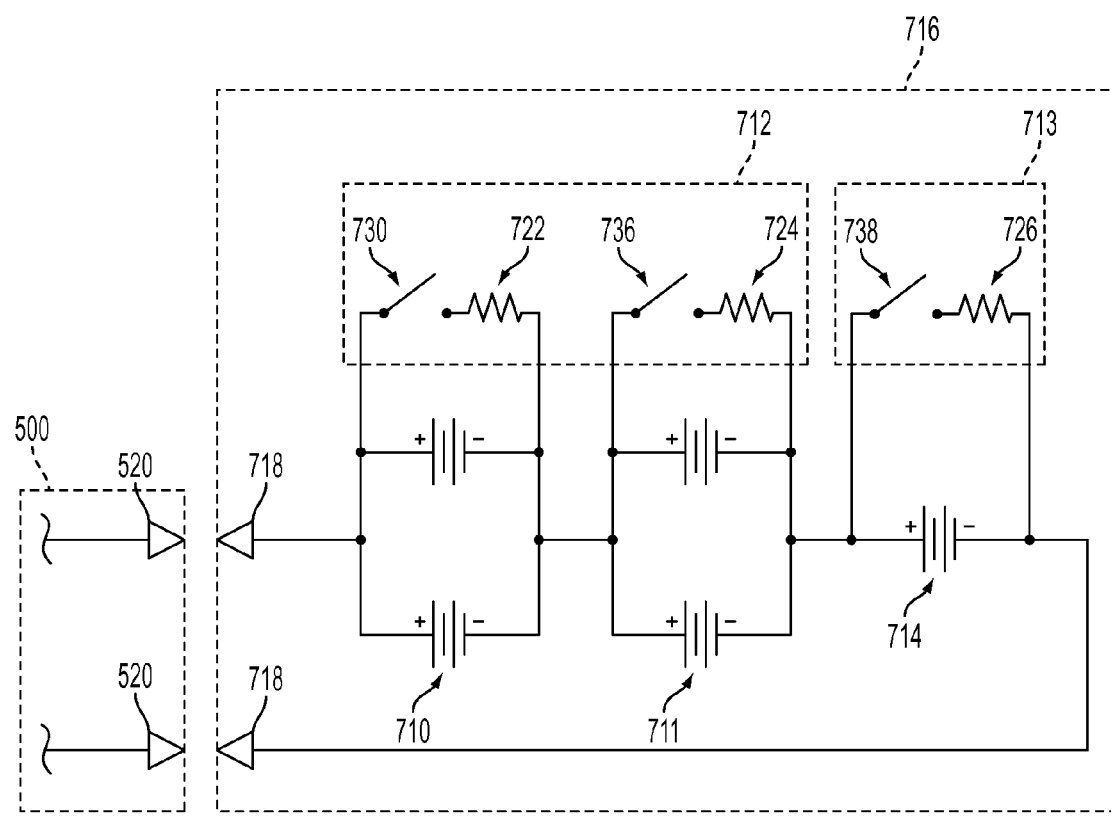
Figure 33:
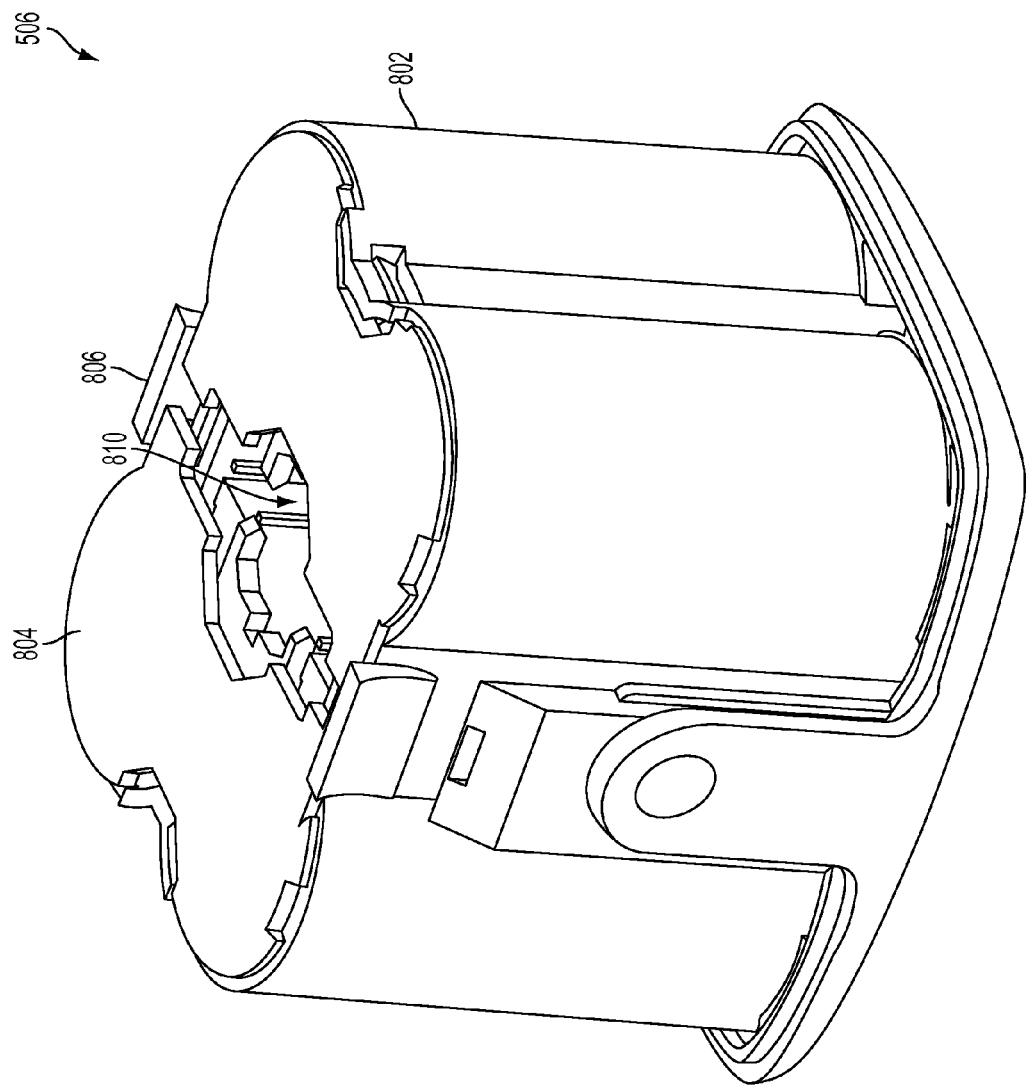

FIG. 32 is one embodiment of a simplified circuit diagram of one embodiment of a battery unit comprising a first drain and a second drain.

FIGS. 33-36 are perspective views of one embodiment of a battery unit.

Figure 35:
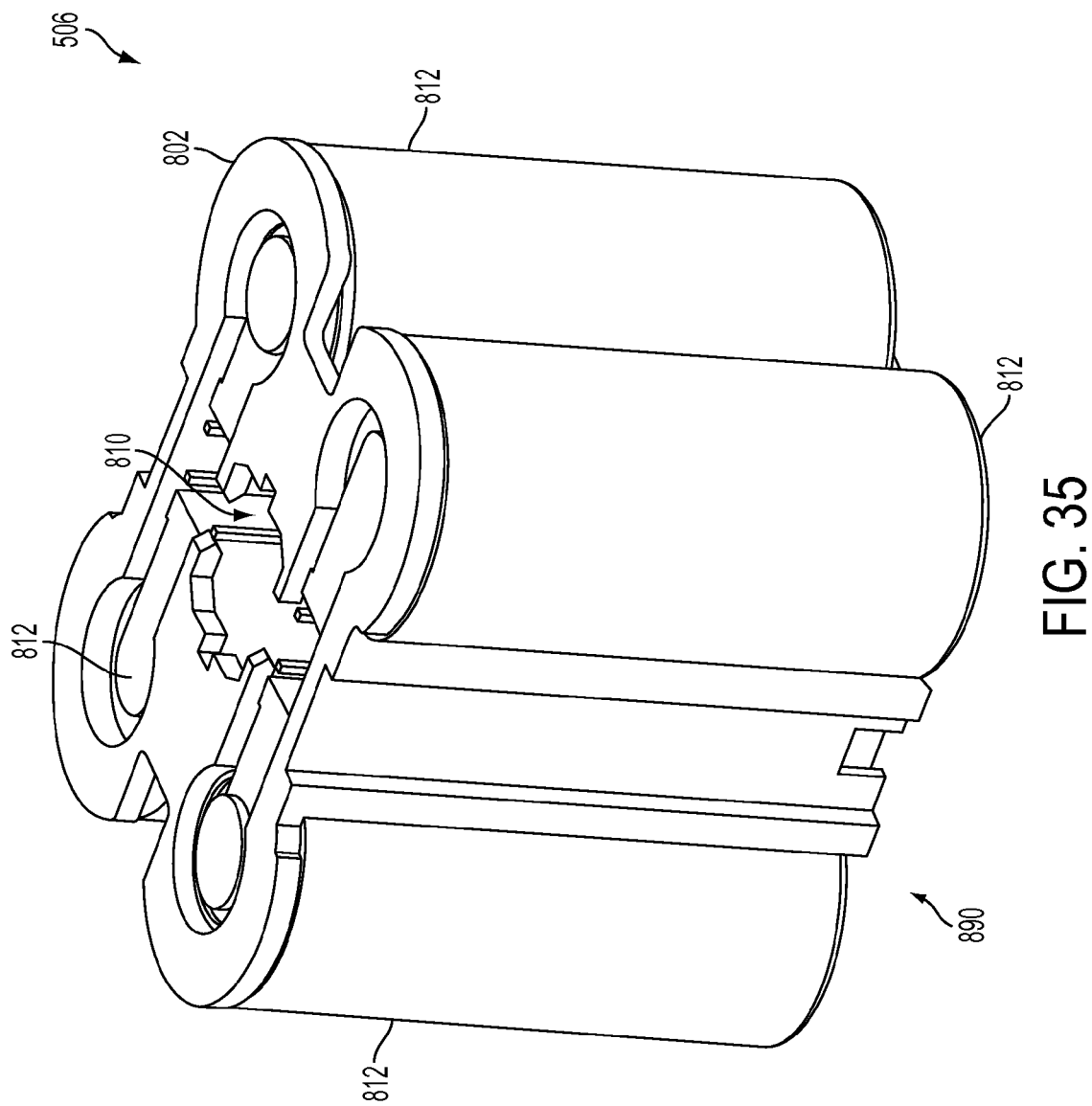
Figure 36:
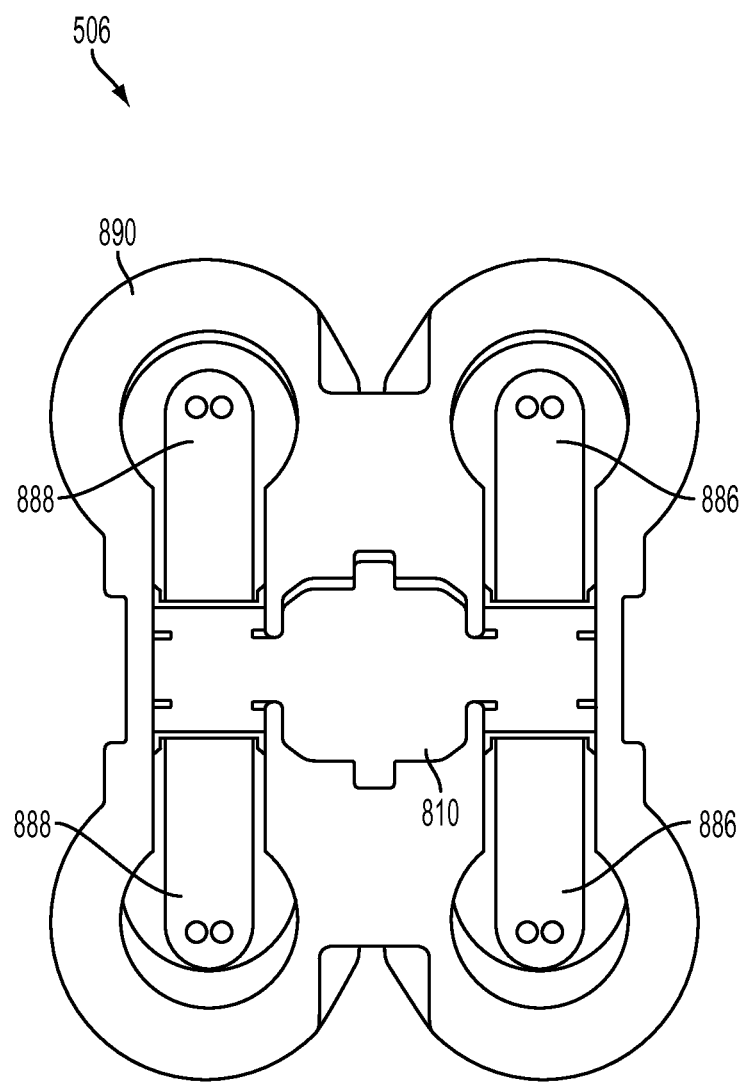
Figure 37:
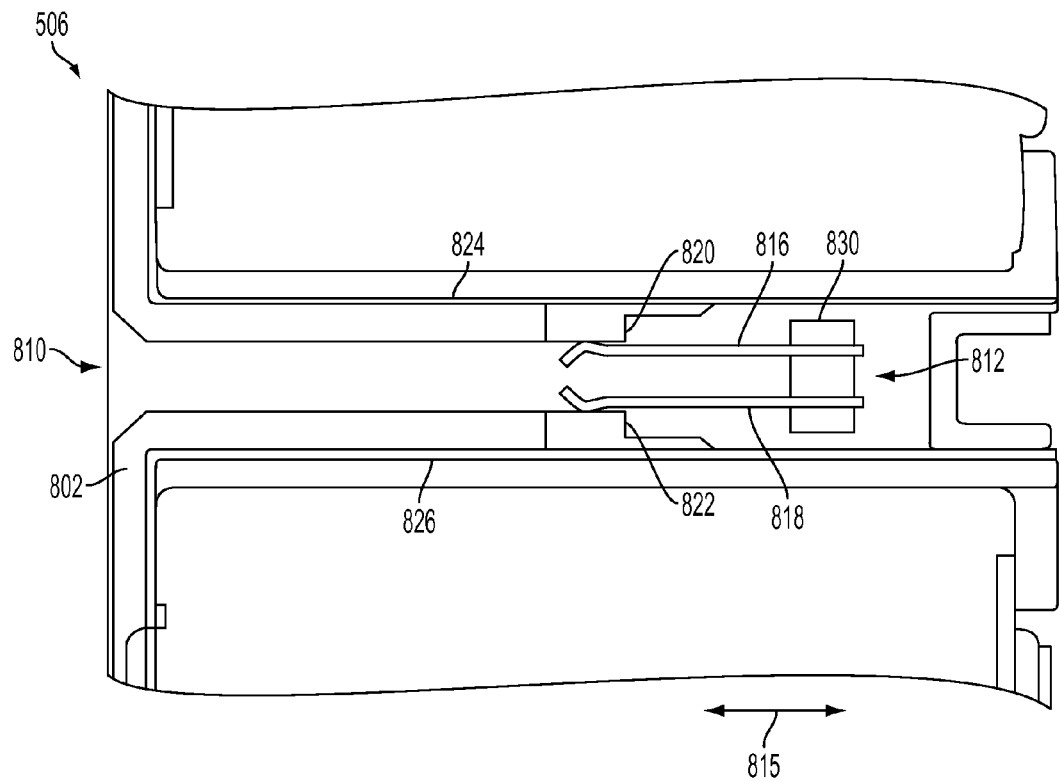
Figure 38:
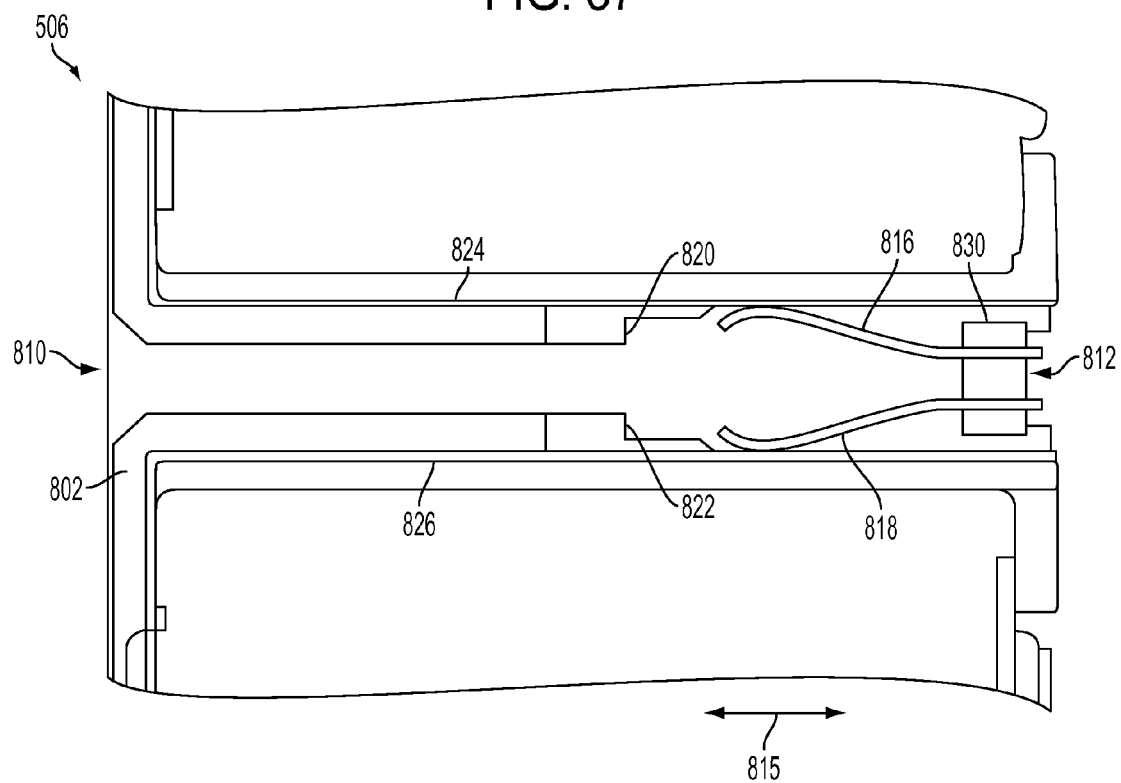
Figure 39:
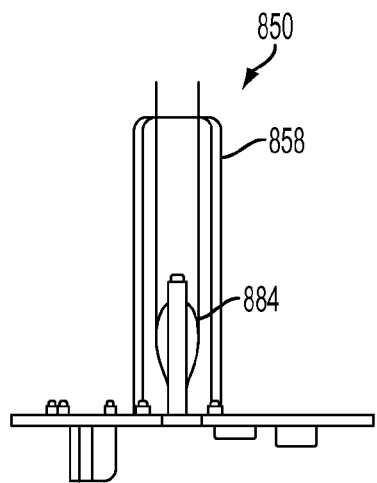
Figure 40:
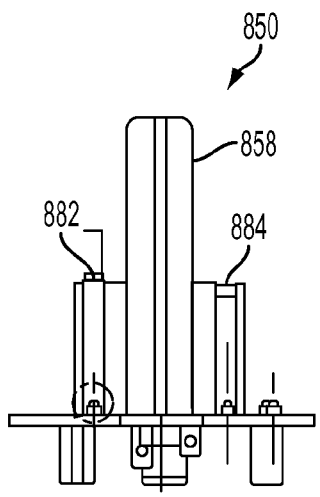
Figure 41:
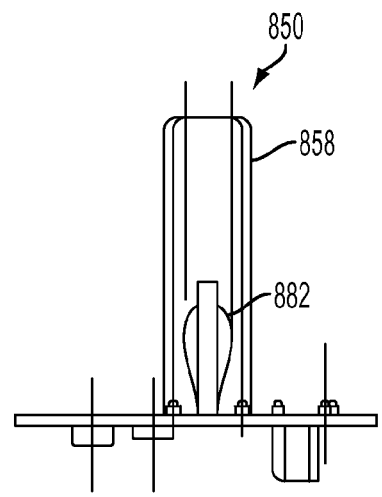
Figure 42:
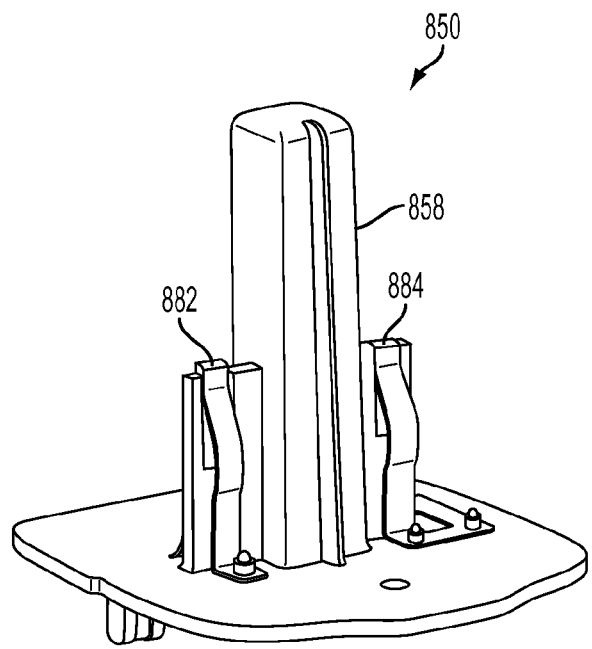

FIGS. 37 and 38 illustrate cross-sectional views of one embodiment of the battery unit of FIGS. 33-36 including a translatable drain.

FIGS. 39-42 show multiple views of one embodiment of a battery dock.

Figure 43:
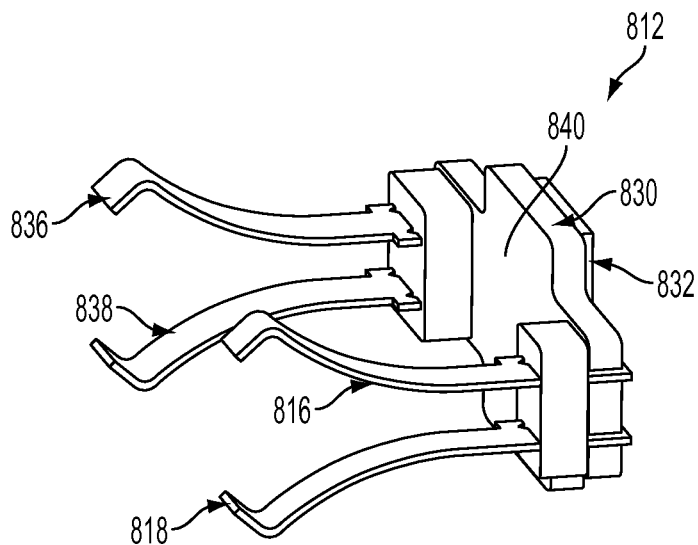

FIG. 43 is a perspective view of one embodiment of the translatable drain of FIGS. 37 and 38.

Figure 44:
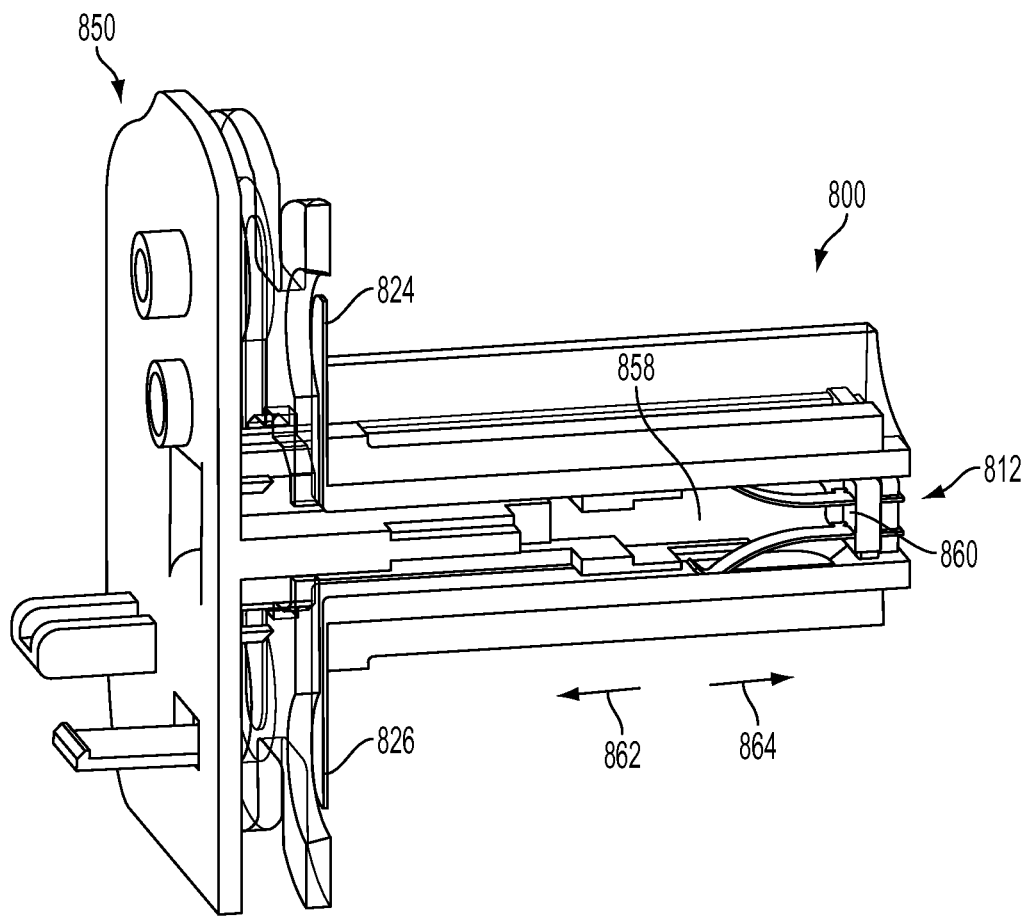

FIG. 44 illustrates one embodiment of the battery unit of FIGS. 33-36 attached to a battery dock with various components omitted for clarity.

Figure 45:
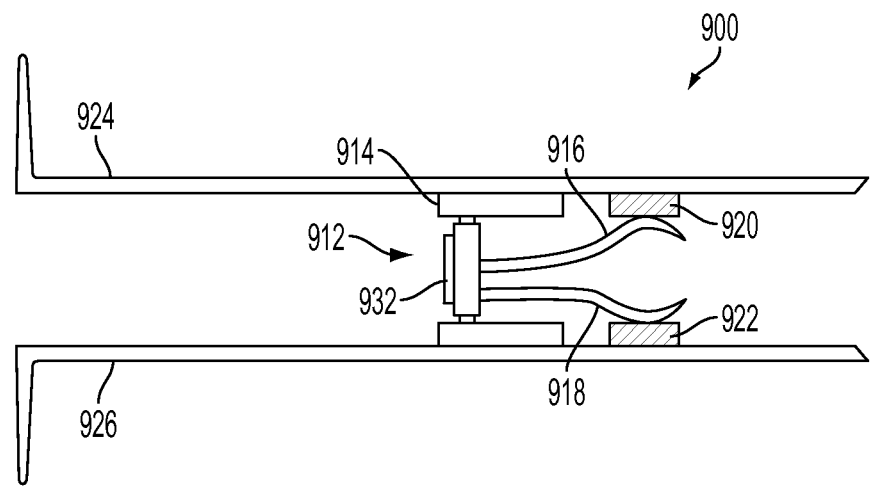
Figure 46:
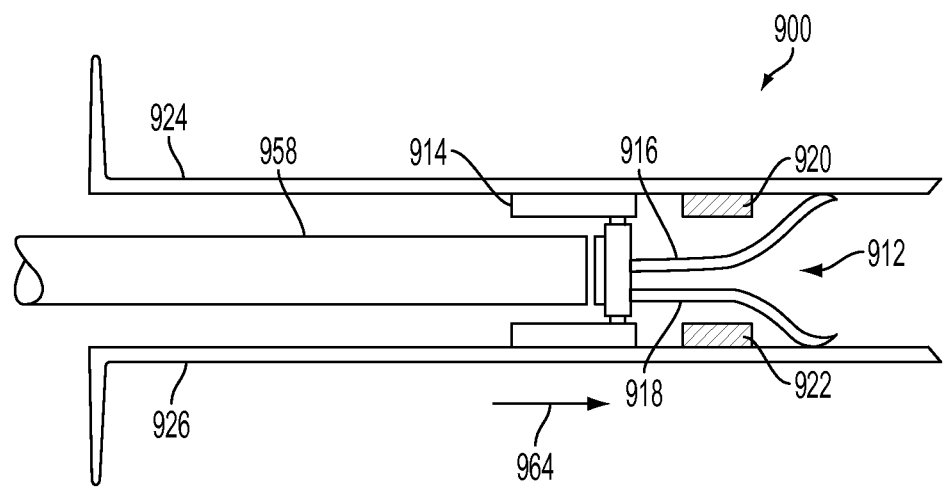

FIGS. 45 and 46 illustrate one embodiment of a battery unit with various components omitted for clarity.

Figure 47:
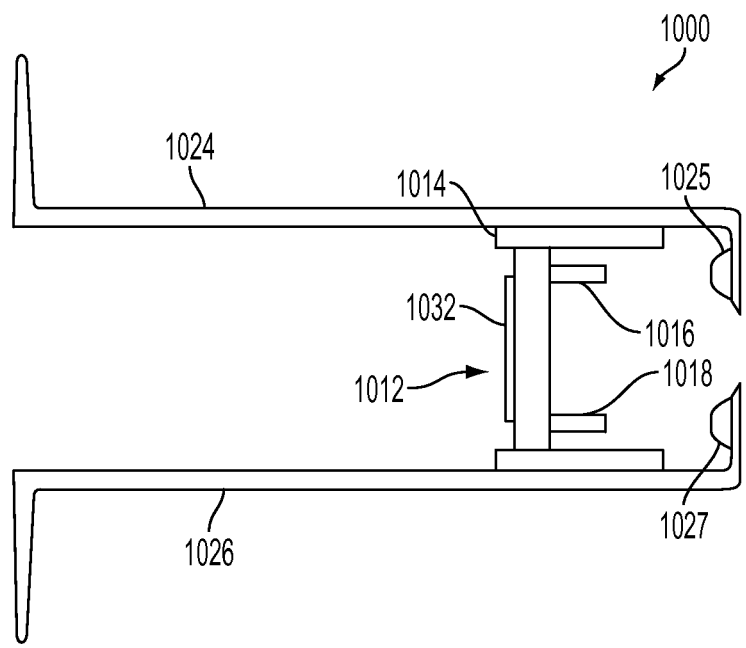
Figure 48:
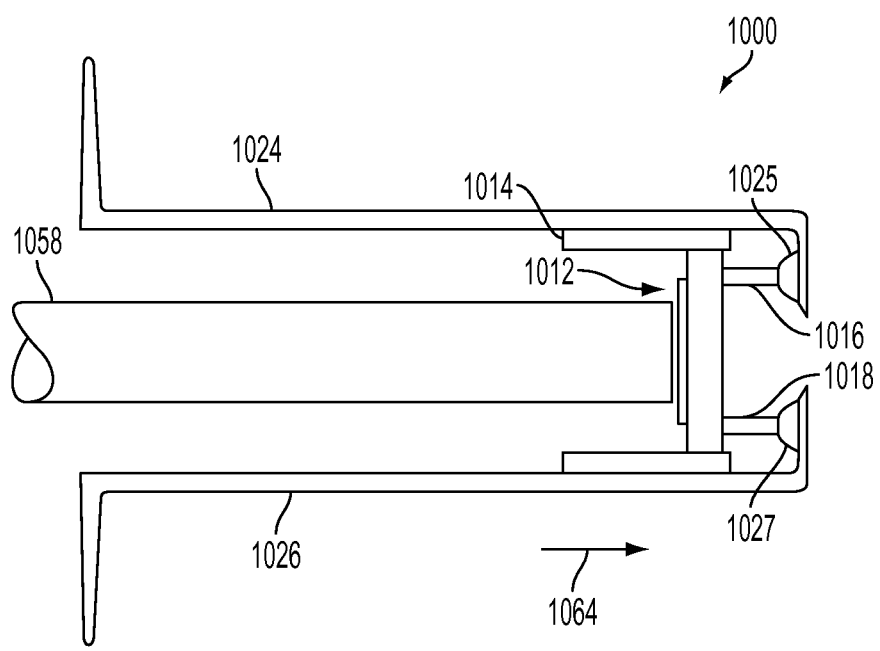

FIGS. 47 and 48 illustrate one embodiment of a battery unit with various components omitted for clarity.

Figure 49:
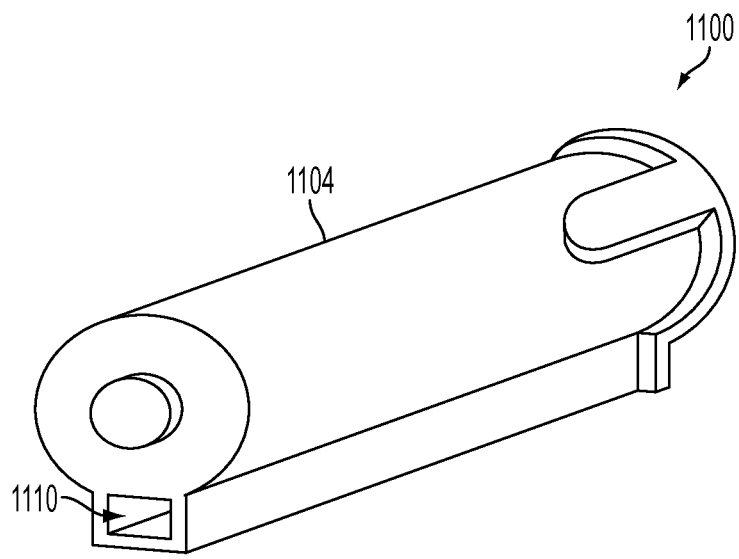

FIG. 49 is a perspective view of one embodiment of single cell battery unit.

Figure 50:
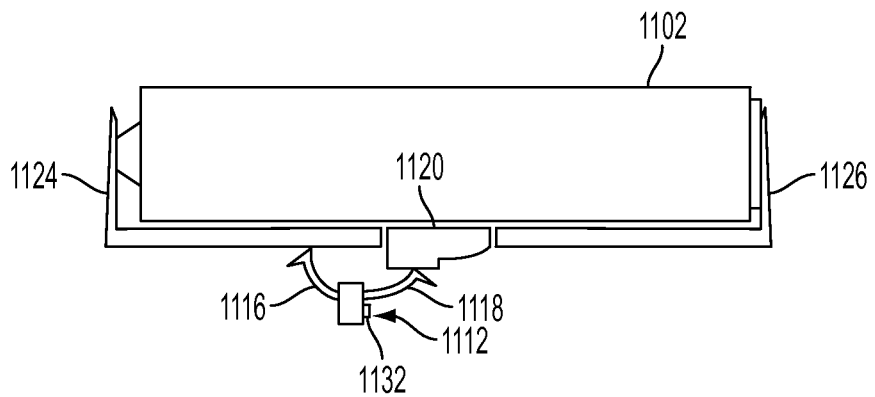
Figure 51:
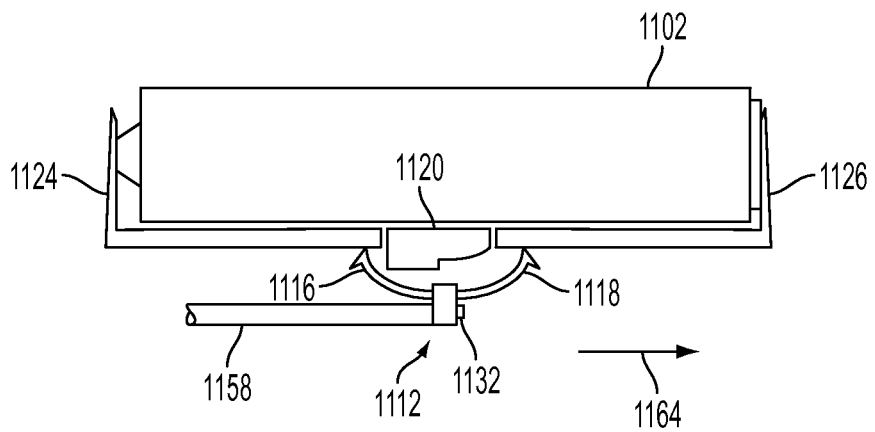

FIGS. 50 and 51 show internal views of the battery unit of FIG. 49 during various stages of operation with various components omitted for clarity.

Figure 52:
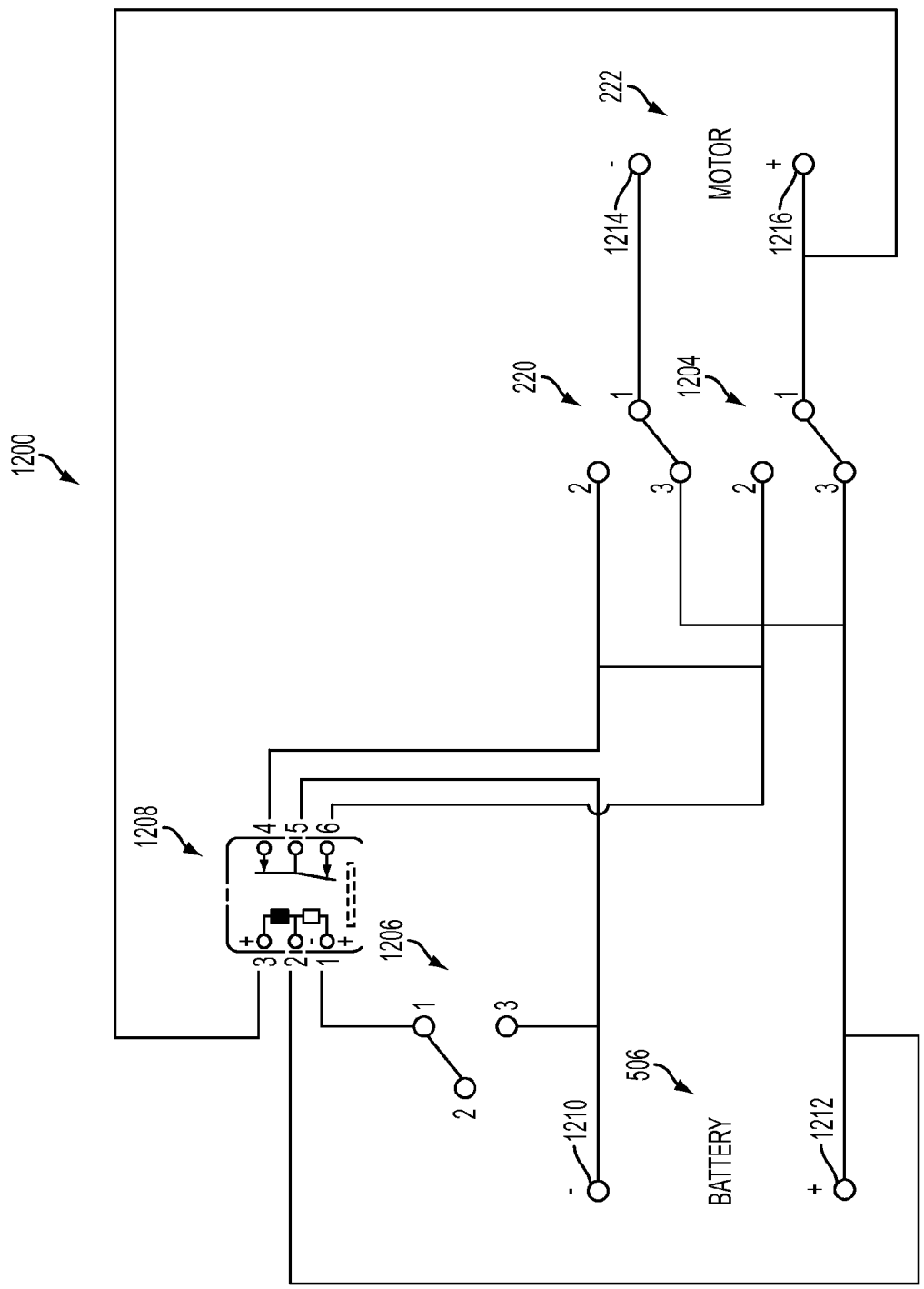

FIG. 52 illustrates one embodiment of a control circuit that may control a connection between the battery unit or other power supply and the motor or other drive device for firing the instrument of FIG. 1.

Figure 53:
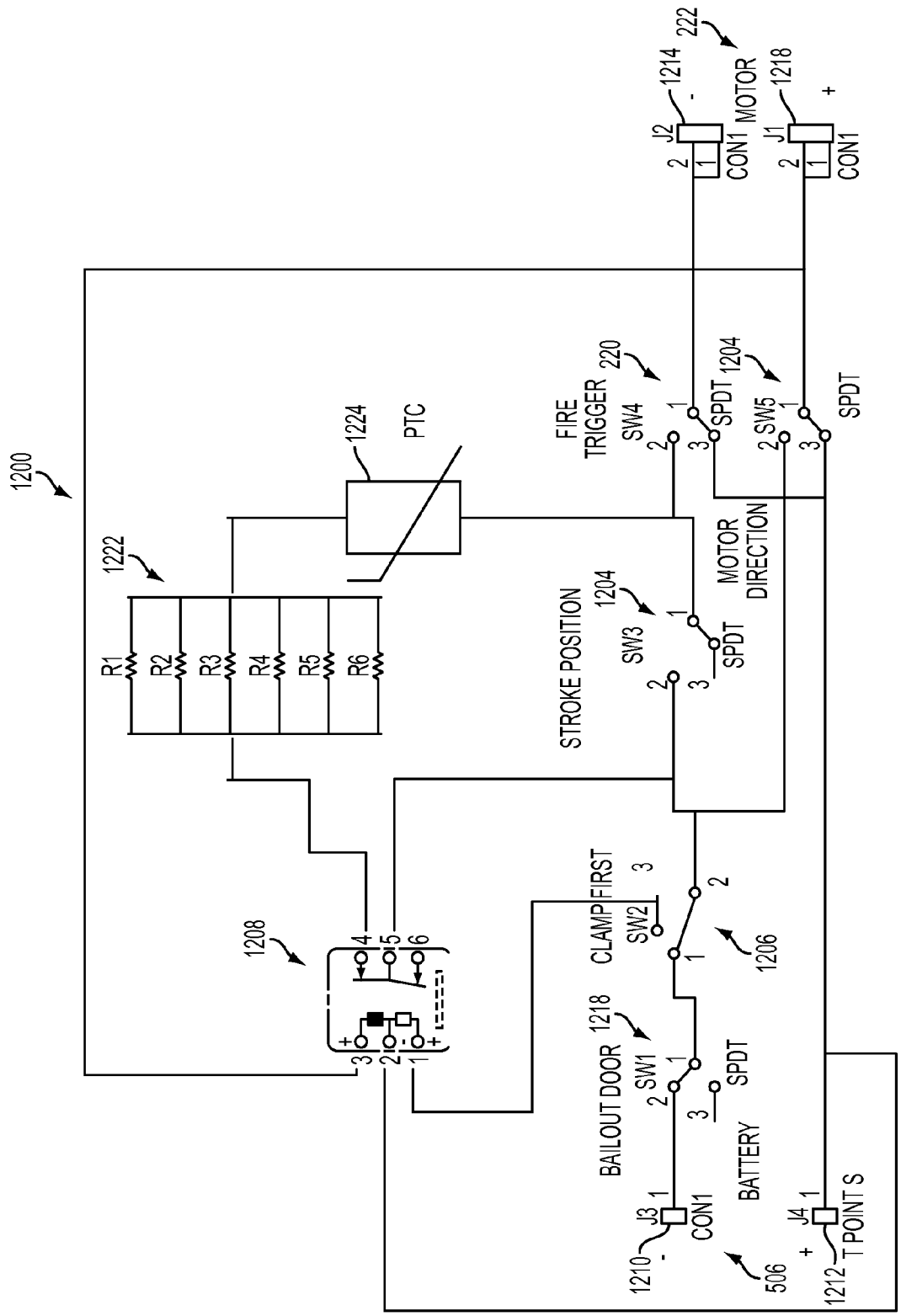

FIG. 53 illustrates one embodiment of the control circuit of FIG. 52 with additional switches and features.

Figure 54:
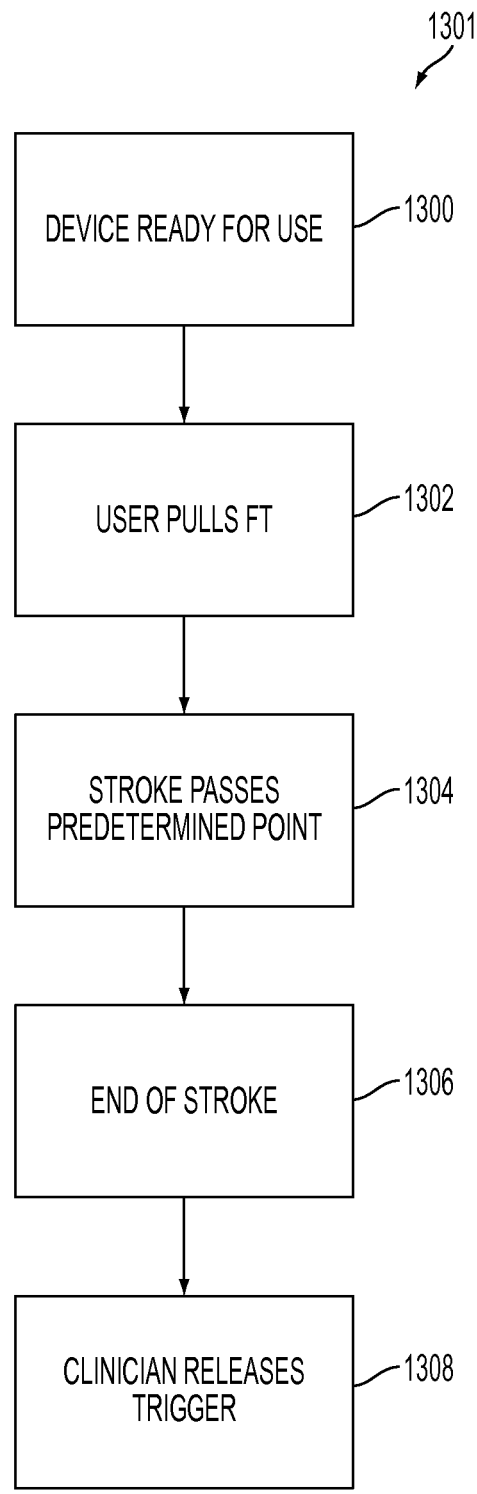

FIG. 54 is a flowchart showing one embodiment of a process flow showing the firing of the instrument of FIG. 1 utilizing the control circuit as illustrated in FIG. 53.

Figure 55:
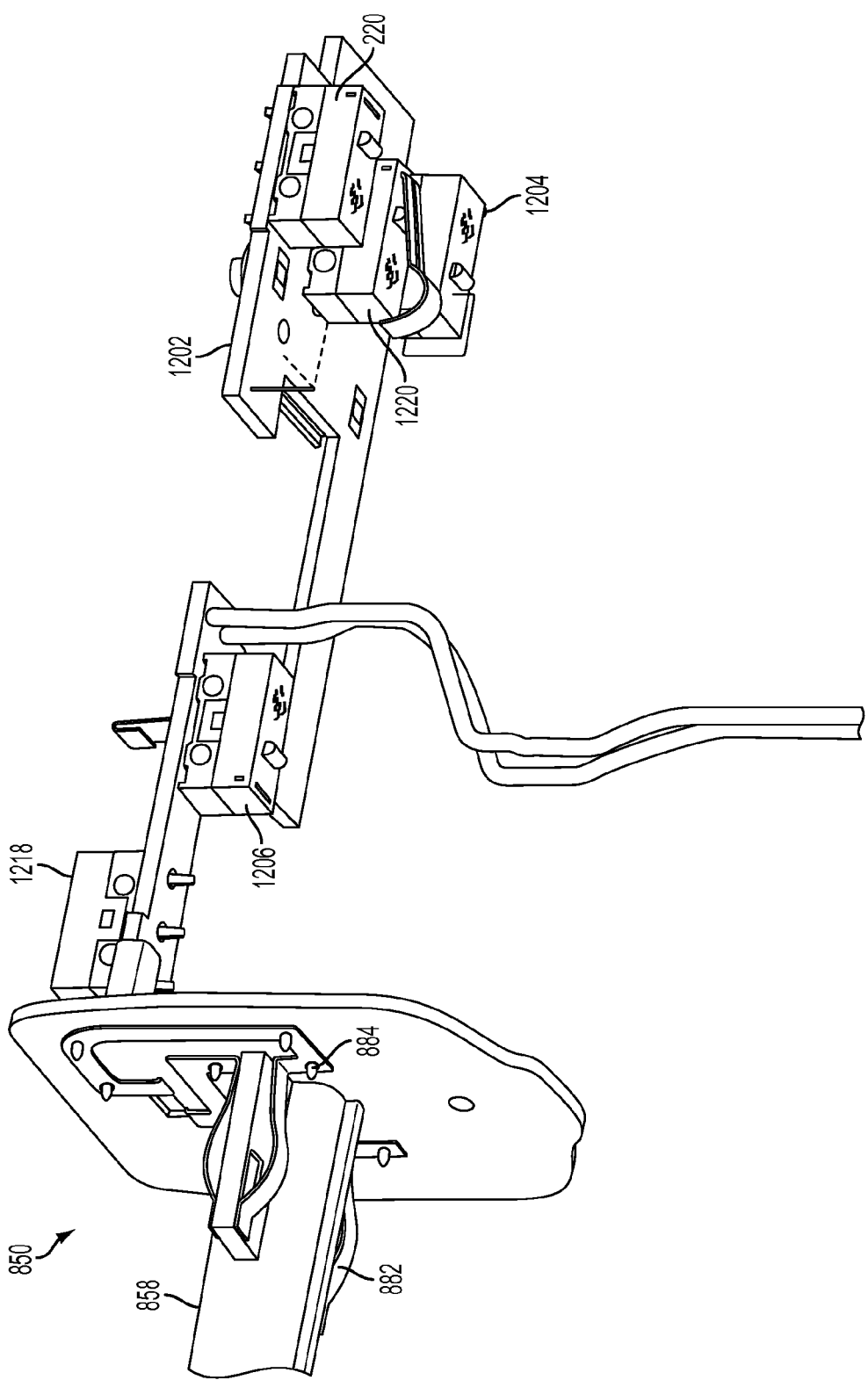

FIG. 55 illustrates a perspective view of one embodiment of circuit board for implementing the control circuit of FIG. 52 or 53, coupled to the battery dock of FIG. 36.

Figure 56:
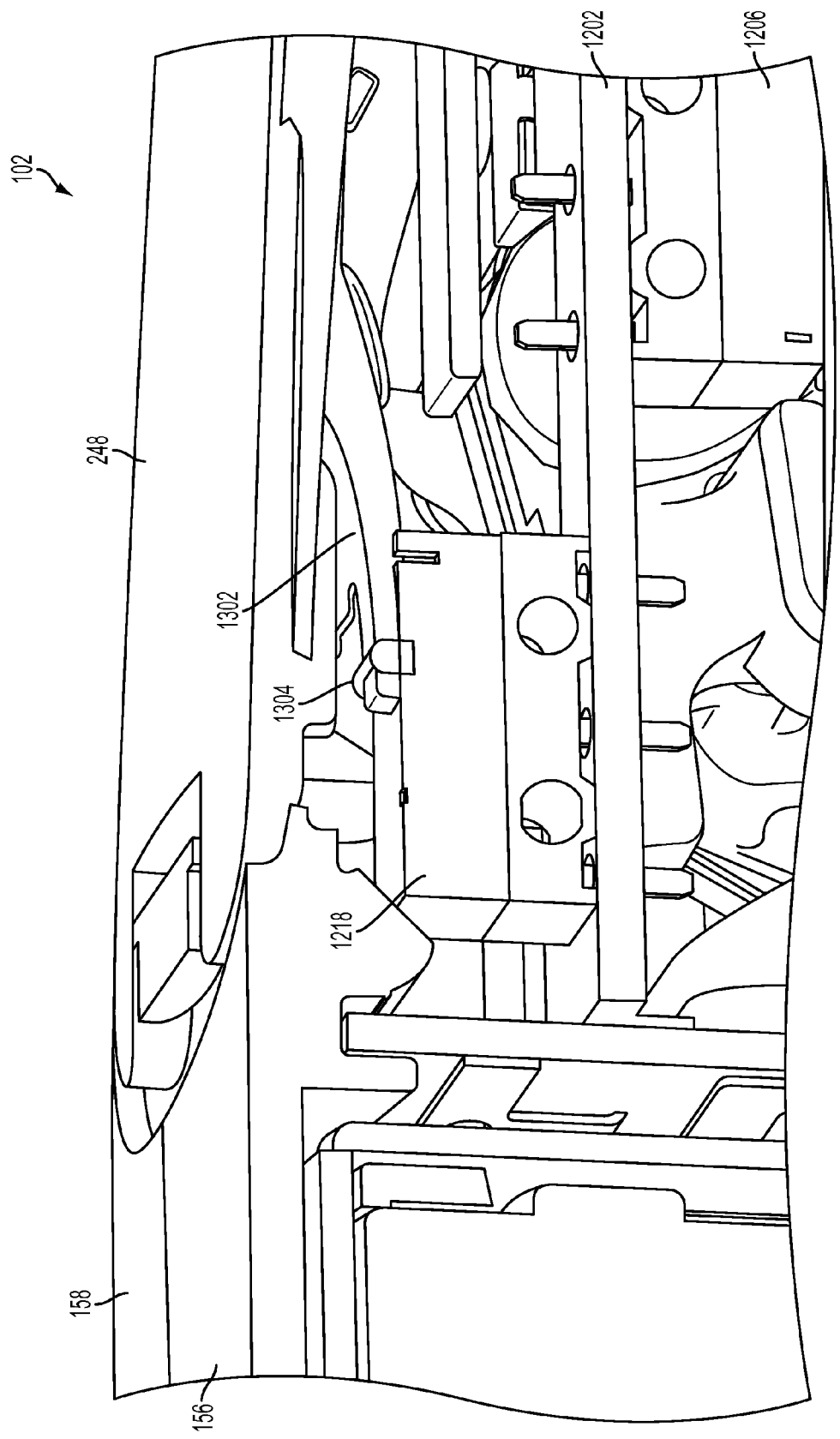

FIG. 56 illustrates a cut away view of one embodiment of the instrument of FIG. 1 showing the emergency access door switch.

Figure 57:
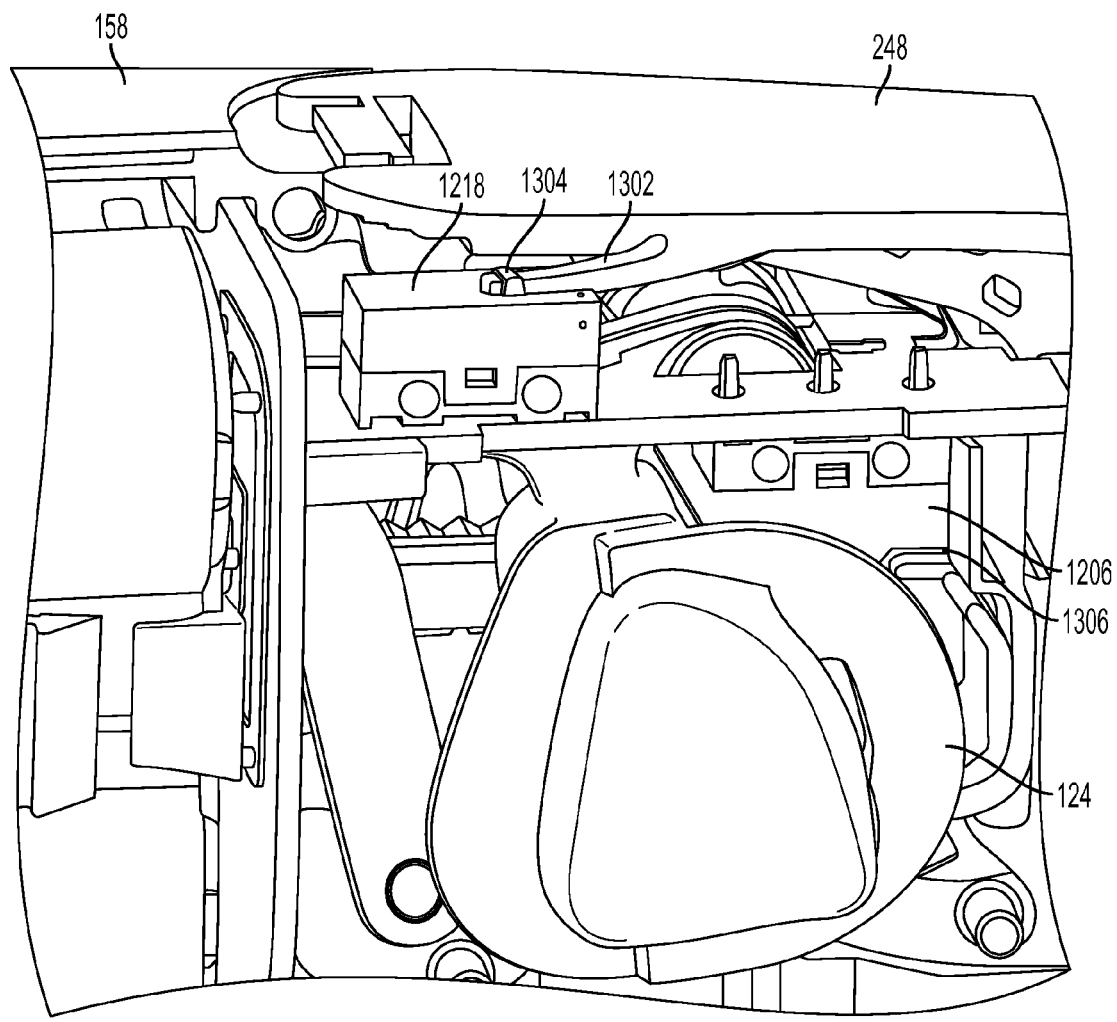

FIG. 57 illustrates another cut away view of one embodiment of the instrument of FIG. 1 showing the clamp switch.

Figure 58:
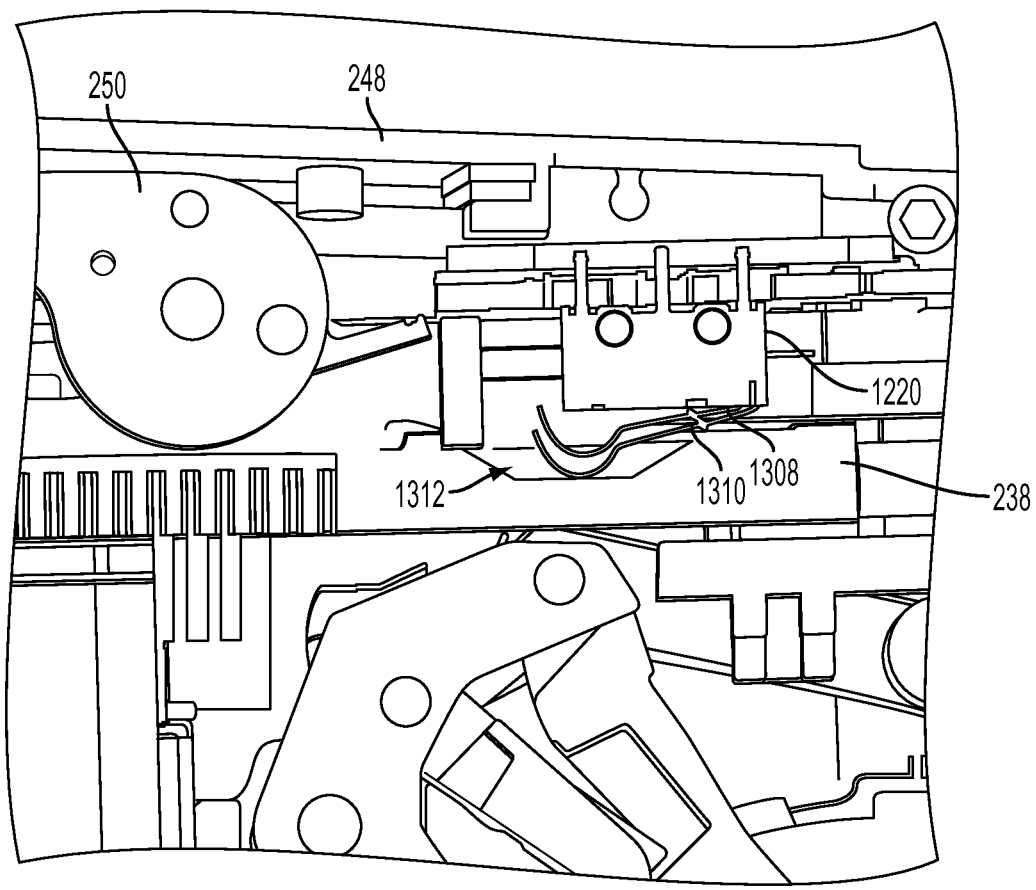

FIG. 58 illustrates another cut away view of one embodiment of the instrument of FIG. 1 showing the stroke position switch.

Figure 59:
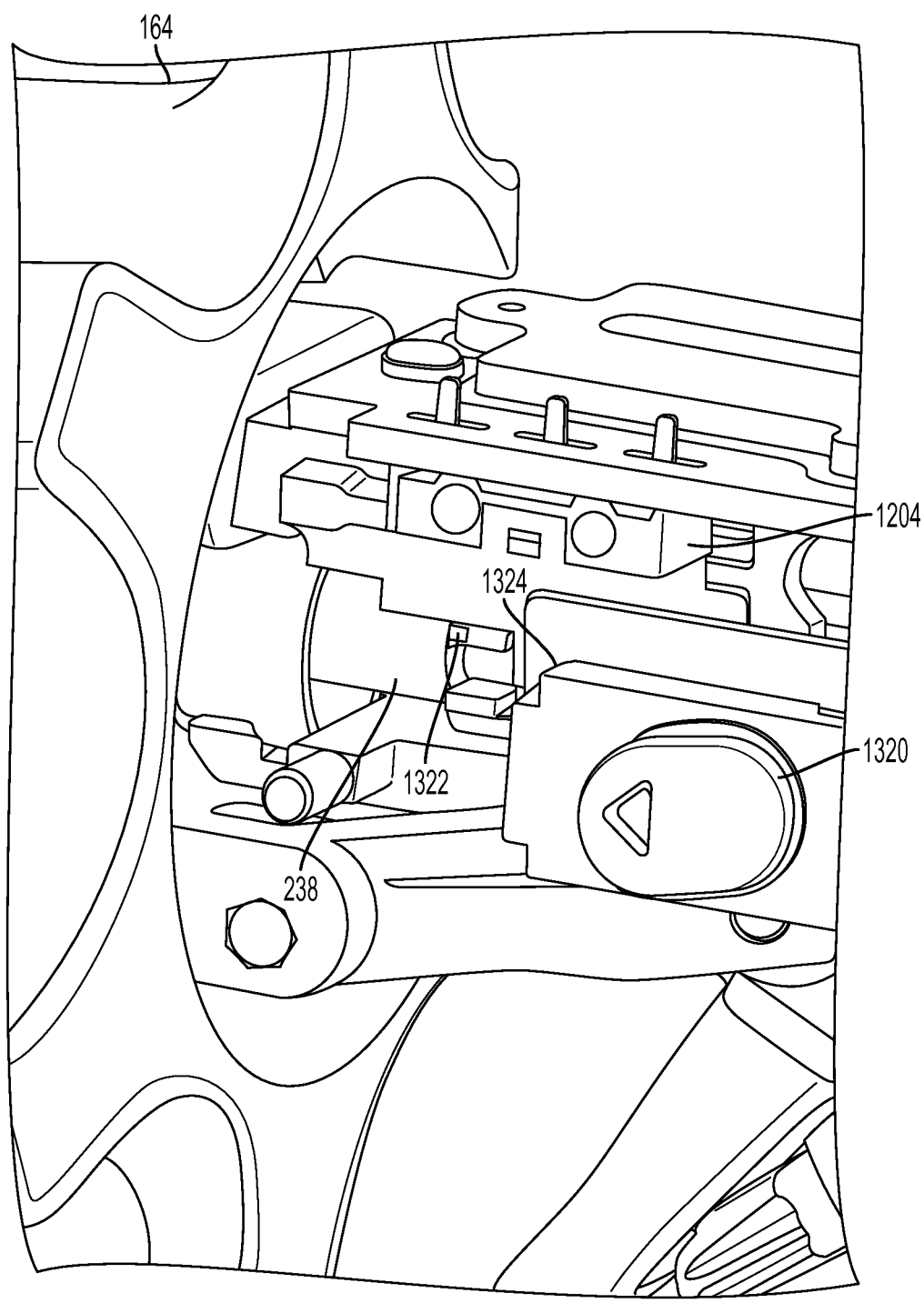

FIG. 59 illustrates another cut away view of one embodiment of the instrument of FIG. 1 showing the end-of-stroke/motor reverse switch.

DESCRIPTION

Various embodiments are directed to surgical instruments having control circuits for implementing an electronic lockout. For example, the control circuit may comprise one or more latching devices such as, for example, a latching relay, a transistor, etc. The surgical devices may comprise an end effector having first and second jaw members, where at least one of the jaw members is translatable (e.g., pivotally or otherwise) towards the other. The surgical instruments may also have a firing bar that is translatable through the end effector when the jaw members are closed (e.g., pivoted towards one another). The jaw members of the end effector may serve to clamp tissue. Once tissue is clamped, the firing bar may act upon the tissue. In various embodiments, distal motion of the firing bar may cause cutting and/or fastening of tissue. For example, the firing bar may define a cutting edge or knife to cut tissue clamped between the jaw members. Also, for example, the firing bar may drive a wedge or other mechanism to drive staples through the tissue clamped between the jaw members. According to various embodiments, the firing bar may be driven by a drive device such as, for example, an electric motor, a pneumatic or hydraulic device, etc. The drive device may be powered by a power supply such as, for example, a battery and/or a connection to an external source of electrical power, such as a wall outlet.

Figure 2:
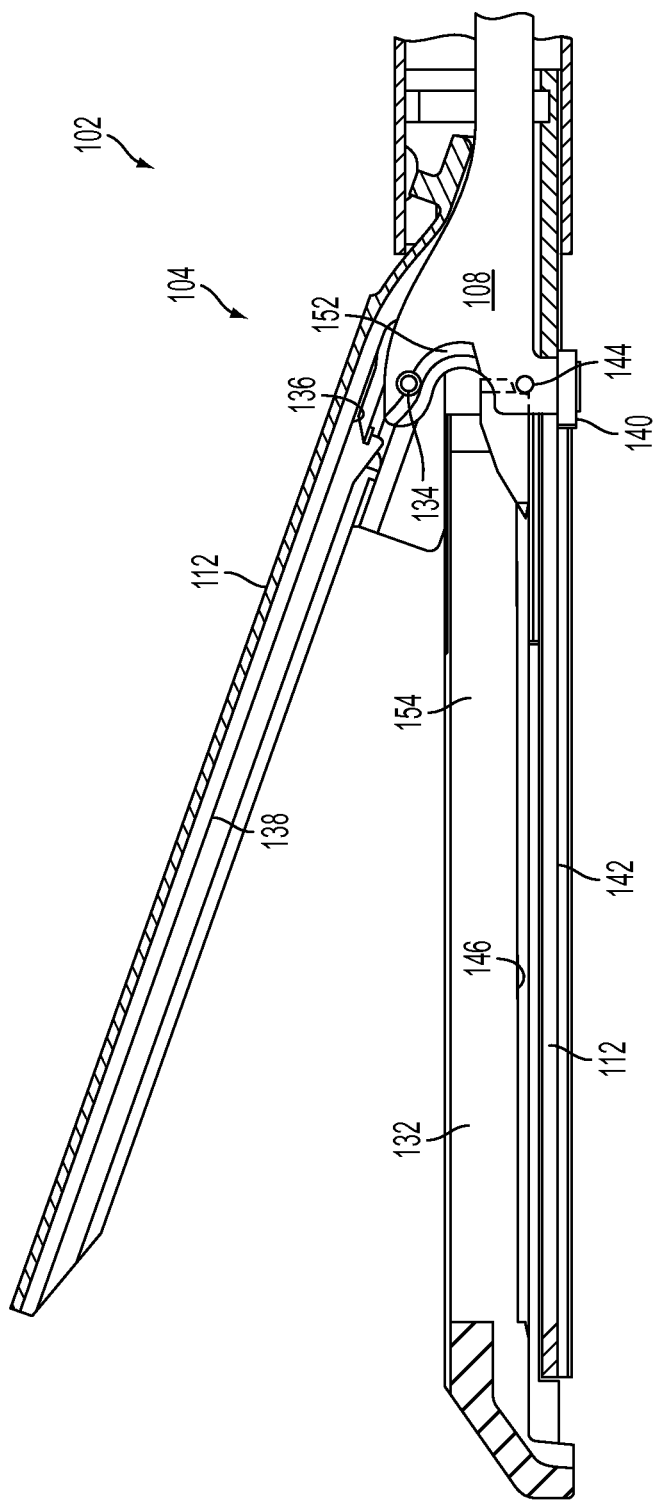
FIG. 2 shows one embodiment of an end effector of the instrument of FIG. 1.

FIG. 1 shows one embodiment of a surgical stapling and cutting instrument 102 with an electrically powered firing feature. The illustrated embodiment is an endoscopic instrument and, in general, the embodiments of the instrument 102 described herein are endoscopic surgical cutting and fastening instruments. It should be noted, however, that according to other embodiments, the instrument may be a non-endoscopic surgical cutting and fastening instrument, such as a laparoscopic or open surgical instrument. The instrument 102 may comprise an end effector 104 that may be operative to staple and cut tissue in response to control operations executed by a clinician grasping a handle portion 106. FIG. 2 shows one embodiment of the end effector 104 of the instrument 102. According to various embodiments, the instrument 102 may utilize an E-beam firing mechanism or firing bar 108 that may control the spacing of the end effector 104. For example, a first jaw member, or elongate channel 110 and a pivotally translatable second jaw member or anvil 112 may be maintained at a spacing that assures effective stapling and severing.

The instrument 102 may comprise the handle portion 106 and an implement portion 114. The implement portion 114 may be connected to the handle portion 106 and may comprise a shaft 116 distally terminating in the end effector 104. The handle portion 106 may comprise a pistol grip 118. A closure trigger 120 may be positioned such that a clinician may pivotally draw the closure trigger 120 towards the pistol grip 118 to cause clamping, or closing, of the anvil 112 toward the elongate channel 110 of the end effector 104. A firing trigger 122 may be positioned farther outboard of the closure trigger 120 and may be pivotally drawn by the clinician to cause the stapling and severing of clamped tissue in the end effector 104. As described below, the stapling and severing of the clamped tissue by the end effector 104 may be powered by an electric motor.

It will be appreciated that the terms "proximal" and "distal" are used herein with reference to a clinician gripping a handle of an instrument. Thus, the end effector 104 is distal with respect to the more proximal handle portion 106. It will be further appreciated that for convenience and clarity, spatial terms such as "vertical" and "horizontal" are used herein with respect to the drawings. However, surgical instruments are used in many orientations and positions, and these terms are not intended to be limiting and absolute.

In use, the clinician may actuate the closure trigger 120 first. For example, once the clinician is satisfied with the positioning of the end effector 104, the clinician may draw back the closure trigger 120 to its fully closed, locked position proximate to the pistol grip 118. Then, the clinician may actuate the firing trigger 122 to initiate powered cutting and stapling of tissue held between the anvil 112 and elongate channel 110. For example, the firing bar 108 may be powered forward to cut tissue and drive staples, for example, as described herein below. When the clinician removes pressure from the firing trigger 122, the firing bar 108 may be returned to the pre-firing position shown in FIG. 2. The clinician may actuate a release button 124 on the handle portion 106 to release the closure trigger 120. The clinician may then release the closure trigger, in turn releasing the anvil 112 and elongate channel 110 to pivot away from one another back to the position shown in FIG. 2.

Referring again to FIG. 1, the shaft 116 may comprise a frame 126 enclosed by a closure sleeve 128. A firing drive member 130 may be positioned within the frame 126 and may extend from the handle portion 106 to the firing bar 108. The drive member 130 may comprise a single component, or may be made up of multiple components. The frame 126 may connect the handle portion 106 to the end effector 104. With the closure sleeve 128 withdrawn proximally by the closure trigger 120 as depicted in FIGS. 1 and 2, the anvil 112 may springedly open, pivoting away from the elongate channel 110 and translating proximally with the closure sleeve 128.

The elongate channel 110 may receive a staple cartridge 132 that may be responsive to the firing bar 108 to drive staples into forming contact with the anvil 112. It will be appreciated that although a readily replaceable staple cartridge 132 is advantageously described herein, a staple cartridge 132 consistent with various embodiments may be permanently affixed or integral to the elongate channel 110, for instance when a larger portion of the end effector 104 is replaced after each firing.

Figure 3:
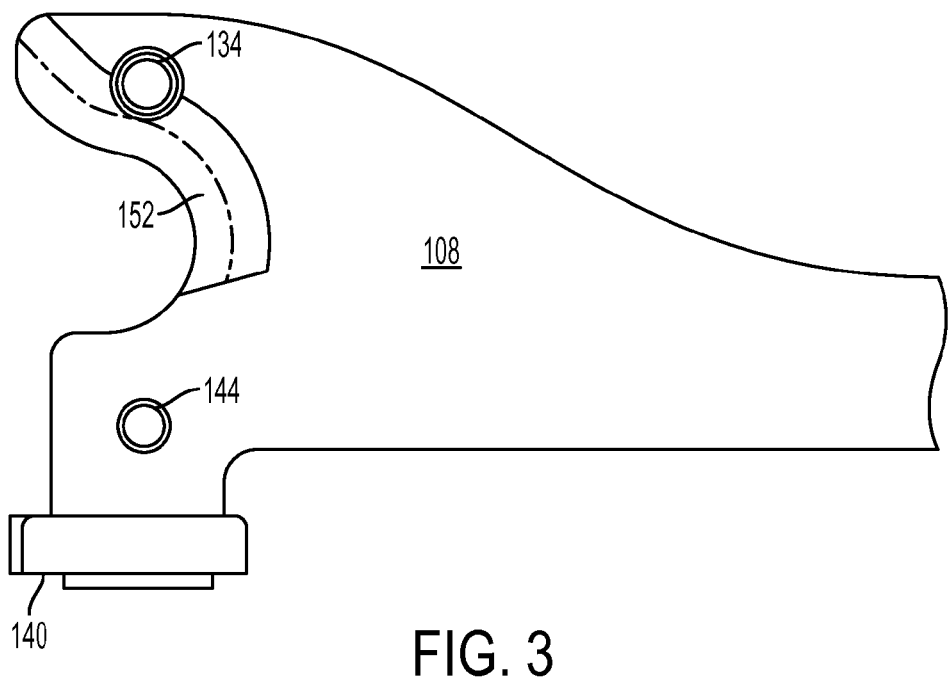
FIGS. 3 and 4 show additional views of one embodiment of a firing bar of the instrument of FIG. 1.
Figure 4:
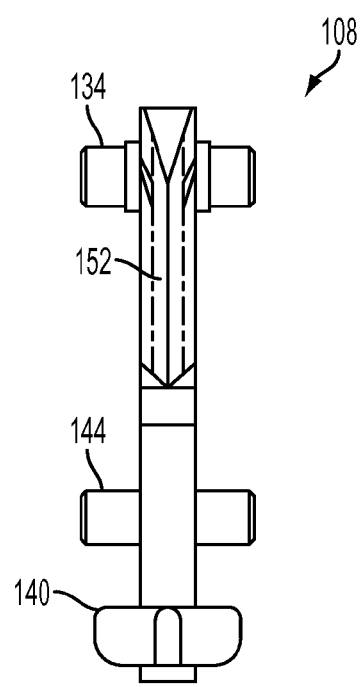

FIGS. 3 and 4 show additional views of one embodiment of the firing bar 108. As illustrated in FIGS. 2-4, the firing bar 108 may include three vertically spaced pins that control the spacing of the end effector 104 during firing. An upper pin 134 may be staged to enter an anvil pocket 136 near the pivot between the anvil 112 and elongate channel 110. When fired with the anvil 112 closed, the upper pin 134 may advance distally within a longitudinal anvil slot 138 extending distally through anvil 112. According to various embodiments, minor upward deflections of the anvil 112 may be overcome by a downward force imparted on the anvil 112 by the upper pin 134. The firing bar 108 may also include a lower pin, or firing bar cap, 140 that may upwardly engage a channel slot 142 in the elongate channel 110, thereby cooperating with the upper pin 134 to draw the anvil 112 and the elongate channel 110 together in the event of excess tissue clamped therebetween.

Figure 5:
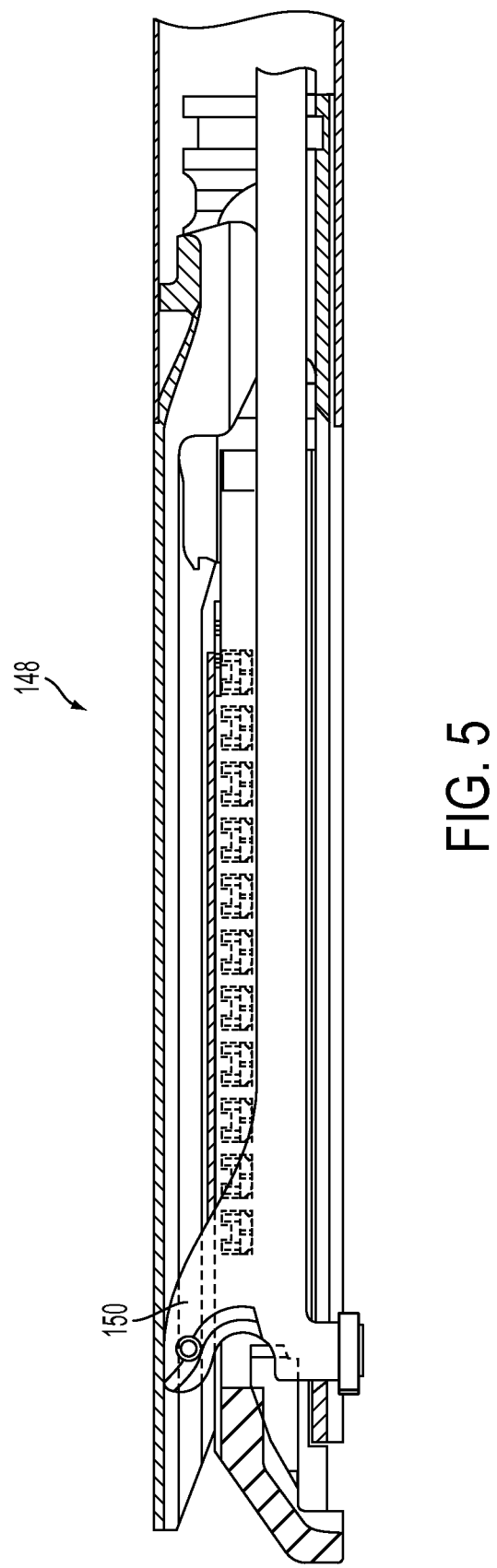
FIG. 5 illustrates an alternative embodiment of an end effector having a firing bar lacking a middle pin.

The firing bar 108 may also comprise a middle pin 144 that may pass through a firing drive slot 146 formed in a lower surface of the cartridge 132 and an upward surface of the elongate channel 110. In this way, the middle pin 144 may initiate the driving of the staples, as described below. The middle pin 144, by sliding against the elongate channel 110, may resist a tendency for the end effector 104 to be pinched shut at its distal end. To illustrate an advantage of the middle pin 144, FIG. 5 illustrates an alternative embodiment of an end effector 148 having a firing bar 150 lacking a middle pin. As shown in FIG. 5, the end effector 148 is allowed to pinch shut at its distal end, which may tend to impair desired staple formation.

Returning to FIGS. 2-4, the firing bar 108 may comprise a distally presented cutting edge 152 between the upper and middle pins 134, 144. When the end effector 104 is fired, the cutting edge 152 may traverse through a proximally presented, vertical slot 154 in the cartridge 132 to sever clamped tissue present between the anvil 112 and the elongate channel 110. The affirmative positioning of the firing bar 108 with regard to the elongate channel 110 and anvil 112 may make it more likely that an effective cut is performed.

The affirmative vertical spacing provided by the E-Beam firing bar 108 may be suitable for the limited size available for endoscopic devices. Moreover, the E-Beam firing bar 108 may enable fabrication of an anvil 112 with a camber imparting a vertical deflection at its distal end, similar to the position depicted in FIG. 5. This cambered anvil 112 may assist in achieving a desirable gap in the end effector 104 even with an anvil 112 having reduced thickness, which may be thus more suited to the size limitations of an endoscopic device. The E-Beam firing bar 108 may further enable increased applications, especially in combination with a range of configurations of staple cartridges. For instance, a clinician may select a gray staple cartridge yielding a 0.02 mm tissue gap, a white staple cartridge yielding a 0.04 mm tissue gap, a blue cartridge yielding a 0.06 mm tissue gap, or a green cartridge yielding a 0.102 mm tissue gap. The vertical height of each respective staple cartridge in combination with the length of staples and an integral wedge sled (described in more detail below) may predetermine this desired tissue thickness with the anvil 112 appropriately vertically spaced by the E-Beam firing bar 108.

Figure 6:
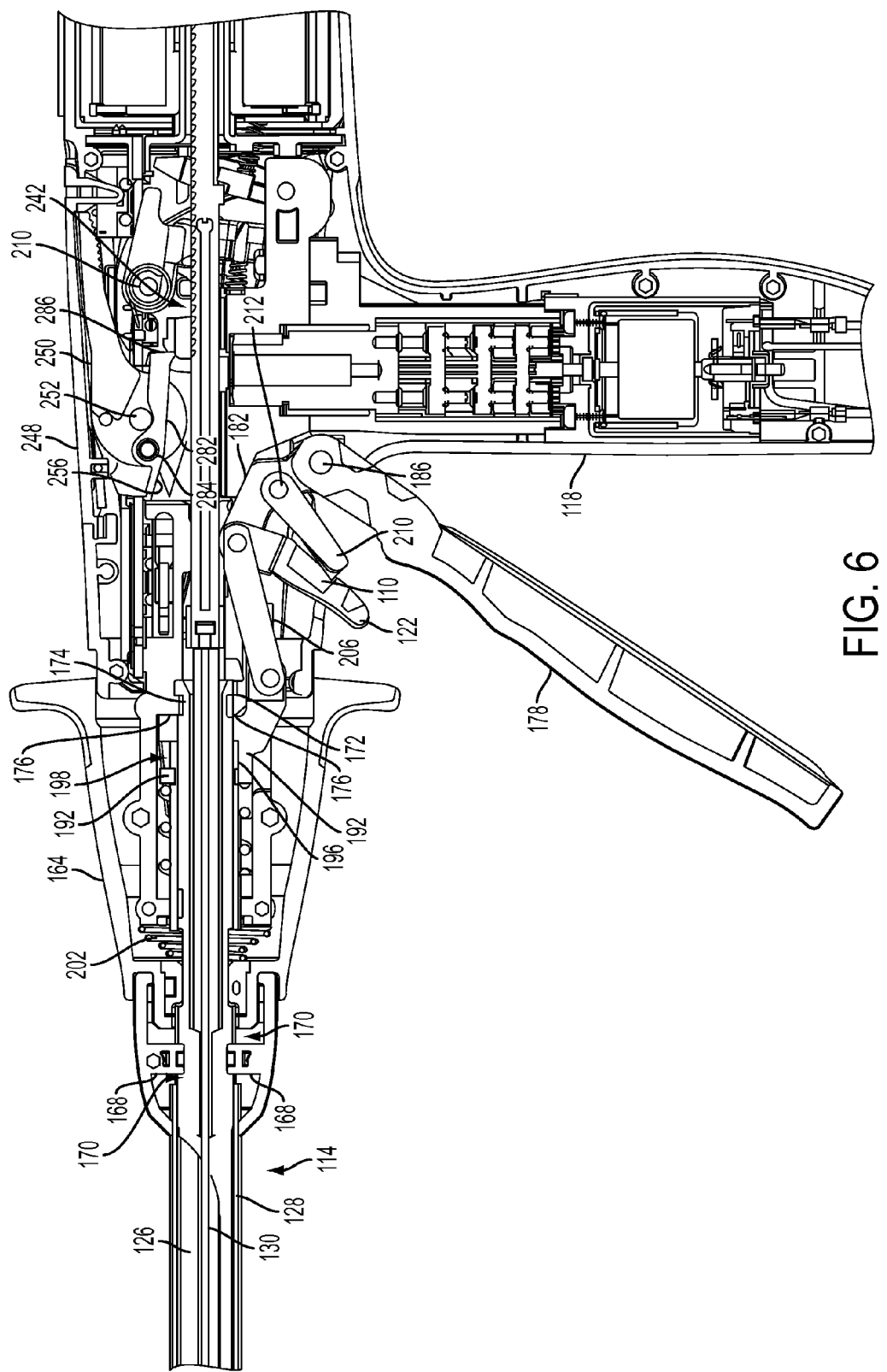
FIG. 6 illustrates a cut-away side view of one embodiment of the surgical instrument of FIG. 1.
Figure 7:
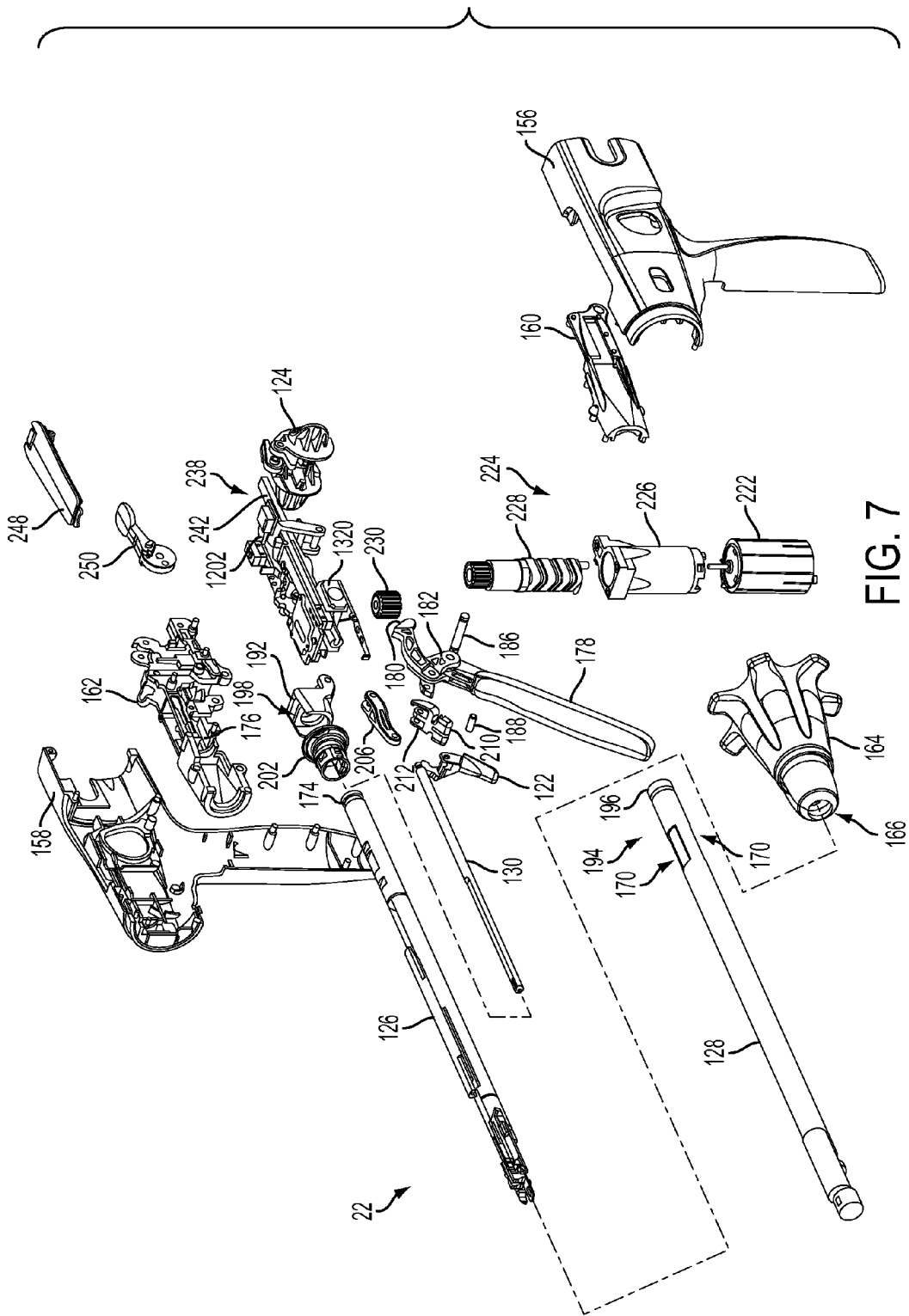
FIG. 7 illustrates an exploded view of one embodiment of the surgical instrument showing various components thereof.
Figure 8:
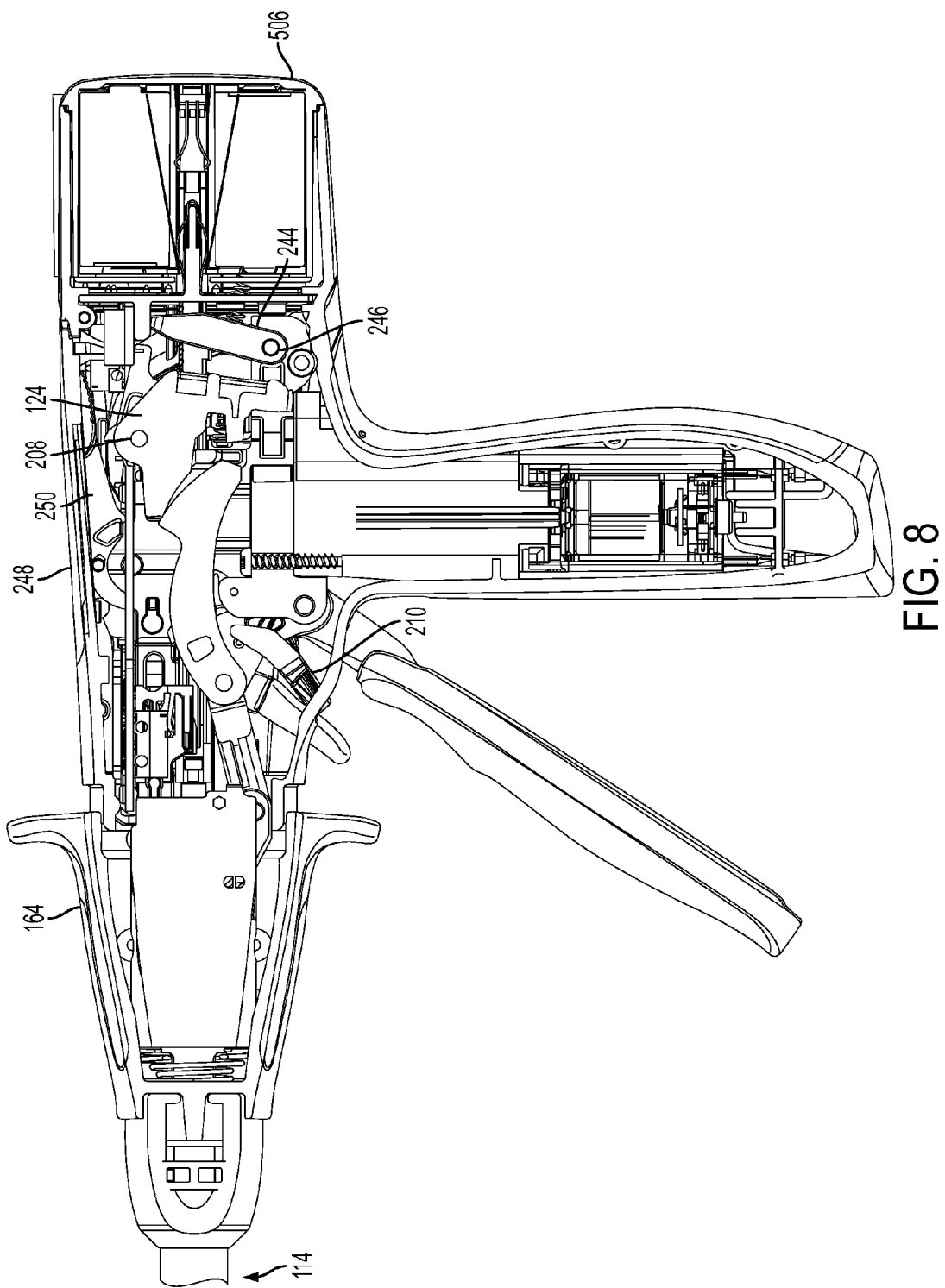
FIG. 8 illustrates a shallower cut-away side view of one embodiment of the surgical instrument of FIG. 1 to show component features not shown in the cut-away side view of FIG. 6.
Figure 9:
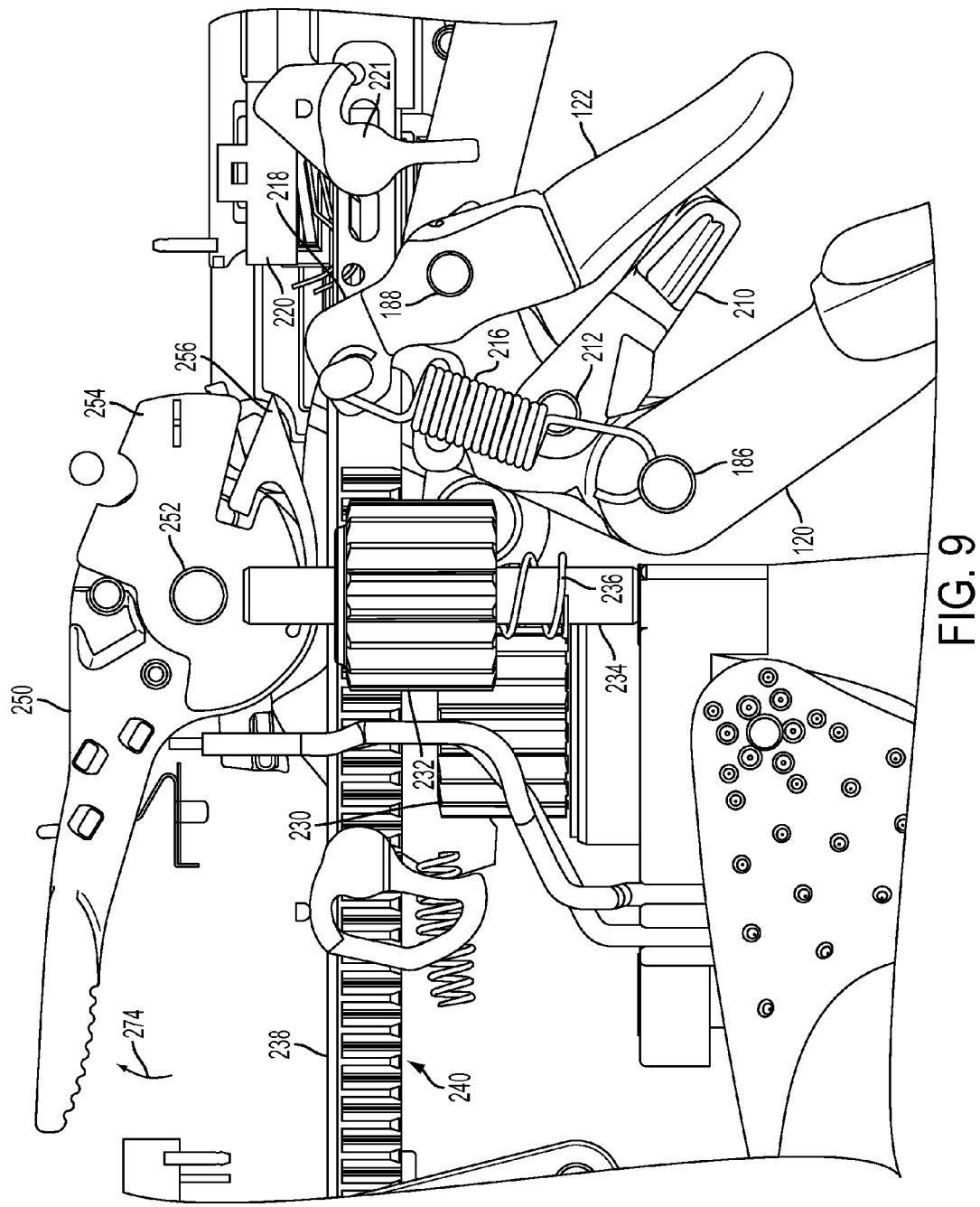
FIG. 9 illustrates an internal view of one embodiment of the surgical instrument of FIG. 1.

FIGS. 6-9 illustrate various internal components of the handle portion 106 of one embodiment of the surgical instrument 102. For example, FIG. 6 illustrates a cut-away side view of one embodiment of the surgical instrument 102. FIG. 7 illustrates an exploded view of one embodiment of the surgical instrument 102 showing a portion of the components thereof. FIG. 8 illustrates a cut-away side view of one embodiment of the surgical instrument of 102 that is shallower than the cut-away of FIG. 6 in order to show component features not shown in the cut-away side view of FIG. 6. FIG. 9 illustrates an internal view of one embodiment of the surgical instrument 102.

With reference to FIGS. 6-9, the handle portion 106 may be comprised of first and second base sections 156 and 158, which may be molded from a polymeric material such as a glass-filled polycarbonate. Within the first and second base sections 156, 158 may be first and second frame sections 160, 162. A rotating knob 164 may have a bore 166 extending completely through it for engaging and rotating the implement portion 114 about its longitudinal axis. The rotating knob 164 may includes an inwardly protruding boss 168 extending along at least a portion of the bore 166. The protruding boss 168 is received within a longitudinal slot 170 formed at a proximal portion of the closure sleeve 128 such that rotation of the rotating knob 164 effects rotation of the closure sleeve 128. It will be appreciated that the boss 168 may further extend through frame 126 and into contact with a portion of the firing drive member 130 to effect its rotation as well. Thus, the end effector 104 may rotate with the rotating knob 164.

A proximal end 172 of the frame 126 may pass proximally through the rotating knob 164 and may be provided with a circumferential notch 174 that is engaged by opposing channel securement members 176 extending respectively from the frame sections 160 and 162. The channel securement members 176 extending from the frame sections 160, 162 may serve to secure the frame 126 to the handle portion 106 such that the frame 126 does not move longitudinally relative to the handle portion 106.

The closure trigger 120 may have a handle section 178, a lever section 180, and an intermediate section 182. A bore 184 may extend through the intermediate section 182. A cylindrical support member 186 may pass through the bore 184 for pivotably mounting the closure trigger 120 on the handle portion 106 (e.g., via the frame sections 160, 162). A second cylindrical support member 188 may pass through a bore 190 of firing trigger 122 for pivotally mounting the firing trigger 122 on the handle portion 106.

A closure yoke 192 may be housed within the handle portion 106 for reciprocating movement therein and serves to transfer motion from the closure trigger 120 to the closure sleeve 128. The closure yoke 192 may be coupled to the handle portion 106 via the respective frame portions 160, 162. A proximal end 194 of the closure sleeve 128 is provided with a flange 196 that is snap-fitted into a receiving recess 198 formed in the yoke 192. A distal end of the yoke 192 may be coupled to a secondary yoke 200 via a biasing member such as a spring 202. A proximal end of the yoke 192 may define a bore 204 for receiving a linkage 206. A proximal end of the linkage 206 may be coupled to the closure trigger 120. For example, the linkage 206 may comprise a bore for receiving the pin 188. In this way, when the clinician moves the handle section 178 of the closure trigger 120 proximally toward the pistol grip 118, the linkage 206 may be pushed distally, causing corresponding distal motion of the secondary yoke 200, compressing the spring 202 biases the yoke proximally and, in turn, pushing the yoke 192 and closure sleeve 128 distally. Distal movement of the closure sleeve 128 may cause pivotal translation movement of the anvil 112 distally and toward the elongate channel 110 of the end effector 104 and proximal movement effects closing, as described below.

As the closure trigger 120 is pulled towards the pistol grip 118, the lever portion 180 of the trigger 120 may translate distally. When the closure trigger 120 is fully pulled against the pistol grip 118, a clamp lock switch 124 may pivot about a clamp lock pin 208 to lock the closure trigger 120 into the clamped position. For example, the clamp lock switch 124 may be biased by a spring (not shown) to pivot about the pin 208. The clinician may unlock the closure trigger 120, for example, by actuating the clamp lock switch 124, causing it to pivot about the clamp lock pin 208 (clockwise as shown in FIGS. 6 and 8). This may allow the closure trigger 120 to return to the open position, causing proximal motion of the closure sleeve and pivoting the anvil 112 proximally and away from the elongate channel 110 of the end effector 104, as described below.

As the closure trigger 120 is moved toward the pistol grip 118, its intermediate section 182 may be pulled proximally, causing the firing trigger 122 to also move proximally to its "firing" position. When in its firing position, the firing trigger 122 may be located at an angle of approximately 45° to the pistol grip 118. To fire the instrument 102, the clinician may first deactivate a firing trigger safety 210. For example, the safety 210 may be pivotally coupled to the closure trigger 120 about a pin 212. A distal portion of the safety 210 may be received into a cavity 214 of the firing trigger 122, preventing the firing trigger 122 from being actuated. The clinician may deactivate the safety 210 by removing it from the cavity 214 and pivoting the safety 210 proximally. This may allow the clinician to actuate the firing trigger 122.

The firing trigger 122 may be biased to an "off" position by a biasing member such as a spring 216 (FIG. 9). When actuated (e.g., against the force of the spring 216), the firing trigger 122 may be rotated clockwise, as shown in FIG. 9. A contactor portion 218 of the trigger may activate a trigger switch 220, e.g., via an actuator 221, which may initiate firing of the instrument 102. Actuation of the trigger switch 220 may activate a motor 222. The motor 222 may be coupled to a gearbox 224 comprising an enclosure 226 and gear cluster 228. The gearbox 224 may gear down the motor 222. In one example embodiment, the motor 222 may rotate at 106,000 RPM, while the gearbox 224 may have a ratio of 509-to-1.

An intermediate gear 230 may be coupled to the output of the gearbox 224. The intermediate gear 230 may be in mechanical communication with a drive gear 232. The drive gear 232 may be rotatable about a drive shaft 234. A biasing member such as a spring 236 may bias the drive gear 232 and/or drive shaft 234 such that the drive gear 232 is in mechanical communication with a geared face 240 of a rack 238. The rack 238 may be coupled to the firing drive member 130 which may, ultimately, be in mechanical communication with the firing bar 108. Accordingly, rotation of the motor 222 may cause rotation of the gearbox 224, leading to rotation of the intermediate 230 and drive 232 gears. Rotation of the drive gear 232 may result in distal or proximal motion of the rack 238, drive member 130, and drive bar 108. Distal and proximal motion of the drive bar 108 may cause the instrument 102 to fire, for example, as described herein below.

When the instrument is fired, the rack 238 may translate distally. A top geared face 242 of the rack 238 may coupled to a clamp lock 244, causing the clamp lock 244 to translate distally about a pivot pin 246. In its distal position, the clamp lock 244 may contact the clamp switch 124, preventing it from disengaging as described above. In this way, the clinician may be mechanically prevented from releasing the clamp switch 124 while the instrument 102 is in a fired position (e.g., the drive bar 108 is extended distally).

According to various embodiments, the surgical instrument 102 may comprise mechanisms allowing a clinician to disable the motor 222 and manually disengage the firing bar 108. For example, the instrument 102 may comprise an emergency access door 248. The access door 248 may be coupled to a switch, as described below, such that when the clinician opens the access door 248, electric power to the motor 222 may be cut. Below the access door 248, the device 102 may comprise a manual retraction lever 250. The retraction lever 250 may be rotatable about a pivot a pin 252. A locking cam 254 may also be pivotable about the pin 252. After the clinician has opened and/or removed the access door 248, the clinician may pull up on the retraction lever 250. This may cause the lever 250 to rotate about the pin 252 (clockwise as shown in FIG. 9 and counter clockwise as shown in FIG. 6). Initially, the locking cam 254 may rotate with the retraction lever 250. As the locking cam 254 rotates, a locking arm 256 of the cam 254 may contact a top surface 258 the drive gear 232, working against the bias of the spring 236 to push the drive gear 232 down and out of contact with the geared face 240 of the rack 238. This may disengage the motor 222 from the rack 238, drive member 130 and drive bar 108. When the locking cam 254 is rotated by a predetermined amount, the locking arm 256 may lock against the drive gear 232, preventing reverse rotation of the locking cam 254.

Figure 10:
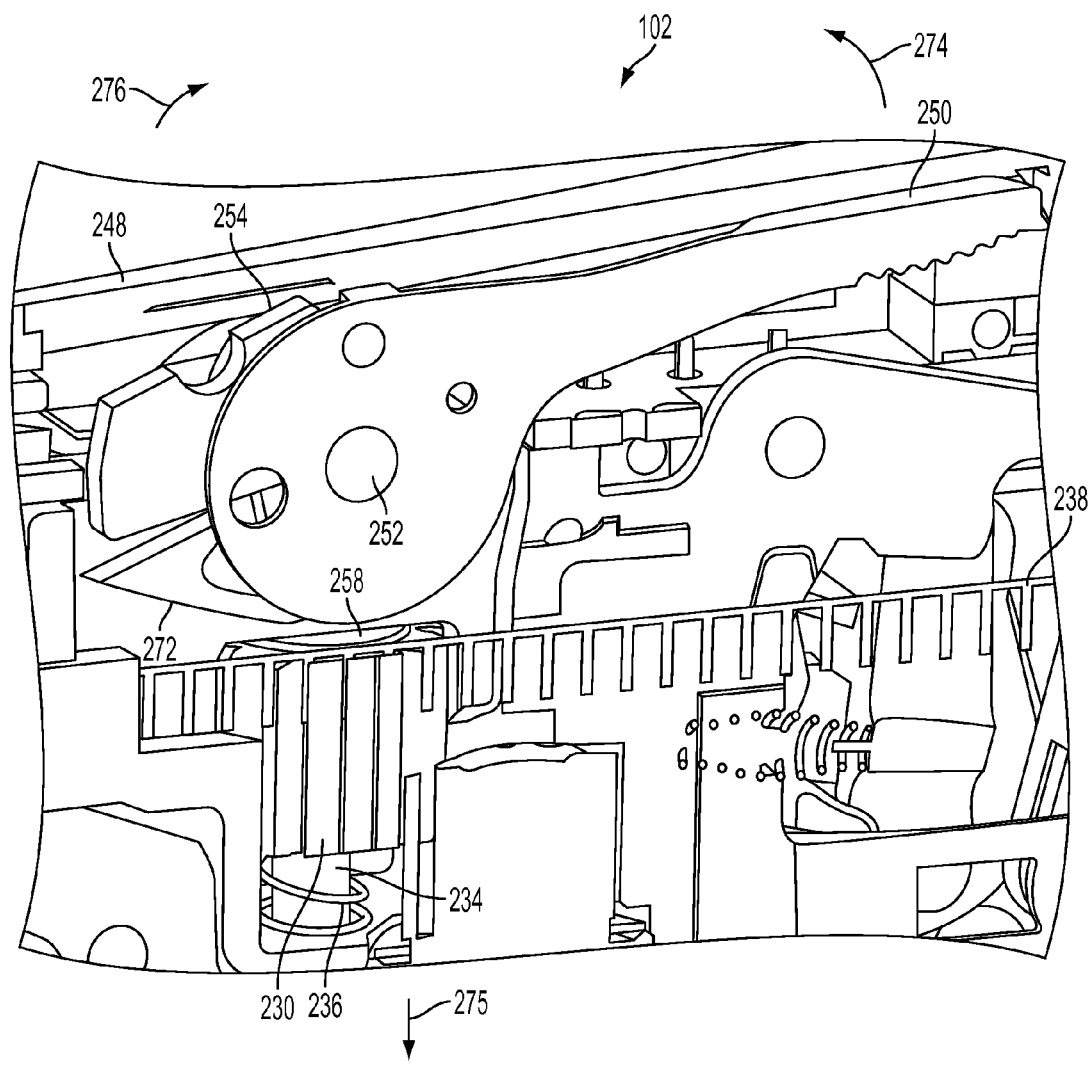
FIG. 10 illustrates a partial cross-sectional view of one embodiment of the surgical instrument of FIG. 1 with various components removed for clarity showing the operation of the retraction lever.
Figure 11:
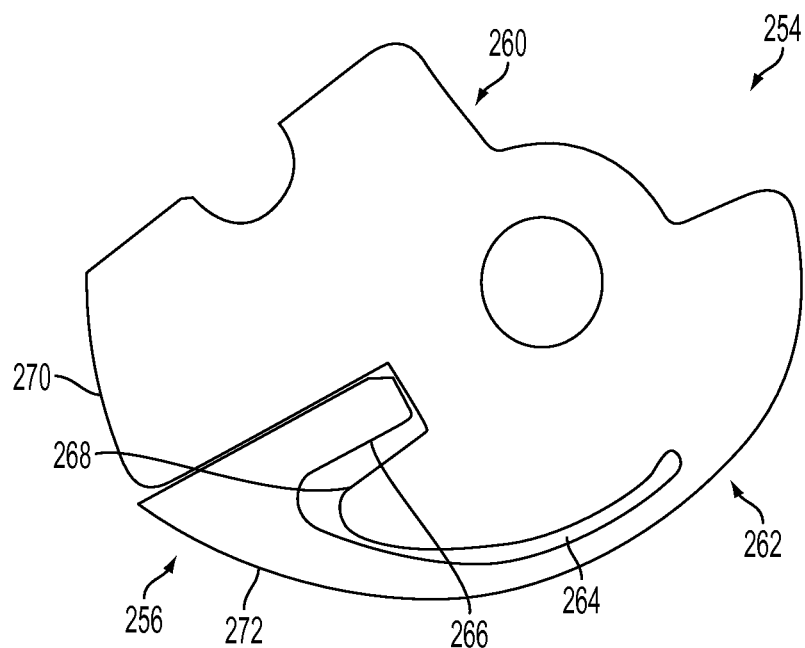
FIGS. 11 and 12 illustrate one embodiment of a locking cam of the surgical instrument of FIG. 1 during various states of operation.
Figure 12:
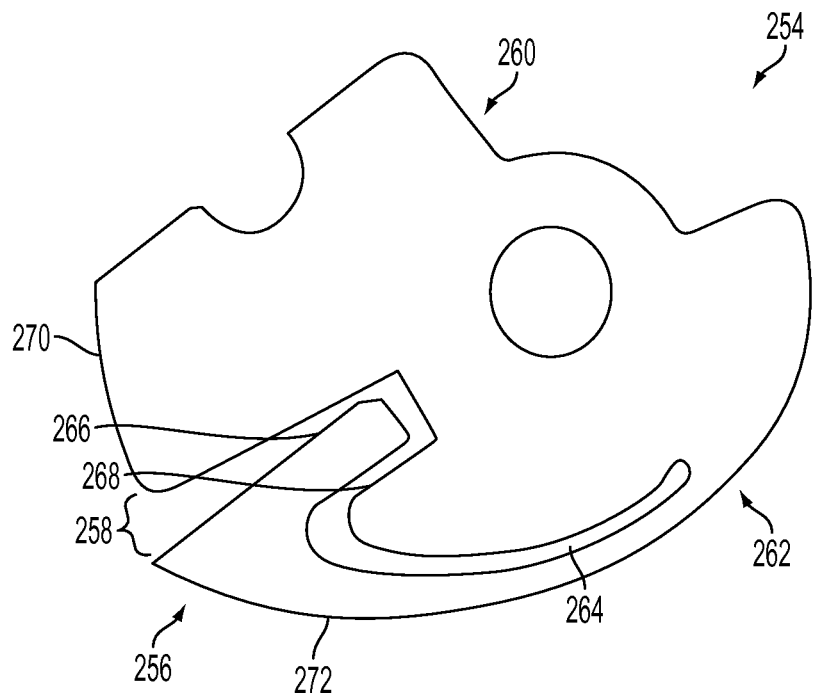

FIGS. 10-15 illustrate additional details of the operation of the locking cam 254. FIG. 10 illustrates a partial cross-sectional view of one embodiment of the surgical instrument 102 with various components removed for clarity showing the operation of the retraction lever 250. In FIG. 10, the rack 238 is shown in cross-section. FIGS. 11 and 12 illustrate one embodiment of the locking cam 254 during various states of operation. The locking cam 254 may comprise a body portion 260. The locking arm 256 that may pivot, or otherwise flex, with respect to the body portion 260 about a hinge portion 262. The hinge portion 262 may comprise, for example, a living hinge. In one embodiment, the body portion 260 and the locking arm 256 may be unitary and formed from a single piece of material. The locking cam 254 may define a clearance 264 that allows the locking arm 256 to pivot toward the body portion 260. The locking arm 256 may have a tooth 266 that is received by a notch 268 in the body portion 260. On their respective outer peripheries, the body portion 260 may have a first contacting surface 270 and the locking arm 256 may have a second contacting surface 272. In the closed position (FIG. 11), the first contacting surface 270 may be generally aligned with the second contacting surface 272 such that the outer periphery of the locking cam 254 has a generally continuous cammed surface. In the open position (FIG. 12), the locking arm 256 pivots away from the body portion 260 to increase the clearance 264. A gap 258 is created between the first contacting surface 270 and the second contacting surface 272.

Referring now to FIGS. 10, 11, and 12, upon rotation of the lever 250 in the direction indicated by arrow 274, the locking cam 254 is rotated and the second outer surface 272 of the locking arm 256 first contacts a top surface 258 of the intermediate gear 230. As a result of this contact, the locking arm 256 may be pivoted toward the body portion 260 to create a generally continuous periphery. As the locking cam 254 continues to rotate, the second contacting surface 272 and then the first contacting surface 270 exerts force on the intermediate gear 230 to overcome the biasing force applied by the spring 236. As a result, the intermediate gear 230 is pushed in the direction indicated by arrow 275 as the lever 250 is rotated in the direction indicated by arrow 274. The movement of the intermediate gear 230 may decouple it from the geared face 240 of the rack 260 allowing the rack 260 to translate freely. Once the locking arm 256 clears the top surface 258 of the intermediate gear 230, it may pivot to the open position (FIG. 12) to lock the locking cam 254 into place. Once in the open position, the locking cam 254 may be impeded from rotating in the direction indicated by arrow 276 (FIG. 10) due to the engagement of the locking arm 256 with the intermediate gear 230.

Figure 15:
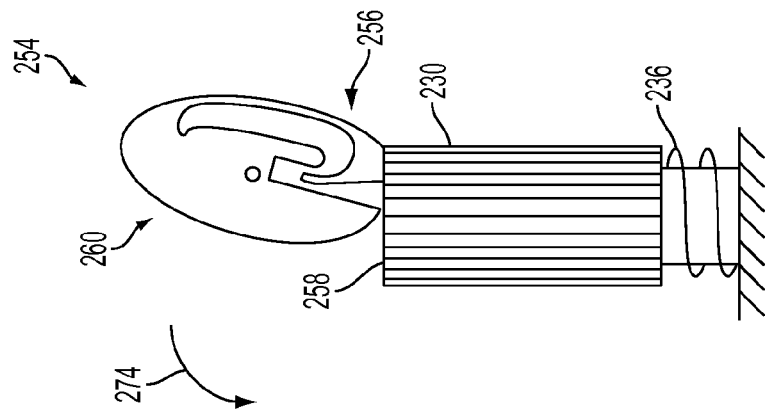
FIGS. 13-15 show various embodiments of the locking cam of FIGS. 11 and 2 and a intermediate gear during three stages of operation.
Figure 14:
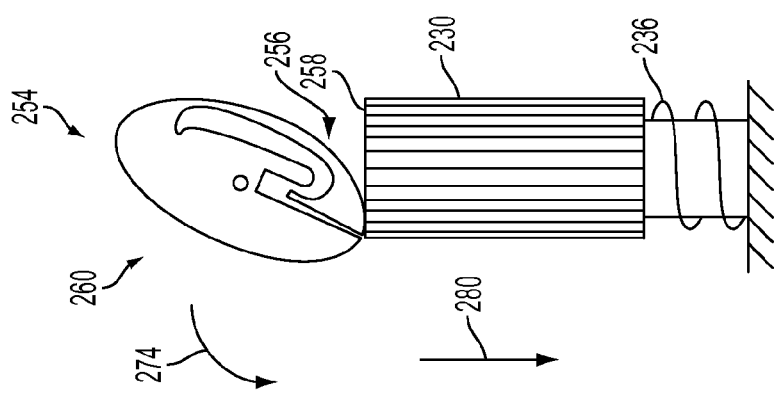
Figure 13:
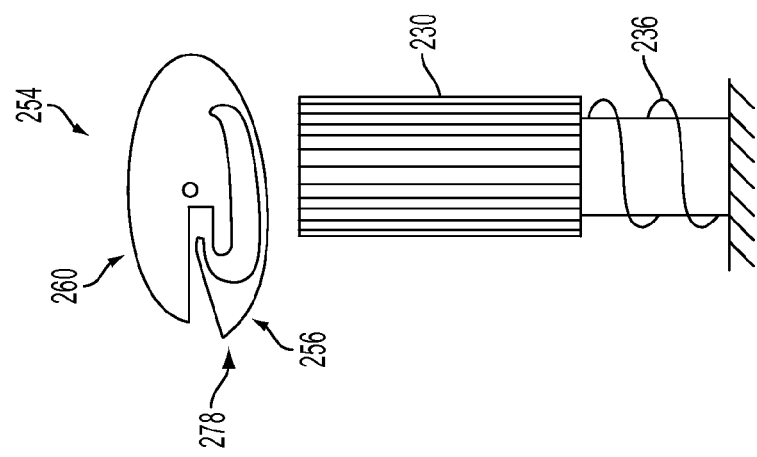
Figure 16:
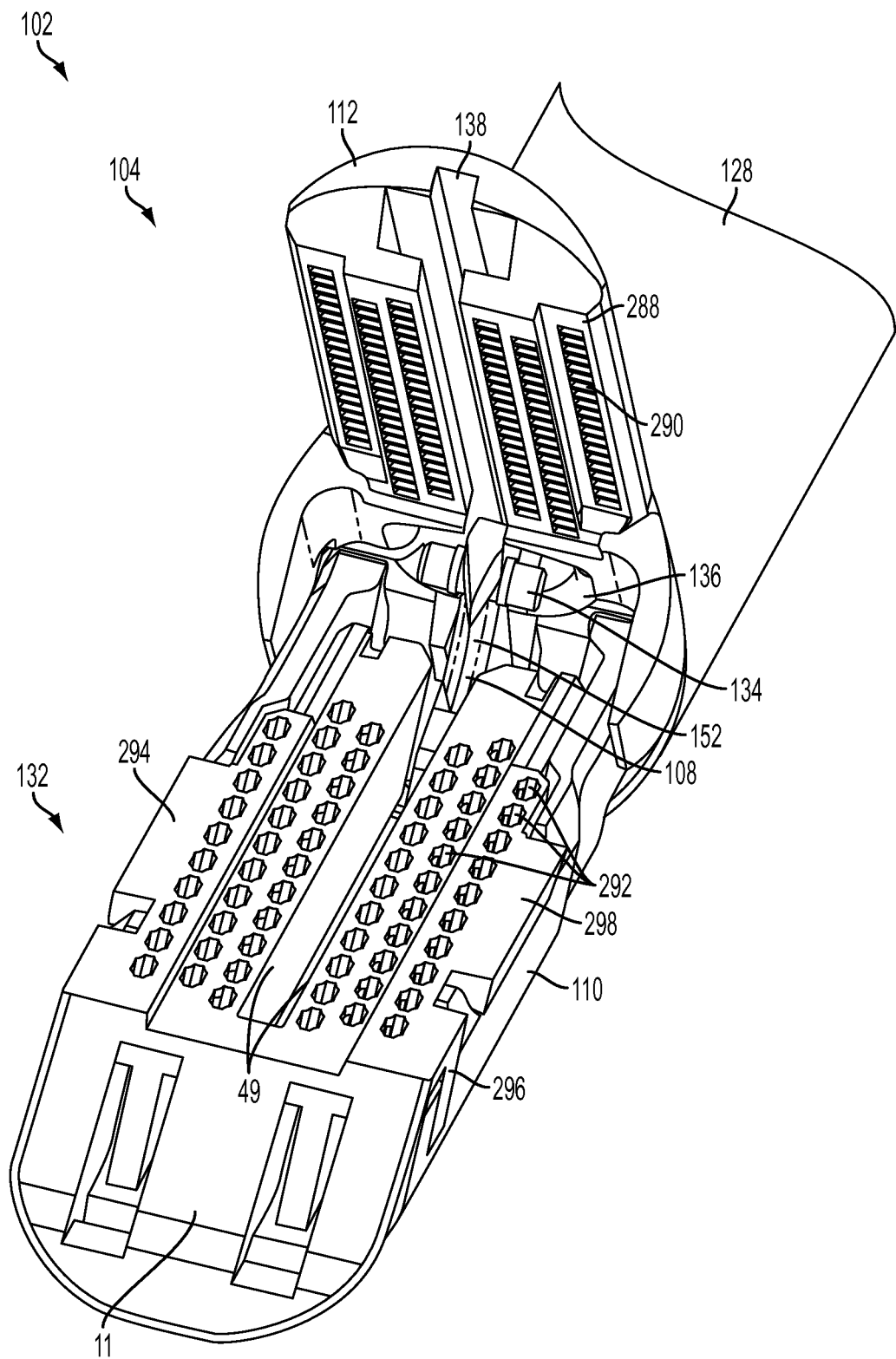
FIG. 16 depicts one embodiment of the end effector of the instrument of FIG. 1 in an open position, as a result of a retracted closure sleeve, with a staple cartridge installed in the elongate channel.

FIGS. 13-15 show various embodiments of the locking cam 254 and a intermediate gear 230 during three stages of operation. Various components have been removed and/or simplified for clarity. As illustrated, the locking cam 254 may be manufactured from a single piece of material. The locking cam 254 comprises a locking arm 256 that is pivotable with respect to a body portion 260. FIG. 13 shows one embodiment of the locking cam 254 in a non-engaged position. In this position, a distal portion 278 of the locking arm 256 is separated from the body portion 260. As illustrated in FIG. 14, when the locking cam 254 is rotated in the direction indicated by arrow 274, the locking arm 256 is drawn toward the body portion 260 to create a generally continuous periphery spanning the locking arm 256 and the body portion 260. As the locking cam 254 contacts a top face 258 of the intermediate gear 230, the gear 230 may move in the direction indicated by arrow 280. As the locking cam 254 continues to rotate in the direction indicated by arrow 274, eventually the locking arm 256 passes over the drive shaft 234. As shown in FIG. 15, when the distal portion 278 of the locking arm 256 separates from the body portion 260, it engages the teeth of the intermediate gear 230 to lock the locking cam 254 into an engaged position. Accordingly, in various embodiments, while the locking cam 254 may be made from a single piece of material, it may function as two parts (e.g., a cam and a locking mechanism).

Referring now to FIG. 6, the retraction lever 250 may also comprise a ratchet arm 282 rotatable about a ratchet pin 284. As the retraction lever 250 is pulled up, a tooth portion 286 of the ratchet arm 282 may come into contact with the top geared face 242 of the rack 238. Further rotation of the ratchet lever 250 may cause the tooth 286 to exert a proximally directed force on the rack 238, causing the drive member 130 and drive bar 108 to translate proximally. Further lifting of the retraction lever 250 may disengage the tooth portion 286 from the top geared face 242, allowing the clinician to replace the retraction lever 250 towards its original position without causing corresponding distal motion of the rack 238. Additional proximal motion of the rack 126, drive member 130 and drive bar 108 may be achieved by additional lifting of the retraction lever 250, repeating the process described above.

Figure 17:
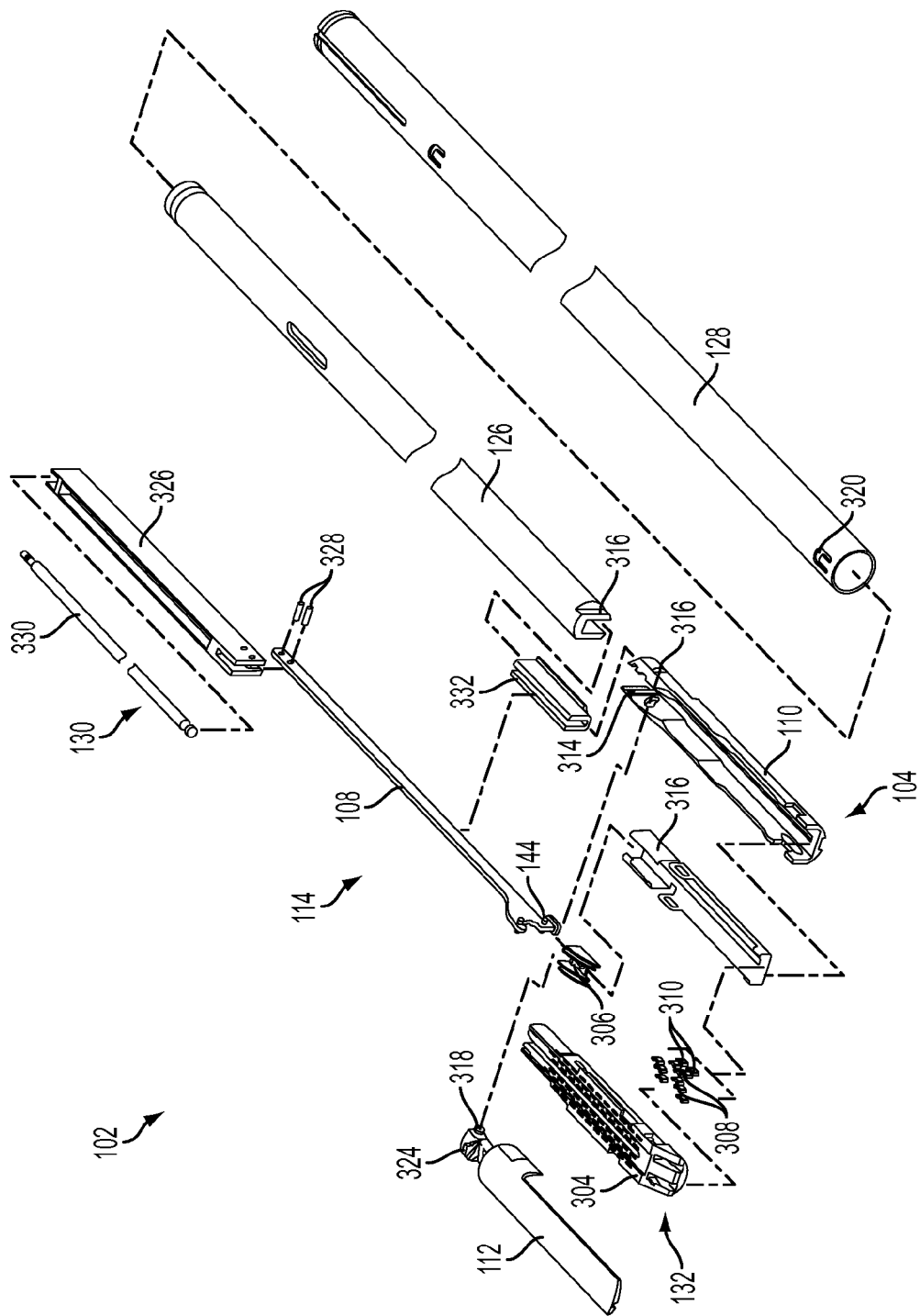
FIG. 17 shows one embodiment of the implement portion of the surgical stapling and severing instrument of FIG. 1 in disassembled form.

FIG. 17 shows one embodiment of the implement portion 114 of the surgical stapling and severing instrument 102 in disassembled form. The staple cartridge 132 is shown as being comprised of a cartridge body 304, a wedge sled 306, single and double drivers 308, staples 310, and a cartridge tray 312. When assembled, the cartridge tray 312 holds the wedge sled 306, single and double drivers 308, and staples 310 inside the cartridge body 304.

The elongate channel 110 may have a proximally placed attachment cavity 314 that receives a channel anchoring member 316 on the distal end of the frame 126 for attaching the end effector 104 to the handle portion 106. The elongate channel 110 may also have an anvil cam slot 316 that pivotally receives an anvil pivot 318 of the anvil 112. The closure sleeve 128 that encompasses the frame 126 may include a distally presented tab 320 that engages an anvil feature 324 proximate but distal to the anvil pivot 318 on the anvil 112 to thereby effect opening and closing of the anvil 112. The firing drive member 130 is shown as being assembled from the firing bar 108 attached to a firing connector 326 by pins 328, which in turn is rotatingly and proximally attached to the metal drive rod 330. The firing bar 108 is guided at a distal end of the frame by a slotted guide 332 inserted therein.

Figure 18:
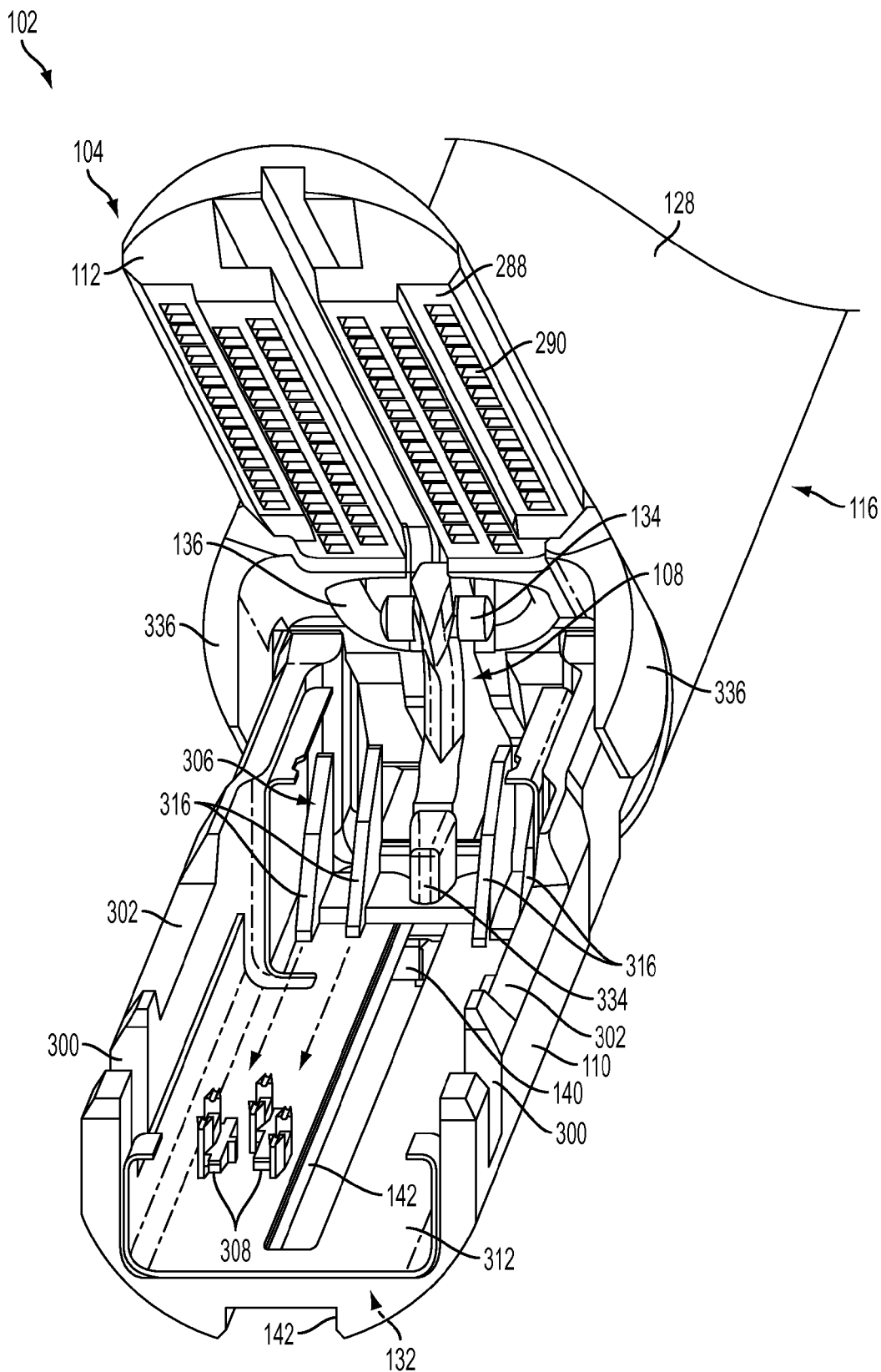
FIG. 18 shows one embodiment of the end effector of the instrument of FIG. 1 with a portion of the staple cartridge removed.

With particular reference to FIG. 18, a portion of the staple cartridge 132 is removed to expose portions of the elongate channel 110, such as recesses 300, 302 and to expose some components of the staple cartridge 132 in their unfired position. In particular, the cartridge body 304 (shown in FIG. 17) has been removed. The wedge sled 306 is shown at its proximal, unfired position with a pusher block 334 contacting the middle pin 144 (not shown in FIG. 18) of the firing bar 108. The wedge sled 306 is in longitudinal sliding contact upon the cartridge tray 312 and includes wedges 308 that force upward the single and double drivers 308 as the wedge sled 306 moves distally. Staples 310 (not shown in FIG. 18) resting upon the drivers 308 are thus also forced upward into contact with the anvil forming pockets 290 on the anvil 112 to form closed staples. Also depicted is the channel slot 142 in the elongate channel 110 that is aligned with the vertical slot 154 in the staple cartridge 132.

Figure 19:
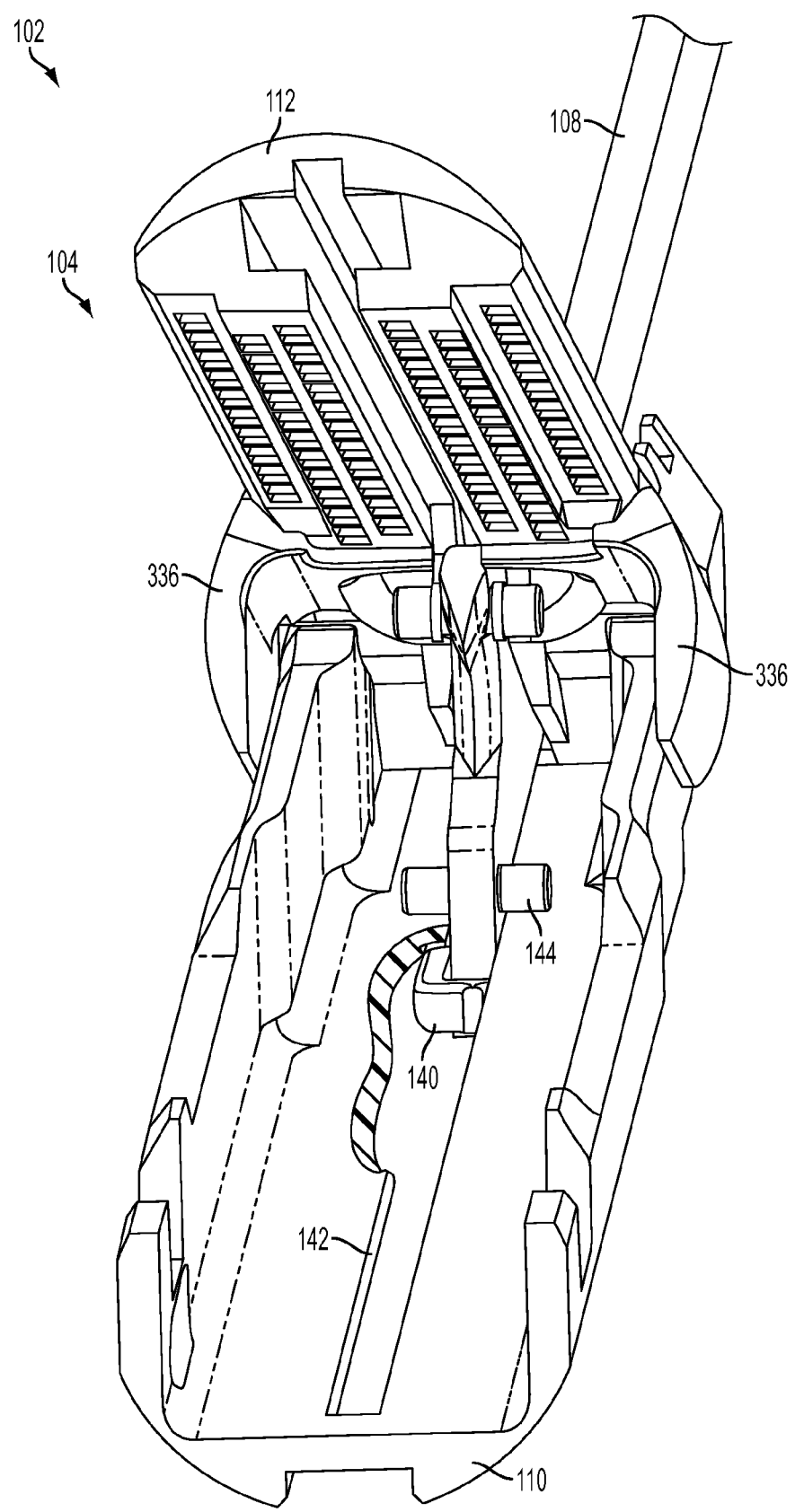
FIG. 19 depicts the end effector of FIG. 18 with all of the staple cartridge removed.

FIG. 19 depicts the end effector 104 of FIG. 18 with all of the staple cartridge 132 removed to show the middle pin 144 of the firing bar 108 as well as portion of the elongate channel 110 removed adjacent to the channel slot 142 to expose the firing bar cap 140. In addition, portions of the shaft 116 are removed to expose a proximal portion of the firing bar 108. Projecting downward from the anvil 112 near the pivot, a pair of opposing tissue stops 346 may prevent tissue being positioned too far up into the end effector 104 during clamping.

Figure 20:
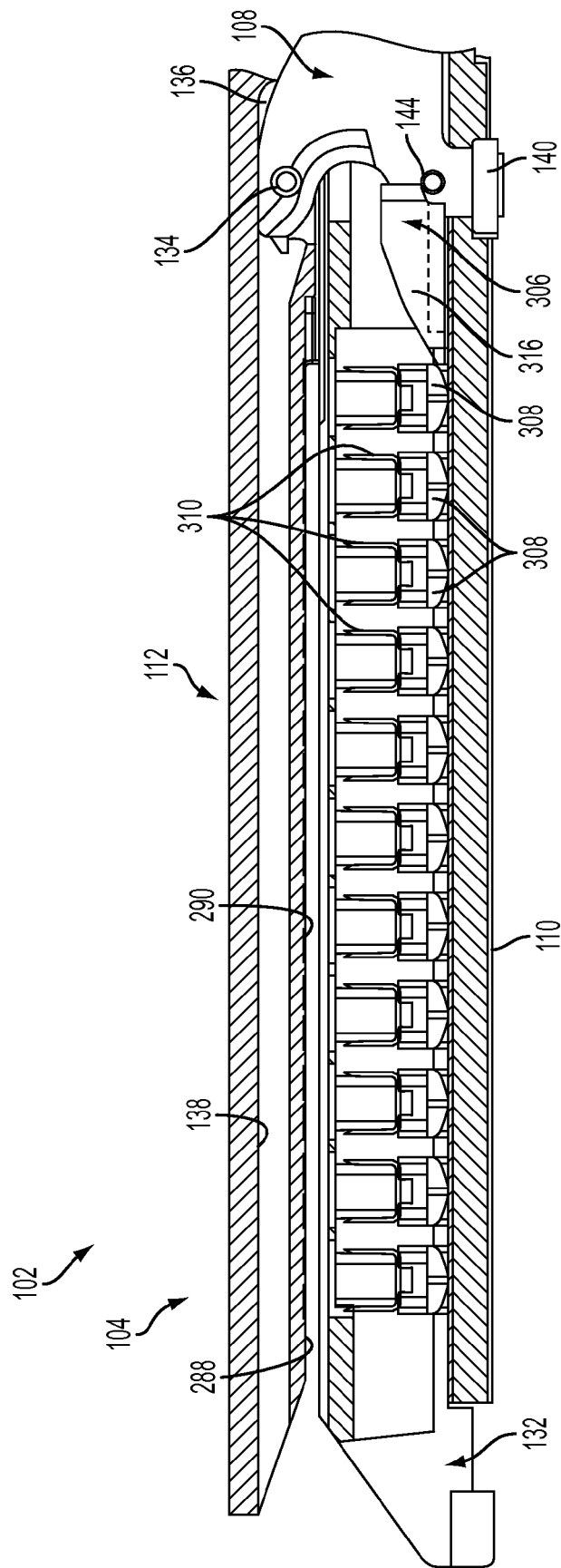
FIG. 20 depicts one embodiment of the end effector of the instrument of FIG. 1 closed in a tissue clamping position with the firing bar unfired.

FIG. 20 depicts one embodiment of the end effector 104 closed in a tissue clamping position with the firing bar 108 unfired. The upper pin 134 is shown in the anvil pocket 136, vertically aligned with the anvil slot 138 for distal longitudinal movement of the firing bar 108 during firing. The middle pin 144 may be positioned to push the wedge sled 306 distally so that wedge 308 sequentially contacts and lifts double drivers 308 and the respective staples 310 into forming contact with staple forming pockets 290 in the lower surface 288 of the anvil 112. According to various embodiments, the end effector 104 may implement a mechanical lock-out mechanism. The mechanical lock-out mechanism may prevent the instrument 102 from being fired twice without reloading a new staple cartridge 132. For example, it will be appreciated that firing the instrument 102 without a loaded staple cartridge present may cause tissue to be cut, but not fastened. The lock-out may be implemented in any suitable manner. For example, the firing bar 108, upon retraction in the proximal direction, may be shifted by the elongate channel 110, or other component, such that the upper pin 134 is no longer in alignment with the anvil slot 138, preventing the firing bar 108 from moving distally (e.g., re-firing). Installation of a new staple cartridge 132 to the elongate channel 110 may snap the firing bar 108 back, aligning the upper pin 134 with the anvil slot 138 and allowing re-firing. It will be appreciated that any suitable mechanism in the end effector or the handle 106 may be utilized to implement a mechanical lock-out.

FIG. 21 depicts one embodiment of the upper surface 294 of the staple cartridge 132 with the firing bar 108 in its unfired, proximal position. The stapler apertures 292 are arrayed on each side of the vertical slot 154 in the staple cartridge 132. FIG. 22 depicts one embodiment of the end effector 104 near the pivot showing that the elongate channel 110 has opposing ramp portions 348 to thereby cooperate with the tissue stops 346 of the anvil 112 to prevent tissue from jamming the end effector 104. Also depicted in greater detail are the double drivers 308 and their relation to the staples 310.

Figure 23:
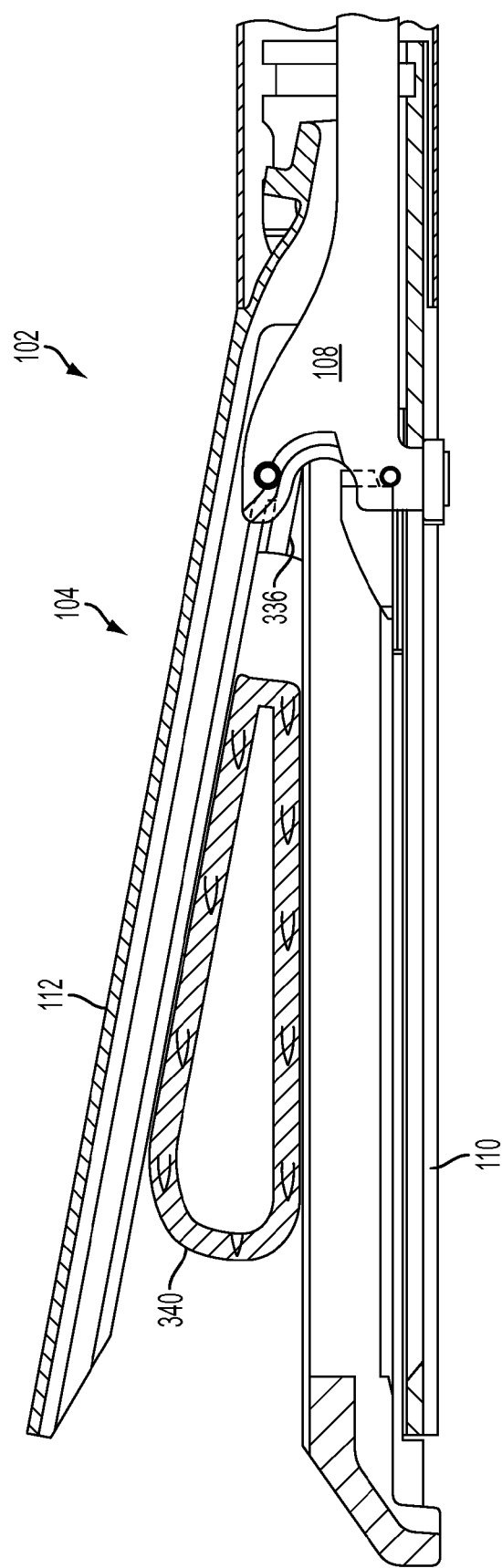
FIG. 23 illustrates one embodiment of the end effector of the instrument of FIG. 1 with tissue present between the staple cartridge and the anvil.
Figure 24:
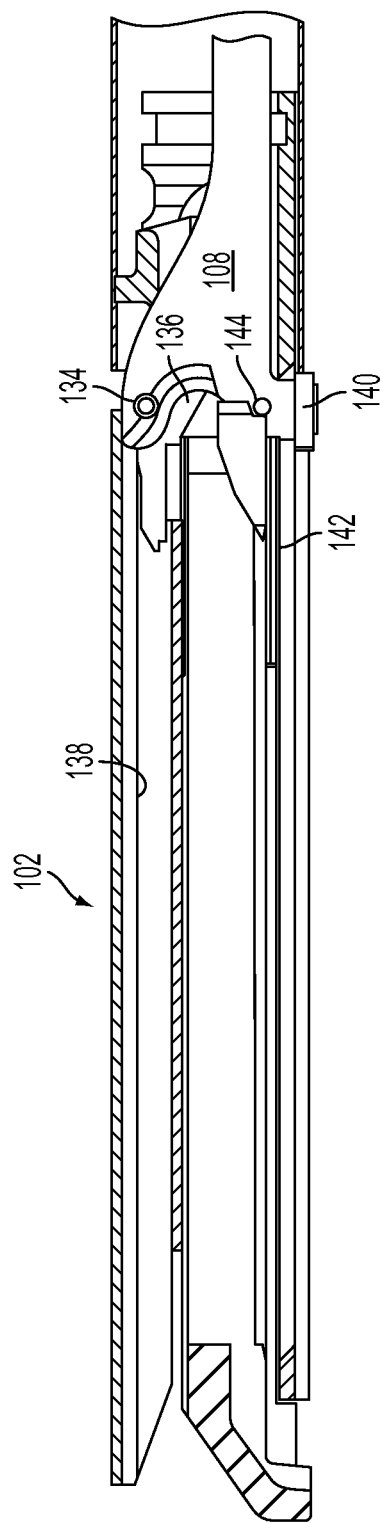
FIGS. 24-26 illustrate one embodiment of the end effector of the instrument of FIG. 1 at various stages of firing.
Figure 25:
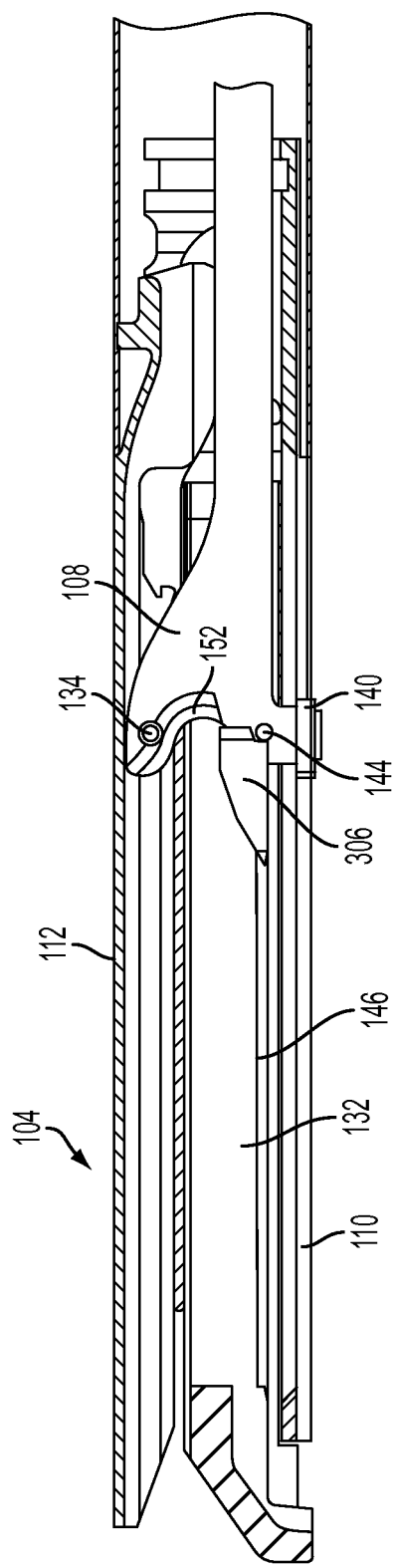
Figure 26:
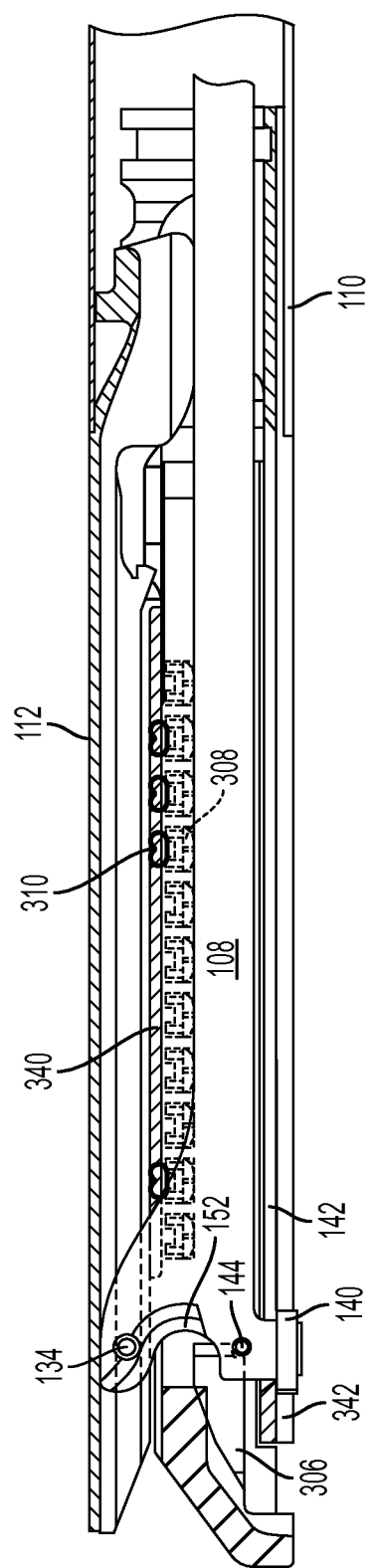

FIGS. 24-26 illustrate one embodiment of the end effector 104 at various stages of firing. In use, the surgical stapling and severing instrument 102 may be used to cut and staple tissue. In FIGS. 1-2, the instrument 102 is shown in its start position, having had an unfired, fully loaded staple cartridge 132 snap-fitted into the distal end of the elongate channel 110. Both triggers 120, 122 are forward and the end effector 104 is open, such as would be typical after inserting the end effector 104 through a trocar or other opening into a body cavity. The instrument 102 may then be manipulated by the clinician such that tissue 340 to be stapled and severed is positioned between the staple cartridge 132 and the anvil 112. FIG. 23 illustrates the end effector 104, according to one embodiment, with tissue 340 present between the staple cartridge 132 and the anvil 112.

Next, the clinician moves the closure trigger 120 proximally until positioned directly adjacent to the pistol grip 118, locking the handle portion 106 into the closed and clamped position. The retracted firing bar 108, shown in FIG. 24 in the end effector 104 may not impede the selective opening and closing of the end effector 104, but rather may reside within the anvil pocket 136. With the anvil 112 closed and clamped, the firing bar 108 may be aligned for firing through the end effector 104. In particular, the upper pin 134 may be aligned with the anvil slot 138 and the elongate channel 110 may be affirmatively engaged about the channel slot 142 by the middle pin 144 and the firing bar cap 140.

After tissue clamping has occurred, the clinician may move the firing trigger 122 proximally causing the firing bar 108 to move distally into the end effector 104, shown in FIG. 25. In particular, the middle pin 144 enters the staple cartridge 132 through the firing drive slot 146 to cause the firing of the staples 310 via wedge sled 306 toward the anvil 112. The lower most pin, or firing bar cap 140, cooperates with the middle pin 144 to slidingly position cutting edge 152 of the firing bar 108 to sever tissue. The two pins 140, 144 also position the upper pin 134 of the firing bar 108 within longitudinal anvil slot 138 of the anvil 112, affirmatively maintaining the spacing between the anvil 112 and the elongate channel 110 throughout its distal firing movement.

The clinician may continue moving the firing trigger 122 until brought proximal to the closure trigger 120 and pistol grip 118. Thereby, all of the ends of the staples 310 may be bent over as a result of their engagement with the anvil 112, as shown in FIG. 26. The firing bar cap 140 may be arrested against a firing bar stop 342 projecting toward the distal end of the channel slot 142. The cutting edge 152 may have traversed completely through the tissue. The process is complete by releasing the firing trigger 122. Releasing the firing trigger 122 may, as described herein below, cause the motor 222 to reverse its rotation, causing retraction of the firing bar 108. Upon retraction of the firing bar 108, the clinician may depress the clamp switch 124. (e.g., while simultaneously squeezing the closure trigger 120) This may open the end effector 104.

Referring back to FIG. 1, the handle 106 of the instrument 102 may house at least one battery unit 506. The battery unit 506 may comprise a single battery or a plurality of batteries arranged in a series and/or parallel configuration. The handle 502 may comprise a battery dock 508 to which the battery unit 506 may be attached. The battery dock 508 may be any suitable structure for coupling the battery unit 506 to the instrument 102. For example, the battery dock 508 may be or comprise a cavity in the handle 106 configured to receive at least a portion of the battery unit 506, as illustrated. In other embodiments, the battery dock 508 may be implemented using a variety of other structures. In one embodiment, the battery dock 508 may comprise a post that is received by the battery unit 506. In one embodiment, the pistol grip 120 may comprise the battery dock 508. In any event, as discussed in more detail below, the battery dock 508 may comprise a protruding portion to interact with the battery unit 506 upon attachment of the battery unit 506 to the handle 502. Once attached, the battery unit 506 may be electrically connected to and may provide power to the motor 222 of the instrument 102.

FIGS. 27-29 schematically illustrate one embodiment of the battery unit 506 and a portion of the instrument 102 showing the attachment and detachment of the battery unit 506 to the instrument 102. The battery unit 506 may comprise a drain 512 that automatically completes a circuit within the battery unit 506 upon attachment to the instrument 102. The drain may serve to slowly reduce the charge of the battery unit 506 over time. Once the battery unit 506 has been sufficiently drained it may be disposed as non-hazardous waste, for example. The battery unit 506 may comprise a voltage source 510. In one embodiment, the voltage source 510 is a lithium battery and comprises at least one cell selected from the group consisting of a CR123 cell and a CR2 cell. As is to be appreciated, any suitable voltage source may be used. The battery unit 506 may also comprise a drain 512 that may be electrically coupled to the voltage source 510 when a switch 516 is closed. The battery unit 506 and the instrument 102 each comprise electrically conductive contacts 518, 520, respectively, that are placed into contact upon attachment of the battery unit 506 to the instrument 102. FIG. 27 illustrates the battery in a non-attached position. The switch 516 is in an open position and the voltage source 510 may be in a fully charged condition. FIG. 28 illustrates that battery unit 506 in an attached position. The conductive contacts 518 of the battery unit 506 are in electrical communication with the contacts 520 of the instrument thereby allowing the battery unit 506 to supply energy to the circuit 514 (FIG. 46). In the attached position, the switch 516 may transition to the closed position to electrically couple the voltage source 510 to the drain 512. Energy will flow from the voltage source 510 through the drain 512 during operation of the instrument. In other words, the drain 512 will be draining the charge from the voltage source 510 concurrently as the battery unit 506 is supplying operational power to the instrument 102. As discussed in more detail below, a portion of the instrument 102 may physically interact with the drain 512 during attachment of the battery unit 506 to the instrument 102 to transition the switch 516 from the open to the closed state. FIG. 29 illustrates the battery unit 506 in a non-attached position. In one embodiment, the switch 516 remains in the closed position to continue to drain the voltage source 510 even after the battery unit 506 has been detached from the instrument 102.

FIG. 30 illustrates a graph 600 of the voltage level of one embodiment of the battery unit 506 over time, as measured from the time of attachment to the instrument 102. The graph 600 includes three example discharge curves 602, 604, 606. As illustrated by the first discharge curve 602, the voltage of the power source 510 may drop below 2.0 volts after around 28 hours. As illustrated by the second discharge curve 604, the voltage of the power source 510 may drop below 2.0 volts after around 30 hours. As illustrated by the third discharge curve 606, the voltage of the power source 510 may drop below 2.0 volts after around 33 hours. The overall shape of the discharge curve may depend upon, for example, the level of activity of the instrument 102 during the surgical procedure. For example, the instrument associated with the first discharge curve 602 was more heavily used during the surgical procedure than the instrument associated with discharge curve 606. In any event, the drain 512 may maintain the voltage level of the battery unit 506 at a satisfactory level for a certain time period to ensure that the instrument can be used for its intended purpose during the course of the surgical procedure. For example, in one embodiment, the voltage level of the battery unit 506 may be maintained around 6 volts for approximately 12 hours. After 12 hours, the voltage level gradually decreases to a non-hazardous level. As is to be appreciated, the drain 512 may be calibrated to deplete the voltage source faster or slower.

In one embodiment, a resistive element may be used to reduce the energy level of the voltage source. FIG. 31 shows a simplified circuit diagram of one embodiment of a battery unit 616 comprising a drain 612. The battery unit 616 may be attached to an instrument 102, for example, via its contacts 618. In this embodiment, the battery unit 616 may comprise a first grouping of cells 610 and a second grouping of cells 611. In one embodiment, the first and second grouping of cells 610, 611 may be lithium batteries. The first and second grouping of cells 610, 611 may each have a plurality of separate cells 610a, 610b, 611a, 611b arranged in a parallel formation. For example, the first and second grouping of cells 610, 611 may each be 6 VDC and arranged in a series configuration to produce 12 VDC at the contacts 618 of the battery unit 616 when fully charged. The cells 610a, 610b, 611a, 611b, however, may be electrically connected to one another in series or parallel or any other combination thereof. The number of cells 610a, 610b, 611a, 611b may be chosen to reduce the fire hazard resulting from the battery unit 616. For example, the number of connected cells may be selected such that the cumulative energy available to an arc or short is less than the energy required to ignite common shipping and/or packing materials. According to various embodiments, this value may be defined by appropriate government regulations.

In one embodiment, the drain 612 may comprise a first resistive element 622 and a second resistive element 624. As is to be appreciated, in some embodiments, the battery unit 616 may comprise, for example, multiple drains 612 each having more or less than two resistive elements or other circuitry. In the illustrated embodiment, the first resistive element 622 is coupled across a first anode 626 and a first cathode 628 of the first grouping of cells 610 through a first switch 630. The first resistive element 624 may be coupled across a second anode 632 and a second cathode 634 of the second grouping of cells 611 through a second switch 636. The first and second switches 630, 636 may be closed upon attachment of the battery unit 616 to the surgical instrument 102 in order to initiate the draining of the first and second grouping of cells 610, 611.

The value of the resistive elements utilized by the drain 612 may vary based on implementation. In one embodiment, the first resistive element 622 has a resistance in the range of about 90 ohms to about 110 ohms. In one embodiment, the first resistive element 622 has a resistance in the range of about 97 ohms to about 104 ohms. In one embodiment, the resistive element 622 is 102.9 ohms and has a power rating of 1 watt. The determination of the necessary resistance is based at least partially on the capacity of the voltage source, the voltage level of the voltage source, and the desired temporal length of the drainage curve. For example, in one embodiment the battery capacity of the first grouping of cells 610 is 1400 mAh, the voltage level is 6 VDC, and the target drain time is 24 hours. Diving 1400 mAh by 24 hours yields a current of 0.0582 A. Using Ohm's law, 6 V divided by 0.582 A yields a resistance of 102.9 ohms. With a current of 0.583 and a resistance of 102.9 ohms, the power dissipated by the resistor is 350 W. As is to be appreciated, different voltage levels, battery capacities, and desired time of discharge will result in different resistance values.

FIG. 32 is a simplified circuit diagram of one embodiment of a battery unit 716 comprising a first drain 712 and a second drain 713. The battery unit 716 may be attached to an instrument 102, for example, via its contacts 718. In this embodiment, the battery unit 716 comprises a first grouping of cells 710, a second grouping of cells 711, and a third cell 714. The first drain 712 comprises a first resistive element 722 and a second resistive element 724. The second drain 713 comprises a third resistive element 726. The resistive elements 722, 724, 726 are coupled to respective cells through switches 730, 736, and 738. The switches 730, 736, and 738 may be closed upon attachment of the battery unit 716 to the surgical instrument 102 in order to initiate the draining of the first and second grouping of cells 610, 611 and the third cell 716. The resistance of the third resistive element 726 may be similar or different from the resistances of the first and second resistive element 722, 724. As described above, the resistance of the third resistive element 726 may at least partially depend on the voltage of the third cell 714 and the desired characteristics of the drainage curve.

Figure 34:
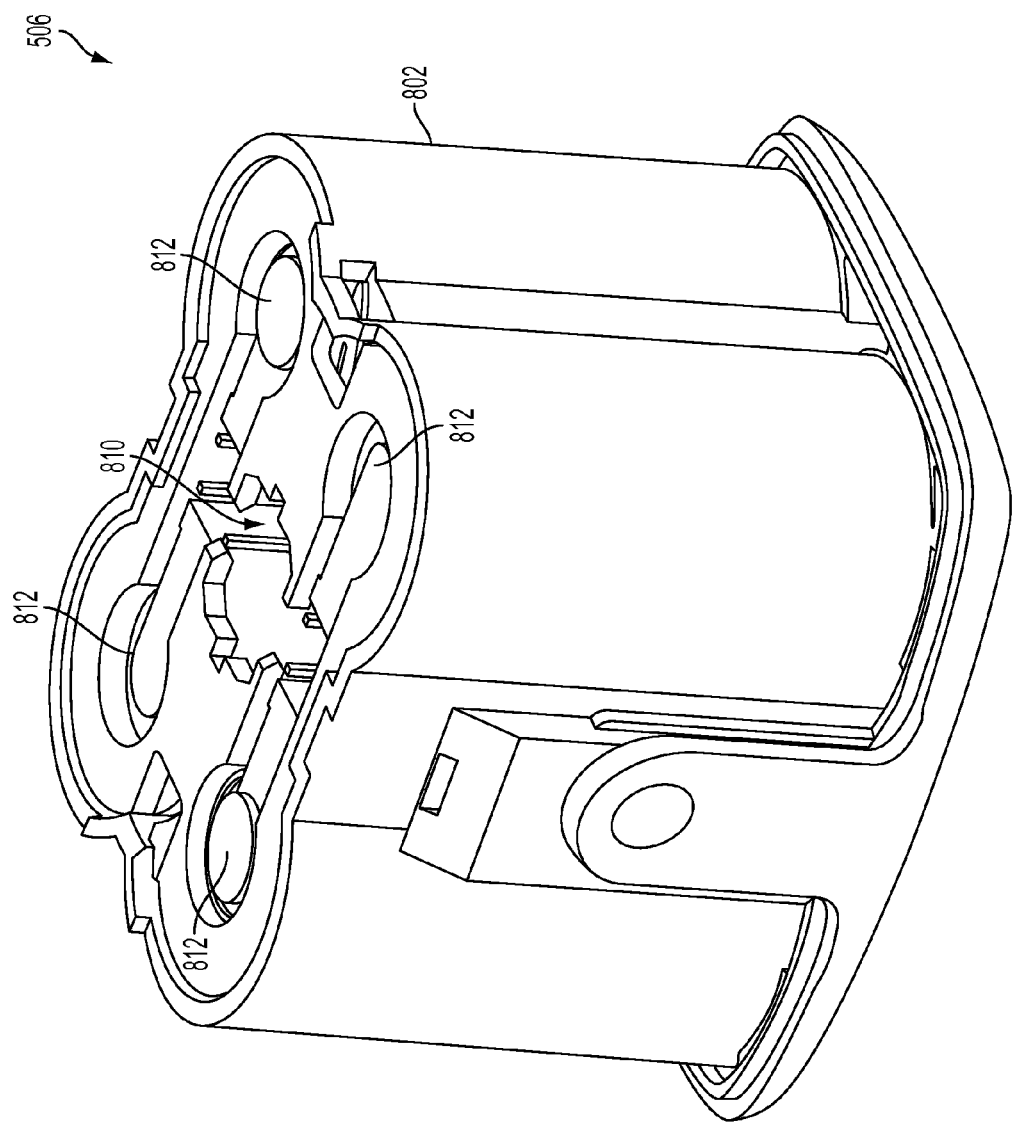

FIGS. 33-36 are perspective views of one embodiment of a battery unit 506 implementing the schematic of the battery unit 616 shown in FIG. 31. The battery unit 506 may comprise a casing 802 defining an interior cavity 810. While the interior cavity 810 is illustrated in a central portion of the casing 802, it is to be appreciated that the internal cavity 810 may be positioned in any suitable location. The casing 802 may be covered by a cap 804 that may be secured to the casing 802 utilizing one or more mechanical latches 806, 808. FIG. 34 illustrates one embodiment of the battery unit 506 with the cap 804 removed to show a plurality of cells 812 within. Any suitable number and/or type of cells 812 may be used. For example, CR123 and/or CR2 cells may be used. FIG. 35 illustrates one embodiment of the battery unit 506 with a portion of the casing 802 removed to reveal the cells 812. FIG. 36 illustrates one embodiment of the battery unit, with a portion of the casing 802 missing as in FIG. 35. FIG. 36 shows the battery pack 506 from a side 890 positioned to face distally when the battery pack 506 is installed on the surgical device 102. The interior cavity 810 is visible as well as a pair of contacts 886, 888 in electrical communication with the various cells 812.

FIGS. 37 and 38 illustrate cross-sectional views of one embodiment of the battery unit 506 including a translatable drain 812. The drain 812 may be positioned within the interior cavity 810 and may be translatable within the interior cavity 810 in the directions of arrow 815. FIG. 37 shows the drain 812 in an open position and FIG. 38 shows the drain 812 in a closed position. The drain 812 may comprise at least two contacts 816, 818. When the drain 812 is in the open position, a portion of the contacts 816, 818 may touch a non-conductive portion of the casing 802, such as fingers 820, 822. According to various embodiments, the contacts 816, 818 may be biased to exert a force against the fingers 820, 822 in order to resist movement of the drain 812 in the direction of the arrows 815. Also, in some embodiments, the fingers 820, 822 may define one or more protrusions or stepped down portions, as shown in FIGS. 37 and 38. The battery unit 506 may also comprise one or more electrodes, such as first electrode 824 and second electrode 826. The first and second electrodes 824 and 826 may each be electrically coupled to a cathode or an anode of cells contained within the battery unit 506. In the closed position (FIG. 38), the contacts 816, 818 are in electrical connection with the electrodes 824, 826, thereby allowing the voltage source to discharge through the drain 812. As discussed in more detail below, the drain 812 may be translated from the open position to the closed position upon attachment of the battery unit 506 to a surgical instrument.

FIG. 43 is a perspective view of one embodiment of the drain 812 in accordance with one non-limiting embodiment. The contacts 816, 818 of the drain 812 may be coupled to a base portion 830 of the drain 812. Similarly contacts 836, 838 of the drain 812 may be coupled to the base portion 830 of the drain 812. According to various embodiments, the contacts 816, 818 may be electrically connected to one another via a resistive element (not shown) mounted to a circuit board 832. Similarly, the contacts 836, 838 may be electrically connected to one another via a resistive element mounted to the circuit board 832. As illustrated, the contacts 816, 818, 836, 838 may have a bend or curvature to bias the contacts towards an outward position when they are inwardly compressed. Additionally, in one embodiment, the distal end of each of the contacts 816, 818, 836, 838 may have an inwardly turned section. The base portion 830 may comprise a contacting surface 840 that engages the instrument when the battery unit 506 is attached to the instrument. Through this engagement, the drain 812 may be translated relative to the casing 802.

FIGS. 39-42 illustrate multiple views of a one embodiment of a battery dock 850. The battery dock 850 may be positioned within the handle 106 of the instrument 102 and may receive the battery unit 506. For example, the battery dock 850 may comprise a protruding member or bulkhead 858. The battery dock 850 may be positioned within the base sections 156, 158 and, in some embodiments, may be coupled to the frame sections 160, 162 such that the protruding member 858 extends proximally. The battery unit 506 may be installed into the device 102 by pushing it distally against the battery dock 850. The protruding member 858 of the battery dock 850 may extend into the exterior cavity 810 of the battery unit 506. Contacts 882, 884 of the battery dock 850 may also extend into the interior cavity 810 of the battery unit 506. Within the cavity, the contacts 882, 884 of the battery dock 850 may be in electrical communication with the contact 886, 888 of the battery unit 506 (FIG. 36). When the contacts 886, 888 of the battery unit 506 come into contact with the contacts 882, 884 of the battery dock 850, the battery unit 506 may be in electrical communication with the instrument 102.

FIG. 44 illustrates one embodiment of the battery unit 506 attached to the battery dock 850. For clarity, various components have been removed. Referring now to FIGS. 37, 38, 43 and 44 as well as to FIGS. 39-42, the battery dock 850 is shown with its protruding member 858 sized to be received by the cavity 810 (FIG. 33) of the battery unit 506. Prior to attachment, the drain 812 may be in the open position (FIG. 37). During attachment of the battery unit 506 to the battery dock 850, the protruding member 858 is inserted into the cavity 810 and the battery unit 506 is moved relative to the battery dock 850 in the direction indicated by arrow 862. Eventually the distal end 860 of the protruding member 858 contacts the contacting surface 840 of the drain 812. As the user continues to attach the battery unit 506, the drain 812 is translated relative to the casing 802 in the direction indicated by arrow 864 and moves into the closed position (FIG. 38). In this position, the battery unit 506 commences to slowly drain. When the battery unit 506 is removed from the battery dock 850, the drain 812 may remain in the position shown in FIG. 38. In this way, the cells (not shown) of the battery unit 506 may drain any remaining charge across a resistive element either before or during disposal.

As is to be appreciated, the translatable discharge drain of the battery unit is not limited to the implementation illustrated in FIG. 44. FIGS. 45 and 46, for example, illustrate one embodiment of a battery unit 900 and drain 912 with various components removed for clarity. The drain 912 that is translatable between an open position (FIG. 45) and a closed position (FIG. 46). In the open position, contacts 916, 918 are engaged with non-conductive portions of a casing 920, 922, respectively. The drain 912 may ride in a track 914 when translating between the open position and the closed position. FIG. 46 shows the battery unit 900 in a closed position after a ram 958 has translated the drain 912 in the direction indicated by arrow 964. The ram 958 may be a component of a battery dock of a surgical instrument, for example. In one embodiment, the battery dock comprises a cavity that is dimensioned to receive the battery unit 900, and the ram 958 is positioned within the cavity. In the closed position, the contacts 916, 918 are in electrical contact with electrodes 924, 926. The drain 912 may comprise a printed circuit board 932 to which at least one resistive element is mounted using a surface mount or a through-hole connection, for example.

FIGS. 47 and 48 illustrate a battery unit 1000 in accordance with another non-limiting embodiment. Various components have been omitted for clarity. The battery unit 1000 may comprise a drain 1012 that may be translatable between an open position (FIG. 47) and a closed position (FIG. 48). The battery unit 1000 may also comprise a first electrode 1024 with a contact 1025 and a second electrode 1026 with a contact 1027. The electrodes 1024, 1026 may be in contact with cells (not shown) of the battery unit 1000. In the open position, contacts 1016, 1018 of the drain 1012 are not engaged with contacts 1025, 1027 of the electrodes 1024, 1026. The drain 1012 may ride in a track 1014 when translating between the open position and the closed position. FIG. 48 shows the battery unit 1000 in a closed position after a ram 1058 has translated the drain 1012 in the direction indicated by arrow 1064. The ram 1058 may be a component of a battery dock of a surgical instrument, for example. In the closed position, the contacts 1016, 1018 of the drain 1012 are in electrical contact with the contacts 1025, 1027 of the electrodes 1024, 1026. The drain 1012 may comprise a printed circuit board 1032 that includes at least one resistive element. In some embodiments, the contacts 1016, 1018 themselves may comprise the resistive elements. In fact, the resistive elements may be elements of any suitable resistance value and any suitable mechanical configuration.

FIG. 49 is a perspective view of one embodiment of a battery unit 1100. FIGS. 50 and 51 show internal views of the battery unit 1100 during various stages of operation with various components removed for clarity. The battery unit 1100 has one cell 1102 and an outer casing 1104 that defines a cavity 1110. The outer casing 1104 may be non-conductive and have conductive contacts for supplying energy to circuitry of a surgical instrument when the battery unit 1100 is attached to a surgical instrument. In one embodiment, the battery unit 1100 is received by a cavity in a pistol grip portion of a surgical instrument. The battery unit 1100 comprises a drain 1112 that is translatable between an open position (FIG. 50) and a closed position (FIG. 51). In one embodiment the drain 1112 has first and second contacts 1116, 1118 that are coupled to a circuit board 1132. The circuit board 1132 may include, for example, at least one resistive element. In some embodiments, the circuit board 1132 includes additional circuitry. The battery unit 1100 comprises a first electrode 1124 coupled to an anode of the cell 1102 and a second electrode coupled to a cathode of the cell 1102. Before the battery unit 1100 is attached to an instrument, the drain 1112 is in the open position (FIG. 50). In the illustrated embodiment, the first contact 1116 is electrically coupled to the first electrode 1124 and the second contact 1118 is resting on, or otherwise contacting, a non-conductive finger 1120. As the battery unit 1100 is attached to an instrument, a protruding portion 1158 of the instrument may be received by the cavity 1110 and contact the drain 1112 to drive the drain 1112 in the direction indicated by the arrow 1164. In the closed position (FIG. 51) the first contact 1116 is electrically coupled to the first electrode 1124 and the second contact 1118 is electrically coupled to the second electrode 1126. In this position, a closed circuit is created that allows the cell 1102 to discharge energy through the drain 1112. Additional embodiments of battery units are disclosed in commonly owned U.S. patent application Ser. No. 12/884,995 entitled, "POWER CONTROL ARRANGEMENTS FOR SURGICAL INSTRUMENTS AND BATTERIES," filed on Sep. 17, 2010 and incorporated herein by reference in its entirety. Still other embodiments of battery units are disclosed in commonly owned U.S. patent application Ser. No. 12/884,838, entitled "SURGICAL INSTRUMENTS AND BATTERIES FOR SURGICAL INSTRUMENTS," filed on Sep. 17, 2010 and also incorporated herein by reference in its entirety.

According to various embodiments, electrical connection of the battery unit 506 or other power supply to the motor 222 may initiate a firing of the instrument 102. FIG. 52 illustrates one embodiment of a control circuit 1200 that may control a connection between the battery unit 506 or other power supply and the motor 222 or other drive device for firing the instrument 102. According to various embodiments, the control circuit 1200 may be implemented with components on a PC board 1202 shown in FIG. 7. The control circuit 1200 may comprise various switches and other components for controlling the connection between the battery unit 506 and the motor 222. The battery unit 506 is shown with a positive electrode 1212 and a negative electrode 1210. Similarly, the motor 222 is shown with a positive terminal 1216 and a negative terminal 1214. It will be appreciated that the polarity of the circuit 1200 could be reversed, for example, based on other design considerations.

The control circuit 1200 may comprise a firing switch 220 (also shown in FIG. 9), which may be in mechanical communication with the firing trigger 120 (e.g., via a actuator 221). The control circuit 1200 may also comprise an end-of-stroke/reverse motor switch 1204 and a clamp switch 1206. The end-of-stroke/reverse motor switch 1204 may be actuated when the firing bar 108 reaches the end of its stroke (e.g., at or near its distal-most position). Also, according to various embodiments, the end-of-stroke/reverse motor switch 1204 may be actuated manually by the clinician prior to the end of the stroke of the firing bar 108 to abort and/or reverse the firing of the instrument 102. A clamp switch 1206 may be actuated when the end effector 104 is closed (e.g., the anvil 112 and elongate channel 110 are brought into contact with one another) and also when the end effector 104 is opened. A clamping relay 1208 may also be a component of the circuit 1200. According to various embodiments, the relay 1208 may be a non-solid state relay (e.g., a mechanical relay, an electromagnetic relay, etc.). This may allow the instrument 102 to be subjected to gamma sterilization as well as other sterilization techniques that have the potential to damage solid state components. It will be appreciated, however, that the clamping relay 1208 may, in various embodiments, be replaced with any sort of switching device including, for example, a field effect transistor (FET), bipolar junction transistor (BJT), etc. Also, in some embodiments, the relay 1208 may be replaced with a microprocessor.

When the instrument is ready for use (e.g., a staple cartridge 132 is loaded to the elongate channel 110), the control circuit 1200 may be configured as shown in FIG. 52. The end-of-stroke/reverse motor switch 1204 may be connected between 1 and 3, creating an electrical connection between the positive electrode 1212 of the battery and the positive terminal 1216 of the motor 222. The relay 1208 may be in a closed state. For example, an electrical connection may be made between pins 4 and 5 of the relay 1208. The firing switch 220 may be connected between points 1 and 3, creating an electrical connection between the positive electrode 1212 of the battery 506 and the negative terminal 1214 of the motor 222. Because both terminals 1214, 1216 of the motor 222 are connected to a single electrode 1212 of the battery 506, the motor 222 may not operate.

The clinician may initiate a firing operation by actuating the firing trigger 122, which, via the actuator 221, may cause the firing switch 220 to transition to a second state where the points 1 and 3 are connected. This may create an electrical connection between the negative terminal 1214 of the motor 222 and the negative electrode 1210 of the battery 506 (e.g., via pints 1 and 2 of the firing switch 220 and pins 4 and 5 of the relay 1208. This may cause the motor 222 to rotate in a forward direction. For example, the motor may rotate the gearbox 224, intermediate gear 230, drive gear 232 and rack 238 to ultimately push the firing bar 108 distally.

When the firing bar 108 reaches the end of its stroke, the end-of-stroke switch 1204 may transition from the position shown in FIG. 52 to a position where the points 1 and 2 of the switch 1204 are connected. This may connect pin 3 of the relay 1208 to the negative electrode 1210 of the battery 506 (e.g., via the pin 4-5 connection of the relay 1208). In turn, this may energize the relay 1208 causing removal of the electrical connection between pins 4 and 5 and generation of an electrical connection between pins 5 and 6. When the clinician releases the firing trigger 122, the firing switch may revert to the state shown in FIG. 52. This may cause the motor 222 to be connected to the battery 506 with a reverse polarity. For example, the positive terminal 1216 of the motor 222 may be connected to the negative electrode 1210 of the battery 506 via the switch 1204 and the relay 1208 (e.g., via pins 5 and 6). The negative terminal 1214 of the motor 222 may be connected to the positive electrode 1212 of the battery 506 via the firing switch 220. As a result, the motor 222 may rotate in reverse, pulling the firing bar 108 proximally, via the gearbox 224, intermediate gear 230, drive gear 232 and rack 238.

At the conclusion of the firing operation, the relay 1208 may be in a state where there is no electrical connection between pins 4 and 5. In this state, the instrument 102 may not be re-fired (e.g., the motor 222 may not be connected to the batter 506 with the correct polarity to cause forward rotation). According to various embodiments, a clamp switch 1206 may be positioned to energize the relay 1208 (e.g., pulling pin 1 low) in order to transition the relay 1208 back to the initial state having an electrical connection between pins 4 and 5. This may allow the instrument 102 to fire again. The clamp switch 1206 may be in mechanical communication with a portion of the drive train actuated by the closure trigger 120 to close the anvil 114 against the elongate channel 110. For example, the clamp switch 1206 may be in mechanical communication with the clamp lock 244 described herein above. When the anvil 114 is closed against the elongate channel 110 (e.g., when the clamp lock 244 is engaged), the switch 1206 may be in the position shown in FIG. 52, resulting in an electrical connection between points 1 and 3 of the switch 1206. When the clamp lock 244 is disengaged, the clamp switch 1206 may be configured to create an electrical connection between points 1 and 2, energizing the relay 1208 as described. Accordingly, after the instrument 102 is fired, the circuit 1200 may be configured to prevent the motor 222 from operating in the forward direction until the end effector 104 is re-opened. This may prevent the clinician from accidentally re-firing the instrument 102 before the end effector 104 is opened to install a new staple cartridge 132. According to various embodiments, the instrument 102 may comprise a mechanical lock-out device in addition to the relay lock-out implemented by the circuit 1200. The circuit 1200, as described herein, however, may prevent the clinician from driving the instrument 102 into the mechanical lock-out. This may save wear and tear on the instrument 102 and may also prevent clinician confusion that may occur when the device is in a mechanical lock-out state.

FIG. 53 illustrates one embodiment of the control circuit 1200 with additional switches and features. For example, the circuit 1200, as shown in FIG. 53, may additionally comprise an emergency access or bailout door switch 1218. The emergency access door switch 1218 may be in mechanical communication with the emergency access door 248. For example, when the emergency access door 248 is in place, the switch 1204 may be closed, as shown in FIG. 53. When the emergency access door 248 is removed, the switch 1204 may be opened, creating an open circuit relative to the negative terminal of the battery 506. A stroke position switch 1220 may be connected to switch a resistive element 1222 into and out of the circuit 1200 based on the position of the firing bar 108. The resistive element may be a single resistor and/or a resistor network connected in series, parallel (as shown) or any other suitable configuration. When the resistive element 1222 is switched into the circuit 1200, the current provided to the motor 222 may be reduced. This may reduce the speed and torque provided by the motor 222. Additionally, the control circuit 1200, as illustrated in FIG. 53 may comprise a PTC or other thermal fuse element 1224 to break a connection between the motor 222 and the battery 506 in the event that too much heat is generated (e.g., by the resistive element 1222).

FIG. 54 is a flowchart showing one embodiment of a process flow 1301 showing the firing of the instrument 102 utilizing the control circuit 1200 as illustrated in FIG. 53. At 1300, the instrument 102 may be ready to fire. For example, the switches 1218, 1206, 1220, 220, 1204 and relay 1208 may be configured as illustrated in Table 1 below:

TABLE 1

| Switch | Pin/Point Connection |
| --- | --- |
| Emergency Access Door (1218) | 1-2 |
| Clamp (1206) | 1-2 |
| Stroke Position (1220) | 1-2 |
| Fire (220) | 1-3 |
| End-of-stroke/Motor Direction (1204) | 1-3 |
| Relay (1208) | 4-5 |

At 1302, the clinician may actuate the firing trigger 122. This may cause the fire switch 220 to close, creating a connection between points 1 and 2 of the switch 220. Accordingly, the positive terminal of the motor 222 may be connected to the positive electrode 1212 of the battery 506 via the end-of-stroke/motor direction switch 1204. The negative terminal 1214 of the motor 222 may be connected to the negative electrode 1210 of the battery 506 via the thermal fuse element 1224, the resistive element 1222, and the connection between pins 4 and 5 of the relay. This may cause rotation of the motor 222 resulting in distal movement of the firing bar 108 (e.g., via the gearbox 224, intermediate gear 230, drive gear 232 and rack 238). Because the resistive element 1222 is electrically connected between the motor 222 and the battery 506, the current provided to the motor 222 may be reduced. This may, in turn, reduce the speed and/or torque provided by the motor 222 while the resistive element 1222 is active.

At 1304, the firing bar 108 may pass a predetermined position in its firing stroke. This may cause the stroke position switch 1220 to be opened, causing a connection between points 1 and 2 of the switch 1220. This may, in turn, switch the resistive element 1222, thermal fuse 1224, and relay 1208 out of circuit, allowing full current to be provided to the motor 222. The predetermined position in the firing stoke, in various embodiments, may be a point past which a mechanical lock-out is no longer possible and/or likely. For example, the resistive element 1222 may be utilized to limit the current to the motor 222 during the portion of the firing stroke where the firing bar 108 or other drive train element may encounter a mechanical lock-out. This may limit damage to the drive train or other component of the device 102 if the mechanical lock-out is encountered. When the possibility of encountering a mechanical lock-out has passed, the stroke position switch 1220 may be actuated to switch out the resistive element 1222, allowing full power to be provided to the motor 222 (e.g., for cutting tissue).

The firing bar 108 may reach the end of its stroke (e.g., at or near its distal-most position) at 1306. At this point, the end-of-stroke/motor direction switch 1204 may be actuated, causing it to be connected between points 1 and 2. In this way, the positive terminal 1216 of the motor 222 may be electrically connected to the negative electrode 1210 of the battery 506. The pin 3 of the relay 1208 may also be electrically connected to the negative electrode 1210 of the battery 506, energizing the relay 1208 and breaking the connection between relay pins 4 and 5. When the clinician releases the trigger 122 at 1308, the firing switch 220 may also be actuated, causing it to be connected between points 1 and 2. This may cause the negative terminal 1214 of the motor to be electrically connected to the positive electrode 1212 of the battery 506. In this way, the rotation direction of the motor 222 may be reversed, causing the motor 222 to return the firing bar to its initial, proximal position (e.g., via the via the gearbox 224, drive gear 232 and rack 238).

Similar to embodiment described above, when the relay 1208 is opened (e.g., the connection between pins 4 and 5 is broken), it may not be possible to rotate the motor 222 in a forward direction to fire the firing bar 108 until the clamp switch 1206 is actuated (e.g., by opening the end effector 104). In this way, the clinician may be prevented from re-firing the instrument 102 prior to opening the end effector 104, for example, to load a new staple cartridge 132. Also, similar to the embodiment described above, the clinician may abort a firing stroke by manually switching the end-of-stroke/motor direction switch 1204 to the state where points 1 and 2 are connected, causing the circuit 1200 and instrument 102 to behave as described above with respect to 1306 and 1308.

FIGS. 55-59 show the orientation and operation of various embodiments of the switches 1218, 1206, 1220, 220, and 1204 described above. FIG. 55 illustrates a perspective view of one embodiment of the circuit board 1202 coupled to the battery dock 850. The circuit board 1202 and battery dock 850, as shown, may be positioned within the handle 106 of the instrument 102, for example, as illustrated in FIG. 7. FIG. 55 shows, on the circuit board 1202, the emergency access door switch 1218, the clamp switch 1206, the stroke position switch 1220, the trigger switch 220 and the end-of-stroke/motor direction switch 1204. FIG. 56 illustrates a cut away view of one embodiment of the instrument 102 showing the emergency access door switch 1218. The switch 1218 may comprise an actuator 1304, which may be spring biased. The emergency access door 248, as shown, may comprise an arm 1302. The arm 1302 may be positioned under the actuator 1304 of the switch 1218. When the emergency access door 248 is removed, the arm 1302 may be removed from under the actuator 1304, changing the state of the switch 1218.

FIG. 57 illustrates another cut away view of one embodiment of the instrument 102 showing the clamp switch 1206. The clamp switch 1206 may comprise an actuator 1306. The actuator 1306 may be positioned such that the state of the switch 1206 is changed when the clamp release button 124 is actuated to unclamp the end effector 104.

FIG. 58 shows another cut away view of one embodiment of the instrument 102 showing the stroke position switch 1220. The stroke position switch 1220 may comprise an actuator 1308 and an actuator lever 1310. The actuator lever 1310 may ride along a top surface of the rack 238. According to various embodiments, the rack 238 may define an indentation 1312 along its top surface. The indentation 1312 may be positioned longitudinally on the rack such that the actuator lever 1310 of the switch 1220 falls into the indentation 1312 at the predetermined position of the firing stroke referred to with respect to FIG. 54. Alternatively, it will be appreciated that the rack 238 may comprise a protrusion positioned to contact the actuator at the predetermined part of the firing stroke.

FIG. 59 illustrates another cut away view of one embodiment of the instrument 102 showing the end-of-stroke/motor reverse switch 1204. The switch 1204 may comprise an actuator 1322. The actuator 1322 may be activated by an actuator reverse motor button 1320 or by the rack 238 as it reaches the distal end of its travel (e.g., indicating an end of the stroke of the firing bar 108). For example, the rack 238 may comprise a protrusion 1324 that contacts the actuator 1322 of the switch 1204. Also, for example, the rack 238 may comprise an indentation or cavity (not shown) positioned to contact the actuator 1322 at the distal end of the travel of the track 238.

Although the device described herein shows the rotational movement of the motor 222 being translated into longitudinal motion in the handle 106 (e.g., via the rack 238 and firing bar 108), it will be appreciated that instruments according to various embodiments may perform this translation outside of the handle, for example, in the shaft, or at the end effector itself. For example, in some embodiments, a rotating drive shaft (not shown) may extend some or all of the way through the shaft 114 from the handle 106 to the end effector 104. The various switches described herein may be utilized in such an embodiment. For example, the various switches described herein may be positioned to be actuated in the same relationship to the position of the firing bar 108 as described herein.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For another example, although the E-beam firing beam 108 has advantages for an endoscopically employed surgical severing and stapling instrument 102, a similar E-Beam may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. For yet another example, although an illustrative handle portion 106 described herein is manually operated by a clinician, it is consistent with aspects of the invention for some or all of the functions of a handle portion to be powered (e.g., pneumatic, hydraulic, electromechanical, ultrasonic, etc.). Furthermore, controls of each of these functions may be manually presented on a handle portion or be remotely controlled (e.g., wireless remote, automated remote console, etc.).

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A powered surgical instrument for cutting and fastening tissue, the instrument comprising:
   an end effector comprising:
      a first jaw member;
      a second jaw member coupled to move relative to the first jaw member from an open position, where the jaw members are apart from one another, to a closed position; and
      a firing bar positioned to fire by translating within the end effector when the first and second jaw members are in the closed position;
   a drive device mechanically coupled to the firing bar;
   a drive train mechanically coupled to the drive device and to the firing bar;
   a clamping trigger mechanically coupled to the end effector such that the clamping trigger defines an actuated position that causes the second jaw member to pivot towards the first jaw member and an un-actuated position that causes the second jaw member to pivot away from the first jaw member;
   a control circuit, wherein the control circuit comprises:
      a power supply comprising a first terminal and a second terminal;
      a switching device alternately configurable between a first connection state and a second connection state;

a firing switch positioned on a first electrical connection between the power supply, the drive device, and the switching device, wherein the firing switch defines an actuated position;

a clamp switch in mechanical communication with the clamping trigger and positioned on a second electrical connection between the power supply and the switching device;

an end-of-stroke switch defining a first position in which the end-of-stroke switch forms part of a third electrical connection between the first terminal of the power supply and the drive device, and a second position in which the end-of-stroke switch forms part of a fourth electrical connection between the second terminal of the power supply, the switching device, and the drive device, wherein the end-of-stroke switch is in physical contact with at least a portion of the drive train positioned to transition the end-of-stroke switch to the second position when the firing bar reaches an end of stroke;

wherein the first electrical connection is completed when the firing switch is in the actuated position and the switching device is in the first connection state;

wherein, upon the end-of-stroke switch transitioning to the second position, the fourth electrical connection is completed, causing the switching device to transition to the second state, wherein the transition to the second state causes the switching device to break the first electrical connection; and wherein, when the clamping trigger is in the un-actuated position, the clamp switch is closed to complete the second electrical connection causing the switching device to transition to the first state.

2. The surgical instrument of claim 1, wherein the first jaw member is shaped to receive a staple cartridge and the second jaw member defines at least one staple pocket for receiving and forming a staple.

3. The surgical instrument of claim 2, wherein the firing bar is in mechanical communication with a staple driver to push the staple driver distally upon firing.

4. The surgical instrument of claim 1, wherein the firing bar comprises a cutting edge.

5. The surgical instrument of claim 1, wherein the drive train comprises a rack translatable distally and proximally, wherein the rack is in mechanical communication with the firing bar, wherein the rack defines at least one geared face.

6. The surgical instrument of claim 5, wherein the drive device is positioned to rotate a gear in mechanical communication with the rack.

7. The surgical instrument of claim 6, wherein rotational motion of the drive device and gear in a first direction causes the rack and the firing bar to translate distally, and wherein rotational motion of the drive device and gear in a second direction causes the rack and the firing bar to translate proximally.

8. The surgical instrument of claim 5, wherein the rack defines a protrusion, and wherein the end-of-stroke switch comprises an actuator positioned to contact the protrusion to actuate the end-of-stroke switch when the rack reaches a position indicating the end of the firing bar stroke.

9. The surgical instrument of claim 5, wherein the control circuit further comprises a stroke position switch positioned to actuate when the firing bar reaches a predetermined position; and a resistive element in electrical communication with the stroke position switch, wherein the stroke position switch is electrically connected to electrically switch the resistive element between the power supply and the drive device until actuated in response to the firing bar reaching the predetermined position.

10. The surgical instrument of claim 9, wherein the stroke position switch comprises an actuator, and wherein the rack defines a cavity positioned to receive the actuator of the stroke position switch to actuate the stroke position switch when the firing bar reaches the predetermined position.

11. The surgical instrument of claim 1, wherein the instrument further comprises a clamp lock mechanically positioned to lock the second jaw member against the first jaw member.

12. The surgical instrument of claim 11, wherein the clamp switch comprises an actuator positioned to be actuated upon release of the clamp lock.

13. The surgical instrument of claim 1, wherein the control circuit further comprises an emergency access door switch coupled to an emergency access door of the instrument such that opening of the emergency access door actuates the emergency access door switch to break an electrical connection to the power supply.

14. The surgical instrument of claim 1, wherein the switching device is a relay.

15. The surgical instrument of claim 14, wherein the relay is a latching relay.

16. The surgical instrument of claim 1, wherein the relay is at least one of a mechanical relay and an electromagnetic relay.

17. A powered surgical instrument for cutting and fastening tissue, the instrument comprising:

an end effector comprising:
    a first jaw member;
    a second jaw member coupled to move relative to the first jaw member from an open position, where the jaw members are apart from one another, to a closed position; and
    a firing bar positioned to fire by translating within the end effector when the first and second jaw members are in the closed position; and a drive device mechanically coupled to the firing bar; and a clamping trigger mechanically coupled to the end effector such that actuation of the clamping trigger causes the second jaw member to pivot towards the first jaw member;

a rack defining a protrusion, wherein the rack is translatable distally and proximally, wherein the rack is in mechanical communication with the firing bar, and wherein the rack defines at least one geared face;

a control circuit, wherein the control circuit comprises:
    a firing switch configured to be in electrical communication with a power supply for powering the drive device and in electrical communication with the drive device;
    a clamp switch in mechanical communication with the clamping trigger;
    a latching device in electrical communication with the clamp switch, the power supply and the drive device; and
    an end-of-stroke switch in electrical communication with the latching device, wherein the end-of-stroke switch comprises an actuator positioned to contact the protrusion of the rack to actuate the end-of-stroke switch when the rack reaches a position indicating the end of the firing bar stroke; and wherein the firing switch is electrically connected to, upon actuation, connect the power supply to the drive device via a first connection comprising the latching device and the firing switch;

wherein the end-of-stroke switch is electrically connected to, upon actuation, cause a change in a state of the latching device to break the first connection between the power supply and the drive device.

18. A powered surgical instrument for cutting and fastening tissue, the instrument comprising:
   an end effector comprising:
      a first jaw member;
      a second jaw member coupled to move relative to the first jaw member from an open position, where the jaw members are apart from one another, to a closed position; and
      a firing bar positioned to fire by translating within the end effector when the first and second jaw members are in the closed position; and
   a drive device mechanically coupled to the firing bar; and
   a clamping trigger mechanically coupled to the end effector such that actuation of the clamping trigger causes the second jaw member to pivot towards the first jaw member;
   a rack translatable distally and proximally, wherein the rack is in mechanical communication with the firing bar, and wherein the rack defines at least one geared face;
   a control circuit, wherein the control circuit comprises:
      a firing switch configured to be in electrical communication with a power supply for powering the drive device and in electrical communication with the drive device;
      a clamp switch in mechanical communication with the clamping trigger;
      a latching device in electrical communication with the clamp switch, the power supply and the drive device; and
      an end-of-stroke switch in electrical communication with the latching device;
      a stroke position switch positioned to actuate when the firing bar reaches a predetermined position; and
      a resistive element in electrical communication with the stroke position switch;
   wherein the firing switch is electrically connected to, upon actuation, connect the power supply to the drive device via a first connection comprising the latching device and the firing switch;
   wherein the end-of-stroke switch is positioned to be actuated at an end of stroke of the firing bar and, upon actuation, cause a change in a state of the latching device to break the first connection between the power supply and the drive device;
   wherein the stroke position switch is electrically connected to electrically switch the resistive element between the power supply and the drive device until actuated in response to the firing bar reaching the predetermined position;
   wherein the stroke position switch comprises an actuator, and wherein the rack defines a cavity positioned to receive the actuator of the stroke position switch to actuate the stroke position switch when the firing bar reaches the predetermined position.

19. A powered surgical instrument for cutting and fastening tissue, the instrument comprising:
   an end effector comprising:
      a first jaw member;
      a second jaw member coupled to move relative to the first jaw member from an open position, where the jaw members are apart from one another, to a closed position; and
      a firing bar positioned to fire by translating within the end effector when the first and second jaw members are in the closed position; and
   a drive device mechanically coupled to the firing bar; and
   a clamping trigger mechanically coupled to the end effector such that actuation of the clamping trigger causes the second jaw member to pivot towards the first jaw member;
   an emergency access door; and
   a control circuit, wherein the control circuit comprises:
      a firing switch configured to be in electrical communication with a power supply for powering the drive device and in electrical communication with the drive device;
      a clamp switch in mechanical communication with the clamping trigger;
      a latching device in electrical communication with the clamp switch, the power supply and the drive device; and
      an end-of-stroke switch in electrical communication with the latching device;
      an emergency access door switch coupled to the emergency access door such that opening of the emergency access door actuates the emergency access door switch to break an electrical connection to the power supply; and
   wherein the firing switch is electrically connected to, upon actuation, connect the power supply to the drive device via a first connection comprising the latching device and the firing switch;
   wherein the end-of-stroke switch is positioned to be actuated at an end of stroke of the firing bar and, upon actuation, causes a change in a state of the latching device to break the first connection between the power supply and the drive device.

* * * * *